US012674776B2

(12) United States Patent
Fury et al.

(10) Patent No.: US 12,674,776 B2
(45) Date of Patent: Jul. 7, 2026

(54) ELECTROCHEMICAL SENSORS FOR ANALYTE DETECTION IN WATER AND REFERENCE CORRECTION METHOD

(71) Applicant: Brewer Science, Inc., Rolla, MO (US)

(72) Inventors: Jonathan J. Fury, Springfield, MO (US); Xi Cao, Tracy, CA (US); Austin Peters, Springfield, MO (US); Chad Lakin, Springfield, MO (US); Cody Simmons, Springfield, MO (US); Alec Neeson, Springfield, MO (US)

(73) Assignee: Brewer Science, Inc., Rolla, MO (US)

( * ) Notice: Subject to any disclaimer, the term of this patent is extended or adjusted under 35 U.S.C. 154(b) by 983 days.

(21) Appl. No.: 17/856,816

(22) Filed: Jul. 1, 2022

(65) Prior Publication Data

US 2023/0018859 A1 Jan. 19, 2023

Related U.S. Application Data

(60) Provisional application No. 63/217,339, filed on Jul. 1, 2021.

(51) Int. Cl.
*G01N 27/48* (2006.01)
*G01N 27/333* (2006.01)
(Continued)

(52) U.S. Cl.
CPC ......... *G01N 27/38* (2013.01); *G01N 27/3335* (2013.01); *G01N 27/4161* (2013.01); *G01N 27/48* (2013.01); *G01N 33/182* (2013.01)

(58) Field of Classification Search
CPC .... G01N 27/30; G01N 27/333; G01N 27/416; G01N 27/48–49; G01N 33/1813–182; G01N 33/20–2022; G01N 33/2028
See application file for complete search history.

(56) References Cited

U.S. PATENT DOCUMENTS 4,227,988 A 10/1980 Galwey et al.
6,447,670 B1 * 9/2002 Holmstrom ........ G01N 33/4925 204/402

(Continued)

FOREIGN PATENT DOCUMENTS

CN 207408418 5/2018
KR 10-1567980 11/2015
KR 10-2018-0072509 6/2018

OTHER PUBLICATIONS

Economou, Anastasios, "Screen-Printed Electrodes Modified with "Green" Metals for Electrochemical Stripping Analysis of Toxic Elements," Sensors 18 (2018): 1032, 23 pages.

(Continued)

*Primary Examiner* — James Lin
*Assistant Examiner* — Vivian A Tran
(74) *Attorney, Agent, or Firm* — HOVEY WILLIAMS LLP

(57) ABSTRACT

A sensing platform for continuous water resource monitoring by electrochemical detection and solution parameter correction is provided. The sensing platform employs a solid-state electrolyte three-electrode cell, creating a high ionic strength environment within the solid-state electrolyte membrane, which is in ion exchange equilibria with the sampled solution. This device may be used as a standalone sensor in environments where the water parameters (pH temperature, and ionic strength) are controlled, or in concert with compensation sensors where water parameters are not controlled.

14 Claims, 44 Drawing Sheets

(51) Int. Cl.

| | |
|---|---|
| ***G01N 27/38*** | (2006.01) |
| ***G01N 27/416*** | (2006.01) |
| ***G01N 33/18*** | (2006.01) |

(56) References Cited

U.S. PATENT DOCUMENTS

| | | | | |
|---|---|---|---|---|
| 9,157,003 | B2 | 10/2015 | Landorf et al. | |
| 2004/0058454 | A1 | 3/2004 | Bolbot et al. | |
| 2011/0199094 | A1 | 8/2011 | Lou | |
| 2012/0247978 | A1* | 10/2012 | Zevenbergen ..... | G01N 33/0047 204/414 |
| 2012/0261257 | A1 | 10/2012 | Vanjari et al. | |
| 2014/0114153 | A1 | 4/2014 | Bohm et al. | |
| 2019/0041371 | A1 | 2/2019 | Dinsmore | |
| 2019/0060556 | A1 | 2/2019 | Huiszoon et al. | |
| 2019/0277802 | A1 | 9/2019 | Huo | |
| 2019/0298233 | A1 | 10/2019 | Shin et al. | |
| 2019/0376927 | A1* | 12/2019 | Gahlings ............ | G01N 27/4165 |
| 2021/0292581 | A1 | 9/2021 | Chen et al. | |
| 2022/0091142 | A1 | 3/2022 | Chung | |

OTHER PUBLICATIONS

Alves et al., "Multi-element determination of metals and metalloids in waters and wastewaters, at trace concentration level, using electroanalytical stripping methods with environmentally friendly mercury free-electrodes: A review," Talanta 175 (2017) 53-68, 16 pages.

Kaaret et al., "Voltammetry without Supporting Electrolyte Using a Platinum Working Electrode Supported on an Ion Exchange Membrane," Analytical Chemistry 60 (1988) 657-662, 6 pages.

Gao et al., "Wearable Microsensor Array for Multiplexed Heavy Metal Monitoring of Body Fluids." ACS Sensors 1 (2016) 866-874, 13 pages.

International Search Report and Written Opinion mailed Oct. 26, 2022 in corresponding PCT/US2022/036019 filed Jul. 1, 2022, 11 pages.

Machine translation of Korean Patent No. 10-1567980, 13 pages.

Machine translation of Chinese Patent No. 207408418, 12 pages.

Office Action (Restriction) mailed Sep. 18, 2024 in co-pending U.S. Appl. No. 17/855,866, 7 pages.

Office Action mailed Jan. 30, 2025 in co-pending U.S. Appl. No. 17/855,866, 53 pages.

Mirceski et al., "Square-wave voltammetry," ChemTexts (2018) 4:17, 14 pages.

Namuduri et al., "Review—Deep Learning Methods for Sensor Based Predictive Maintenance and Future Perspectives for Electrochemical Sensors," Journal of the Electrochemical Society, 2020, 167, 037552, 12 pages.

Cuartero, Maria, "Electrochemical sensors for in-situ measurement of ions in seawater," Sensors and Actuators: B. Chemical 334 (2021) 129635, 19 pages.

Jadresko et al., "A formal scan rate in staircase and square-wave voltammetry," Journal of Electroanalytical Chemistry 645 (2010) 103-108, 6 pages.

Chen et al., "Electrochemical sensing and biosensing based on square wave voltammetry," Anal. Methods, 2013, 5, 2158-2173, 16 pages.

* cited by examiner

| Sensor Group | Linear Range | Equation | $R^2$ |
|---|---|---|---|
| 1 | 0 – 250 ppb | Ip = 0.07325(x) – 0.3013 | 0.963 |
| 2 | 0-250 ppb | Ip = 0.08593(x) – 0.7309 | 0.958 |

ELECTROCHEMICAL SENSORS FOR ANALYTE DETECTION IN WATER AND REFERENCE CORRECTION METHOD

STATEMENT REGARDING FEDERALLY SPONSORED RESEARCH OR DEVELOPMENT

This invention was made with Government support under W912HZ-18-2-0003 entitled "PRINTED ELECTRONIC NANO CARBON-BASED DEVICES AND SYSTEMS TO IMPROVE REAL-TIME SURFACE WATER CONTAMINATION SENSING," subaward 18004-001, and under W912HZ-21-2-0019 entitled "QUANTITATIVE WATER SENSING ARRAY FOR RAPID SENSING AND CONTINUOUS MONITORING," subaward 20206-001, both awarded by the Department of the Army ERDC. The United States Government has certain rights in the invention.

RELATED APPLICATIONS

The present application claims the priority benefit of U.S. Provisional Patent Application Ser. No. 63/217,339, filed Jul. 1, 2021, entitled PRINTED ELECTRONIC NANO-CARBON BASED DEVICES AND SYSTEMS TO IMPROVE REAL-TIME SURFACE WATER CONTAMINATION SENSING, incorporated by reference in its entirety herein.

BACKGROUND

Field

The present invention relates to sensors and the sensing of analytes in water.

Description of Related Art

Electrochemical techniques used for heavy metal detection include anodic stripping voltammetry, cathodic stripping voltammetry, and adsorptive stripping voltammetry employing a variety of electrode materials. These methods of detection require adequate supporting electrolyte to control the ionic impedance of the electrochemical cell and enable formation of the double layer structure at the working electrode interface. This limitation precludes existing technology from heavy metal detection in solution matrices having low ionic strength, including natural water, drinking water, and reverse osmosis (RO)—produced water.

Another limitation encountered involves the physical damage (e.g., delamination of electrodes) often encountered by sensors such as voltammetry sensors. Damaged sensors produce inconsistent and unreliable measurements, which typically results in the damaged sensors being discarded and replaced.

There is a need for solid-state cells for detecting analytes (such as heavy metals found in water) that controls the ionic impedance of that cell, avoids physical damage to that cell, and provides reliable measurements of the target analyte(s).

SUMMARY

The disclosure provides a method of monitoring for the presence of an analyte in water. The method comprises contacting a device comprising a working electrode with the water to be monitored.

In another embodiment, a sensor comprising the above working electrode is provided. The disclosure also provides a method of using the sensor to monitor for the presence of an analyte in water. The method comprises contacting a device comprising the sensor with the water to be monitored.

In a further embodiment, a voltametric sensor system is provided. The system comprises a sensor comprising a working electrode, a counter electrode, and a reference electrode. An electronic system is connected to the working electrode, the counter electrode, and the reference electrode. The electronic system is configured to apply a voltage difference between the working electrode and the reference electrode and to conduct a differential pulse voltametric scan over at least a portion of an electrochemical window extending from a start scan value to an end scan value using the working electrode, the counter electrode, and the reference electrode. The electronic system further comprises a dynamic electrochemical window calculator configured to change the end scan value of the electrochemical window to account for drift in the reference electrode.

In yet a further embodiment, the disclosure provides a method of using a voltametric sensor comprising a working electrode, a counter electrode, a reference electrode, and an electronic system connected to the working electrode, the counter electrode, and the reference electrode. The method comprises applying, via the electronic system, a differential pulse voltametric scan over at least a portion of an electrochemical window extending from a start scan value to an end scan value using the working electrode, the counter electrode, and the reference electrode. A drift in the reference electrode is determined via the electronic system, and the end scan value is changed, via the electronic system, to account for the drift in the reference electrode.

BRIEF DESCRIPTION OF THE DRAWINGS

Embodiments of the invention will become more fully apparent from the following detailed description, the appended claims, and the accompanying drawings in which like reference numerals identify similar or identical elements.

DETAILED DESCRIPTION

The present disclosure addresses the above needs by providing methods, sensors, and sensor systems for detecting the presence of analytes (e.g., lead, cadmium, copper, and/or nitrates, in water), preferably in a substantially continuous manner, while avoiding sensor damage, thus extending the sensor lifespan. Embodiments of the present invention minimize sensor damage due to excessive differential current and compensate for reference electrode drift by monitoring a differential current through the working electrode of a voltammetry sensor and adjusting the electrochemical window relative to the drift of the reference electrode.

Sensors

Figure 1:
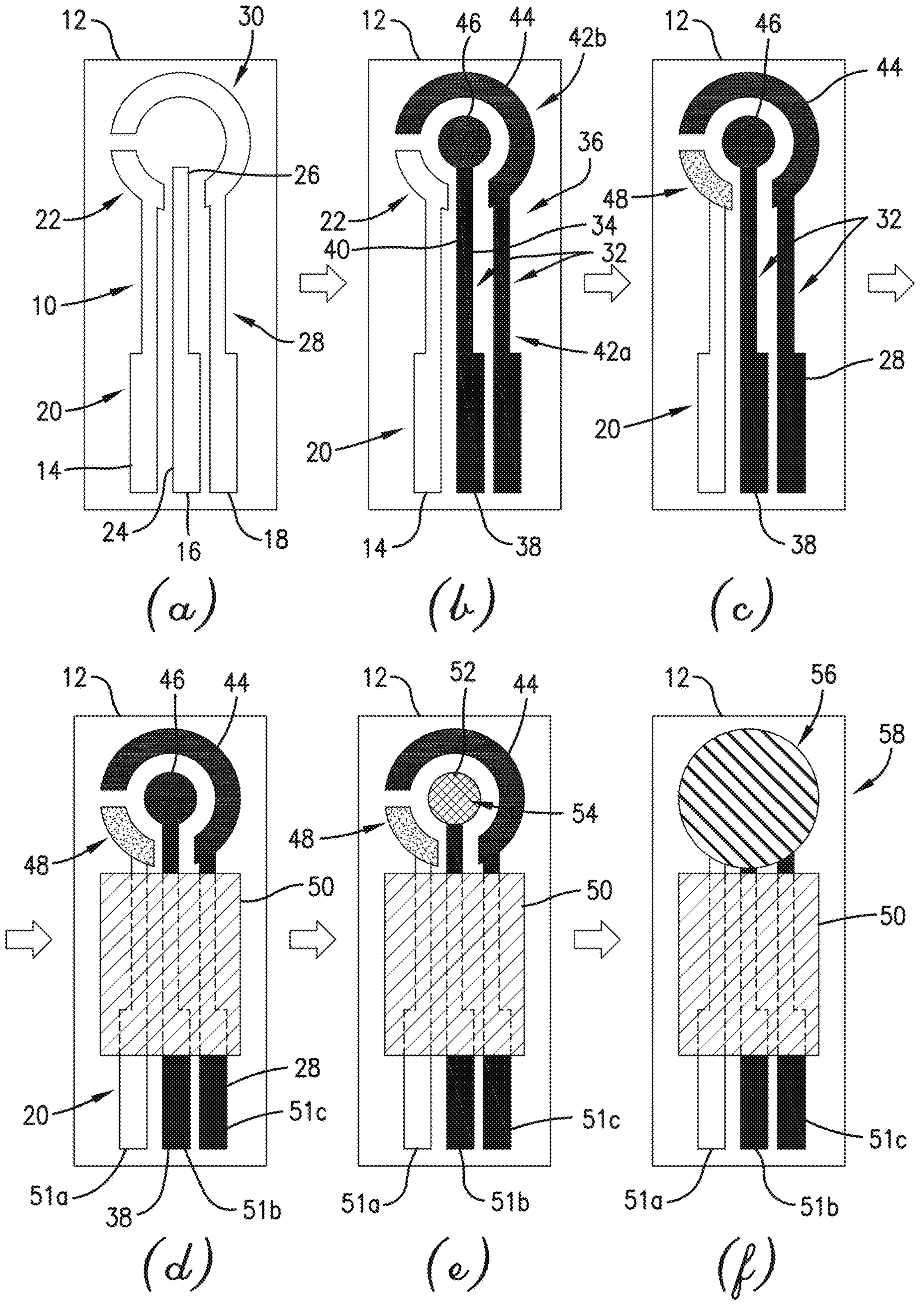
FIG. 1 is a schematic depiction of one process for making a sensor as described herein.

Referring to FIG. 1, one embodiment of a sensor that can be formed by the process described.

FIG. 1(*a*)

A current collector layer 10 is deposited on a substrate 12. The substrate 12 may be formed from any number of materials, including those selected from the group consisting of polymers, ceramics, metals, monocrystallines, and combinations thereof. Suitable organic polymers include those selected from the group consisting of cyclic olefin polymers (such as those sold as films under the name Zeonor® by Zeon Corporation, with ZEONEX® ZF14-188 being one preferred such film), fluorinated polymers such as polytetrafluoroethylene ("PTFE," such as those sold as films under the name Teflon® by DuPont), copolymers of tetrafluoroethylene and hexafluoropropylene ("FEP" and "PFA"), polyvinylidene fluoride, polyether ether ketone ("PEEK"), polyetherimide polyphenylene sulfide, polysulfones, polyoxymethylene ("POM"), polyimides, polyamides, polyether sulfones, polyethylene terephthalate ("PET"), polyacrylates, polymethacrylates, polystyrenes, polyesters, polyethylene naphthalate, and combinations of the foregoing.

The substrate 12 preferably has a low water absorbency and low moisture permeability. Preferably, water absorbency is less than about 3%, more preferably less than about 2%, and even more preferably less than about 1% according to ASTM method D570. It is also preferred that the substrate 12 does not experience hygroscopic expansion or similar deformation, which can generally be determined visually.

The substrate generally has a thickness of about 50 μm to about 5 mm, preferably about 50 μm to about 2.5 mm, more preferably about 75 μm to about 1,000 μm, and even more preferably about 100 μm to about 300 μm. The substrate 12 is preferably planar, or at least presents a planar surface one which current collector 10 is deposited. The substrate may be flexible, but should be rigid enough to enable the appropriate printing and deposition processes. Additionally, substrate 12 is generally rectangular in shape, but could also be configured to be square, circular, etc., as may be desired for the particular application. Substrate 12 is also preferably sized and shaped such that the entire current collector 10 can fit on the substrate surface and within the outer perimeter of substrate 12.

The current collector 10 may be deposited on the substrate 12 by any number of conventional techniques, including sputtering, electron beam evaporation, ion-assisted electron beam evaporation, thermal evaporation, ink-jet printing, screen printing, gravure printing, or flexography. The deposition method is suitably carried out so as to form an outline of the desired electrode patterns, i.e., reference electrode template 14, working electrode template 16, and counter electrode template 18. For example, if the current collector 10 is formed by sputtering, a mask (e.g., a molybdenum mask) having the desired electrode patterns can be used to achieve a current collector 10 with electrode templates 14, 16, and 18 of the desired shape and size.

Regardless of the formation method, reference electrode template 14 comprises a straight section 20 and a curved end 22. Working electrode template 16 includes a first end 24 and a second end 26, and counter electrode template 18 also includes a straight section 28 and a curved end 30.

The material from which current collector 10 is formed is chosen so that the current collector 10 exhibits high conductivity. That is, it is preferred that the current collector 10 has a total equivalent series resistance (i.e., as measured by a four point probe and a multimeter) of less than about 5 kΩ, preferably less than about 1000Ω, and more preferably less than about 100Ω, preferably at about 10 C to about 30 C. The current collector 10 may be formed of any conductive material that is not oxidized or reduced during device operation, including, but not limited to, gold, silver, platinum, palladium, copper, aluminum, nickel, poly(3,4-ethylenedioxythiophene)-poly (styrene sulfonate), poly (aniline), a carbonaceous material (e.g., carbon, amorphous carbon, carbon nanotubes, graphite, graphene, carbon nanobuds, glassy carbon, carbon nanofibers), and combinations thereof. Oxidation of a material can be tested using Tafel analysis, electrochemical impedance spectroscopy (EIS), or cyclic voltammetry in inert electrolyte solution or other electrochemical methods using inert electrolyte solution, for example. In one especially preferred embodiment, the current collector is gold. In another embodiment, the reference electrode template 14, working electrode template 16, and counter electrode template 18 of current collector 10 are made of the same material. In yet another embodiment, the reference electrode template 14 and the counter electrode template 18 are made of the same material, while the working electrode template 16 is formed of a different material. In one embodiment, the current collector 10 comprises a gold layer and is formed by sputtering, thus providing nobility and electrical resistance stability.

Regardless of the material chosen, the average thickness (as measured by an interferometer or stylus profilometer) of the current collector 10 is preferably about 10 nm to about 1,000 nm, more preferably about 50 nm to about 200 nm, and even more preferably about 100 nm.

FIG. 1(*b*)

As shown in FIG. 1(*b*), a protective conductive layer 32 is formed on working electrode template 16 and counter electrode template 18 of current collector 10, thus forming a protected working electrode 34 and a protected counter electrode 36. Protected working electrode 34 has first and second ends 38, 40 while protected counter electrode 36 has first and second portions 42*a*, 42*b*. Preferably first portion 42*a* of protected counter electrode 36 is substantially straight, while second portion 42*b* is preferably curved, as shown, forming a counter electrode 44. Protective conductive layer 32 is useful for protecting the protected working electrode 34 and protected counter electrode 36 of the current collector 10 from detaching from the surface of the substrate 12 when current passes through counter electrode 44 and the final working electrode (whose formation is described below) for an extended time.

As shown in FIG. 1(*b*), protective conductive layer 32 is also formed directly on a portion of the substrate 12 (i.e., with no intervening current collector layer 10 between it and substrate 12) at the second end 40 of protected working electrode 34 to form a sensing platform 46 extending into a space partially surrounded by, but spaced from, the curved ends 22,30 of the reference electrode template 14 and counter electrode 44. The distance between the sensing platform 46 and the reference electrode template 14 and the counter electrode 44 should be as small as possible, provided that it does not create electrical connections between any of the sensing platform 46, the reference electrode template 14, and the counter electrode 44.

The protective conductive layer 32 should be chemically inert and exhibit low resistance. That is, protective conductive layer 32 preferably has a sheet resistance (measured by 4 point probe) of about 1 Ω/square/mil to about 5 Ω/square/mil, more preferably about 1 Ω/square/mil to about 1000 Ω/square/mil, even more preferably about 1 Ω/square/mil to about 500 Ω/square/mil, and still more preferably about 1 Ω/square/mil to about 100 Ω/square/mil.

The protective conductive layer 32 may be formed of any conductive material that is not oxidized or reduced during device operation, including, but not limited to, carbonaceous materials (e.g., carbon, amorphous carbon, carbon nanotubes, graphite, graphene, carbon nanobuds, glassy carbon, carbon nanofibers), gold, platinum, silver, and combinations thereof, with conductive carbon being a particularly preferred material for forming protective conductive layer 32. Oxidation of a material can be tested using Tafel analysis, EIS, or cyclic voltammetry in inert electrolyte solution or other electrochemical methods using inert electrolyte solution, for example. The protective conductive layer 32 may be deposited by any appropriate method, including sputtering, electron beam evaporation, ion-assisted electron beam evaporation, thermal evaporation, ink-jet printing, screen printing, gravure printing, or flexography.

Regardless of the material utilized, the average thickness (as measured by an ellipsometer) of the protective conductive layer 32 is preferably about 1 μm to about 100 μm, more preferably about 5 μm to about 25 μm, and even more preferably about 13 μm.

FIG. 1(*c*)

Referring to FIG. 1(*c*), a reference electrode material is deposited as a layer on the curved end 22 of reference electrode template 14, thus forming a reference electrode 48. The reference electrode 48 is formed from any material conventionally used as a reference electrode in 3-electrode cells, including Ag/AgCl binder, chlorinated silver, platinum, silver, or combinations thereof.

The reference electrode material may be deposited by any conventional means, including stencil printing, screen printing, sputtering, electron beam evaporation, ion-assisted electron beam evaporation, thermal evaporation, ink-jet printing, screen printing, gravure printing, or flexography. The average thickness of the reference electrode 48 is preferably about 1 μm to about 100 μm, more preferably about 5 μm to about 25 μm, and even more preferably about 13 μm.

In the embodiment illustrated in FIG. 1, the reference electrode 48 is fixed to the same substrate 12 as the other components. It will be appreciated that in some embodiments, the reference electrode 48 could be used as an external reference electrode (i.e., not deposited on substrate 12). The reference electrode 48 can be a real electrode or a so-called pseudo reference electrode.

FIG. 1(*d*)

Referring to FIG. 1(*d*), an encapsulant layer 50 is then formed over all areas of reference electrode template 14, working electrode template 16, and counter electrode template 18 that are not to be exposed to the analyte. In the illustrated embodiment, encapsulant layer 50 is generally rectangular in shape, although that shape can be altered depending on the area to be protected from analyte contact. Additionally, the encapsulant layer 50 is sized and shaped to encapsulate all of the electrode templates 14, 16, and 18 portions that are to be protected from analyte contact and also to typically be in contact with portions of substrate 12 around and between electrode templates 14, 16, and 18. The encapsulant layer 50 defines the working electrode area precisely and improves measurement reproducibility by leaving counter electrode 44, sensing platform 46 (which will eventually become the final working electrode), and reference electrode 48 unencapsulated for further processing steps and eventual contact with the analyte. The encapsulant layer 50 also should be sized to leave uncovered portions of straight section 20 of reference electrode template 14, first end 38 of protected working electrode 34, and straight section 28 of counter electrode template 18, which will become leads 51*a*, 51*b*, and 51*c*, respectively.

The encapsulant layer 50 should be a dielectric material and preferably has an ionic impedance (measured by electrochemical impedance spectroscopy) of at least about 1 MΩ, preferably at least about 5Ω, and more preferably at least about 10 MΩ. The encapsulant layer 50 must exhibit sufficient adhesion to adjacent layers (including substrate 12) to prevent leakage and/or diffusion of the analyte solution around and/or through the encapsulant layer 50.

The encapsulant layer 50 can be formed from a material chosen from one or more of poly (cycloolefins), polyesters, polyimides, silicones, polyacrylates, polysulfones, and combinations thereof. In one embodiment, the encapsulant is DuPont 5018 dielectric material. The insulation layer may be deposited by any appropriate means, including screen printing, ink-jet printing, gravure printing, and flexography. An additional UV cure or baking step may be used to cure the encapsulant layer 50. The average thickness of the encapsulant layer 50 is preferably about 1 μm to about 100 μm, more preferably about 5 μm to about 25 μm, and even more preferably about 13 μm.

FIG. 1(*e*)

Referring to FIG. 1(*e*), a sensing layer 52 is formed on sensing platform 46 extending from working electrode template 16, thus forming working electrode 54. Sensing layer 52 provides a conductive surface for analyte accumulation. The sensing layer 52 preferably has a sheet resistance (measured by 4 point probe) of about 1 Ω/square/mil to about 5 Ω/square/mil, more preferably about 1 Ω/square/mil to about 1000 Ω/square/mil, even more preferably about 1 Ω/square/mil to about 500 Ω/square/mil, and still more preferably about 1 Ω/square/mil to about 100 Ω/square/mil.

The sensing layer 52 is preferably formed from a material chosen from one or more of bismuth, antimony, tin, gold, silver, carbon (including carbon nanotubes and/or other carbon nanomaterials), boron-doped diamond, copper, or combinations thereof, as well as alloys, layered structures, and/or bimetallic thick film electrodes of bismuth, antimony, tin, gold, silver, carbonaceous materials (e.g., carbon, amorphous carbon, carbon nanotubes, graphite, graphene, carbon nanobuds, glassy carbon, carbon nanofibers), boron-doped diamond, or combinations thereof.

In one embodiment, the sensing layer 52 is sputtered silver. In another embodiment, the sensing layer 52 is sputtered bismuth. The sensing layer 52 may be deposited by any conventional means, including physical vapor deposition, sputtering, electron beam evaporation, ion assisted electron beam evaporation, thermal evaporation, ink jet printing, screen printing, gravure printing, or flexography. The average thickness of the sensing layer 52 is preferably about 10 nm to about 1,000 nm, more preferably about 100 nm to about 500 nm, and even more preferably about 200 nm. Sensing layer 52 preferably has a total equivalent series resistance measured by multimeter of less than about 5 kΩ, preferably less than about 1000Ω, and more preferably less than about 100Ω.

FIG. 1(*f*)

Finally, and referring to FIG. 1(*f*), a membrane layer 56 is formed over counter electrode 44, reference electrode 48, some or all of second end 40 of the protected working electrode 34, and working electrode 54. When the sensor is immersed in a fluid, the membrane layer 56: (1) holds the solution resistance/impedance low at the electrodes by providing a locally high ionic strength to support ionic conduction and associated double layer formation in the absence of supporting electrolyte, (2) reaches a steady state ion-exchange condition with the surrounding sample solution, and (3) preferably both (1) and (2). "High ionic strength" refers to sufficient ionic strength to support ion conduction, which is generally about 1Ω to about 5 Ω impedance between the counter electrode 44 and working electrode 54, determined by electrochemical impedance spectroscopy, and preferably at about 10 kHz. The ion exchange properties of membrane layer 56 may be selective toward target analytes.

The membrane layer 56 can be formed from any material capable of the above. Examples of such materials include those comprising sulfonates, carboxylates, phosphonates, amines, quaternary amine functionalized poly (tetrafluoroethylene) (such as the polymer sold under the name Nafion®), polystyrenes, polystyrene copolymers, polyacrylates, polymethacrylate, polybutadiene, polyisoprene, or combinations thereof.

One particularly preferred material for forming membrane layer 56 involves using a modified version of an acidic polymer such as those sold under the name Nafion®. In this embodiment, a dispersion is first prepared by neutralizing the acidic polymer with a base to convert it to its corresponding salt. The polymer is preferably dispersed or dissolved in a solvent system comprising one or more solvents. Solvents typically present in such dispersions include 1-propanol, ethanol, mixed ethers, VOC solvents, and mixtures thereof. The total solvent(s) will typically be present in these dispersions at levels of about 65% by weight to about 90% by weight, and more preferably from about 75% by weight to about 85% by weight, with the balance of the weight being attributable to solids in the dispersion, and those solids being largely or entirely the acidic polymer solids.

The preferred acidic polymer is a copolymer of perfluoro acid ("PFA") and polytetrafluoroethylene ("PTFE") and comprises the structure

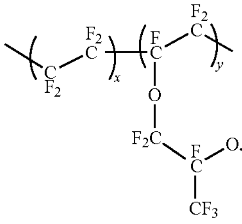

where $R^1$ is chosen from

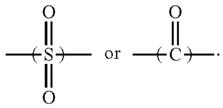

In one embodiment, the polymer has a weight average molecular weight of about 100 g/mol to about 2,000 g/mol, preferably about 200 g/mol to about 1,000 g/mol, and more preferably about 400 g/mol to about 600 g/mol.

In another embodiment, the molar ratio of x:y is about 3:1 to about 1:99, preferably about 1.2:1 to about 1:4, and more preferably about 1:1 to about 1:1.5.

One such polymer is commercially available as Nafion™ PFSA 20% Dispersions-D2021 and Nafion™ PFSA 20% Dispersions-D2020 (Fuel Cell Store, College Station, Texas) and comprises the structure

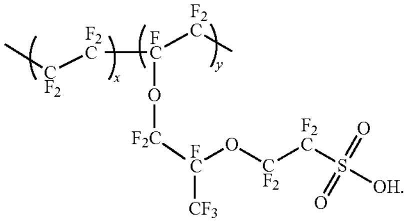

Neutralization is preferably accomplished by titrating the dispersion with a base. Suitable bases are Lewis bases and include sodium hydroxide, tetrabutylammonium hydroxide, silver acetate, silver lactate, zinc acetate, potassium hydroxide, tetraethylammonium hydroxide, tetramethylammonium hydroxide, sodium bicarbonate, ammonium hydroxide, sodium carbonate, and mixtures thereof. The final pH of the titrated solution is preferably from about 6.8 to about 7.2, more preferably from about 6.98 to about 7.02, and even more preferably about 7.

The resulting salt is preferably one or more of the acidic polymer's sodium salt, potassium salt, silver salt, ammonium salt, tetramethylammonium salt, tetraethylammonium salt, tetrabutylammonium salt, and/or zinc salt. In a preferred embodiment, the resulting salt comprises the structure

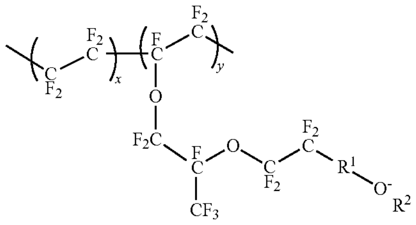

wherein $R^2$ is chosen from $Na^+$, $K^+$ $Ag^+$, $NH^{4+}$, $Zn^{2+}$,

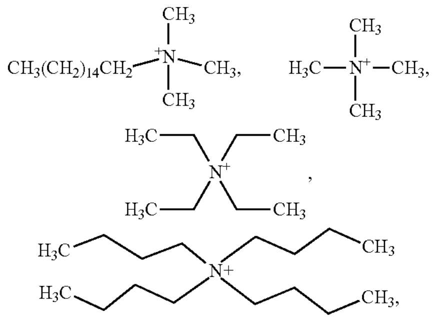

and mixtures of the foregoing.

Next, the resulting salt dispersion is subjected to a "solvent swap" to replace the low-boiling-point solvent that is part of the commercially available product with a new, high(er)-boiling-point solvent(s) that is capable of completely solubilizing the salt of this dispersion. The substitute solvent(s) is preferably added to the salt dispersion at a level of from about 50% by weight to about 500% by weight, and more preferably from about 80% by weight to about 120% by weight, based upon the total weight of the salt dispersion taken as 100% by weight. The boiling point of the high-boiling-point solvent(s) is preferably from about 100° C. to about 300° C., and more preferably from about 125° C. to about 250° C., particularly when the final material will be used for screen printing, stencil coating, or drawdown printing.

Suitable new (i.e., substitute) solvents include those chosen from water, 2-methyl-1,3 propanediol, 1,2-propanediol, 1,3-propanediol, 1,2-butanediol, 2,3-butanediol, 1,3-butanediol, 1,4-butanediol, 1,2-pentanediol, 2,4-pendanediol, 1,2-hexanediol, glycerol, 1,2,4-butanetriol butyl carbitol acetate, propylene carbonate, dimethyl glutarate, diethyl adipate, dimethyl adipate, propiophenone, N,N-dimethylacetamide, N,N-dimethylformamide, N-methyl-pyrrolidone, dimethyl sulfoxide, ethylene glycol, and mixtures thereof.

The majority of the original, low-boiling-point solvent or solvents is then removed. One preferred method for removing the low-boiling-point solvent or solvents is by rotor evaporation. Rotor evaporation is preferably performed at temperatures of from about 50° C. to about 75° C., and more preferably from about 60° C. to about 65° C. This preferably results in the removal of at least about 75%, preferably at least about 80%, more preferably at least about 95%, and even more preferably about 100% of the original solvent(s).

After removal of the original, low-boiling-point solvent(s), the resulting "solvent-swapped" salt dispersion with the new, high-boiling-point solvent system can be used as obtained. Advantageously, the viscosity of this solvent-swapped salt dispersion can also be controlled by adjusting the percent solids. The percent solids may be altered by evaporating some of the new solvent to increase the percent solids, and consequently, viscosity, or by incorporating additional substitute solvent(s) to decrease the percent solids, and consequently, viscosity.

When used for screen printing, stencil coating, or draw-down printing, the resulting solvent-swapped salt dispersion is preferably from about 10% by weight solids to about 35% by weight solids, and more preferably from about 15% by weight solids to about 25% by weight solids, with the balance of the dispersion in each instance being solvent. The viscosity of the resulting solvent-swapped salt dispersion, as measured by a Brookfield DV2T Viscometer (AMETEK Brookfield, Middleboro, MA, USA) at 25° C., is preferably from about 200 cP to about 8,000 cP, and more preferably from about 500 cP to about 5,500 cP.

When used for ink-jet printing or spray coating, the resulting solvent-swapped salt dispersion is preferably from about 0.2% by weight solids to about 20% by weight solids, and more preferably from about 0.5% by weight solids to about 5% by weight solids, with the balance of the dispersion in each instance being solvent. The viscosity of the resulting solvent-swapped salt dispersion, as measured by a Brookfield DV2T Viscometer (AMETEK Brookfield, Middleboro, MA, USA) at 25° C., is preferably from about 5 cP to about 500 cP, and more preferably from about 5 cP to about 250 cP.

Optional ingredients may be added, such as rheology modifiers, surfactants, cosolvents, and combinations thereof. Suitable rheology modifiers include bentonite clay and organic derivatives thereof (e.g., BENTONE SD®-2, BENTONE SD®-3, both available from Elementis, Windsor, NJ), cationic dispersants (e.g., Hypermer™ KD1, Hypermer™ KD6, both available from Croda Advanced Materials), and combinations thereof. When a rheology modifier is included, it is preferably present at levels of from about 0.1% by weight to about 5% by weight, more preferably from about 0.5% by weight to about 3% by weight, and still more preferably about 1% by weight, based upon the total weight of the solvent-swapped salt dispersion, or on the combined weights of the solvent-swapped salt dispersion and the cosolvent, in embodiments where a cosolvent is also included.

Suitable cosolvents include, but are not limited to, water, alcohols, other high-boiling-point solvents as described above, and combinations thereof. It will be appreciated that depending on the printing technology, the amount and type of cosolvent may vary greatly. When a cosolvent is included for screen-printable, draw-down-printable, and stencil-printable ink formulations, it is present at levels of from about 0.01% by weight to about 99.9% by weight, preferably from about 0.05% by weight to about 80% by weight, and more preferably from about 0.1% to about 10% by weight, based upon the combined weights of the solvent-swapped salt dispersion and the cosolvent. When a cosolvent is included for ink-jet-printable and spray-printable ink formulations, it is preferably present at levels of from about 80% by weight to about 99.99% by weight, and more preferably from about 90% by weight to about 99.95% by weight, based upon the combined weights of the solvent-swapped salt dispersion and the cosolvent. Cosolvents can be beneficial in situations where the intended printing technique requires a lower boiling point solvent system (lower relative to the boiling point of the solvent system if the cosolvent weren't present, e.g., at least about 20° C. lower, preferably at least about 50° C. lower, and more preferably at least about 50° C. to about 100° C. lower).

Surfactants include fluorosurfactants (e.g., nonionic ones such as Capstone™ FS3100, available from The Chemours Company FC, LLC), sodium dodecyl sulfate, polyethylene glycol tert-octylphenyl ether (such as that available under the name Triton™ X-100, from Sigma-Aldrich, Inc.), and combinations thereof. When a surfactant is included, it is preferably present at levels of from about 0.01% by weight to about 2% by weight, more preferably from about 0.05% by weight to about 0.5% by weight, and still more preferably about 0.2% by weight, based upon the total weight of the solvent-swapped salt dispersion, or on the combined weights of the solvent-swapped salt dispersion and the cosolvent, in embodiments where a cosolvent is also included.

In one embodiment, the dispersion consists essentially of, or even consists of, the salt and high-boiling point solvent (s).

In another embodiment, the dispersion consists essentially of, or even consists of, the salt, high-boiling point solvent(s), and one or more of a rheology modifier, surfactant, and/or cosolvent.

Regardless of the formation method, the films are ultimately dried, with the thickness varying greatly, depending upon the printing method and intended application. Film drying may be performed by any suitable method, including baking in a vacuum oven, box oven, or conveyor oven. The preferred drying temperature is from about 45° C. to about 150° C., and more preferably from about 60° C. to about 90° C. for a time period of about 2 hours to about 4 hours. In one embodiment, the printed, dried, film has a thickness of from about 100 nm to about 50 μm, and preferably from about 1 μm to about 25 μm, even more preferably about 15 μm. Preferably, the impedance of the printed salt film in pure water is below about 5 kΩ, and more preferably below about 2 kΩ, measured at about 5 kHz to about 100 kHz at a film thickness of about 5 μm to about 50 μm using a potentiostat (Gamry Instruments, Reference 3000, Warminster, PA, USA).

In one embodiment, the film comprises less than about 10% by weight, preferably less than about 5% by weight, and more preferably about 0% by weight triethylammonium methanesulfonate. In another embodiment, the film comprises less than about 20% by weight, preferably less than about 10% by weight, and more preferably about 0% by weight triethylammonium perfluorobutanesulfonate. In a particularly preferred embodiment, the film comprises the foregoing triethylammonium methanesulfonate and triethylammonium perfluorobutanesulfonate % by weight ranges in any combination.

In another embodiment the film consists essentially of, or even consists of, the previously described salt.

The materials described above are all suitable for forming the membrane layer 56. Regardless of the material from which the membrane layer 56 is formed, membrane layer 56 may be deposited by various conventional processes, including stencil printing, screen printing, ink jet printing, gravure printing, or flexography printing. It is preferred that the pH of the material used to fabricate the membrane layer 56 is about 4 to about 7, and more preferably from about 5 to about 6.

Figure 2:
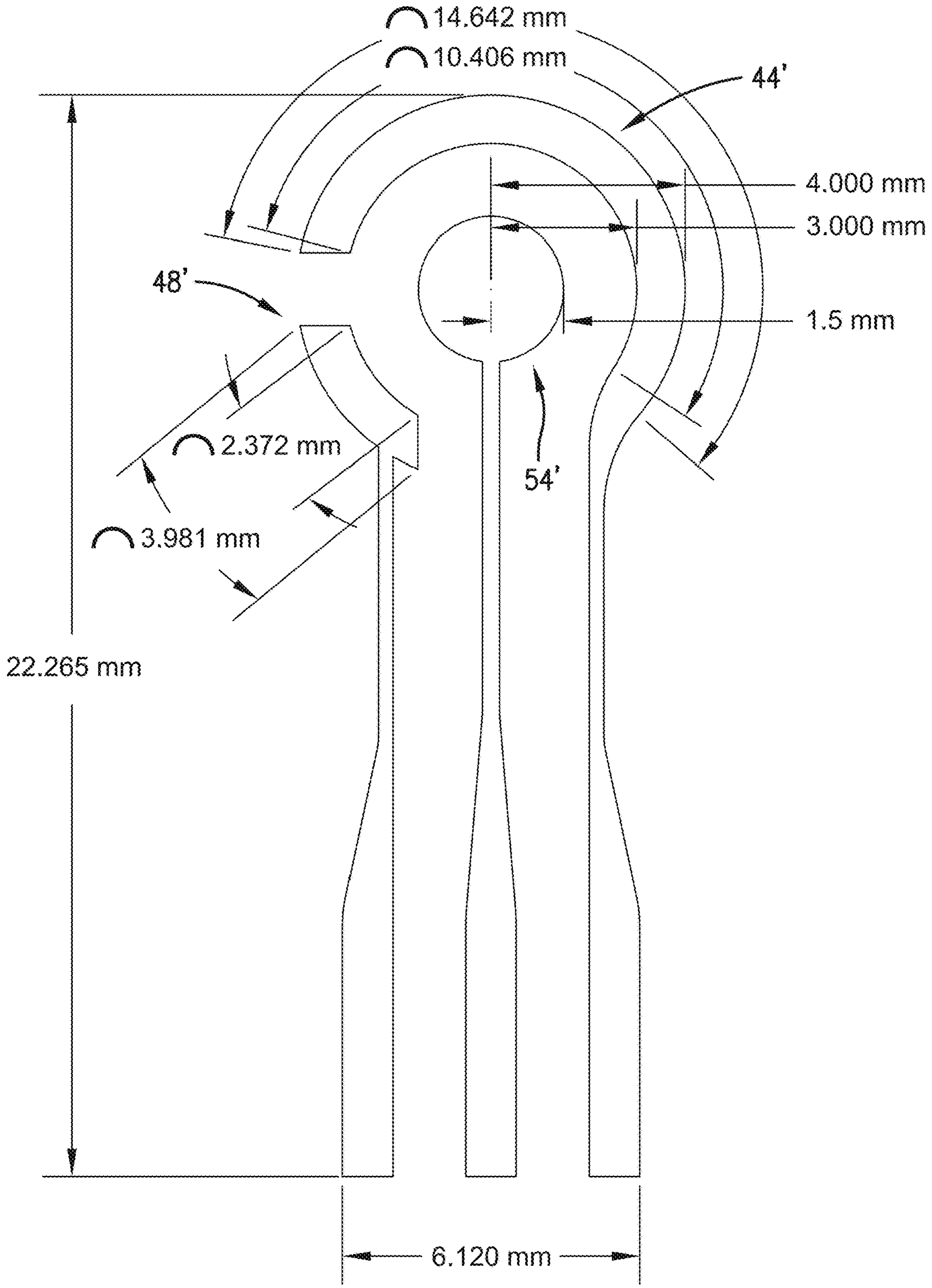
FIG. 2 is a schematic diagram providing exemplary dimensions of one sensor embodiment described herein.

The above process forms the final sensor 58, as shown schematically in FIG. 1(*f*). FIG. 2 provides exemplary dimensions for the electrodes of one embodiment of a sensor 58. Parts of the sensor shown in FIG. 2 corresponding to parts of sensor 58 are labeled with the same reference number except that a prime (¢) is added. The dimensions of a finished sensor using the electrodes shown in FIG. 2 are about 22.2 mm in height×6.1 mm in width. The working electrode 54', counter electrode 44', and reference electrode 48' surface areas are about 7.1 $mm^2$, about 67.7 $mm^2$, and about 18.4 $mm^2$, respectively. However, the sizes of the electrodes can vary. Importantly, the sensors formed herein are transducers, which are different from a transistor or electronic switch. It will be appreciated that a transducer, in its simplest definition transforms a signal from one energy form to another energy form, while a transistor in its simplest definition controls the flow of electricity. The latter would include a source (input) and a drain (output), neither of which are present in a transducer.

Advantageously, referring again to the sensor 58 in FIG. 1(*f*), the three electrodes (i.e., counter electrode 44, reference electrode 48, and working electrode 54) of sensor 58 are ionically connected by ionic conduction through the membrane layer 56, and the solution resistance is greatly reduced. In this structure, the solution resistance/impedance is held low by membrane layer 56, which forms an ionomer layer over the surface of the underlying electrodes 44, 48, 54. Ionomers possess ion exchange properties, due to the presence of immobilized charge on the polymer backbone. The membrane layer 56, therefore, provides a locally high ionic strength to support ionic conduction and associated double layer formation in the absence of supporting electrolyte. Ion exchange processes occur until an equilibria state has been reached, so the response time of this sensor may be dictated by the kinetics of ion exchange. The equilibria state is dictated by a combination of binding energies/affinities of the immobilized charges on the ionomer backbone with counterions present, and diffusion gradients between the ionomer membrane phase and the bulk solution in exchange. The concentration of exchangeable analyte within the ionomer membrane will depend not only on the bulk concentration, but also on the ionic strength or concentration of other competing exchangeable ions. This, along with double layer formation and cell impedance control enables analyte detection at very low ionic strengths. This is an improvement over the prior art, where an analyte oxidation peak is not observed at low ionic strength due to large cell impedance. In the case of the disclosed sensor 58, the observed peak intensity increases with decreasing ionic strength, due to changes in analyte concentration at equilibria state with changes in competing exchangeable ion concentration.

The sensor 58 can be used for detection of various analytes. Especially preferred analytes for detecting and/or measuring with this sensor are nitrates and/or ions of lead, cadmium, and/or copper. In one embodiment, the sensor 58 can be used as part of the voltammetry system and in the baseline reference correction method described below. In another embodiment, the sensor 58 can be used in other devices, and particularly in electrochemical sensor systems. Preferred such systems generally comprise precision microcontroller, a multiplexer array, temperature detector electronics, and a data acquisition system. Additionally, two or more of sensors 58 can be used in the same system, depending on the user's needs.

In one embodiment, the sensor system comprises a sensing platform for a continuous water resource monitoring by electrochemical detection and solution parameter correction. Continuous monitoring can be provided for drinking water, fresh water, wastewater, and water produced by reverse osmosis. This device may be used as a standalone sensor in environments where the water parameters (pH temperature, ionic strength) are controlled, or in concert with compensation sensors where water parameters are not controlled. Compensation sensors may include electrical conductivity, temperature, pH, oxidation reduction potential, and/or mass flow. Advantageously, the sensing system is particularly advantageous in low ionic strength environments (<100 mM).

Dynamic Electrochemical Window Adjustment Method and Voltammetry System

Electrochemical Voltammetry Sensor System

A voltammetry sensor may be used as an electrochemical sensor for detecting and quantifying the presence of compounds such as chemical contaminants of interest (analytes). As the number of compounds to detect continues to increase, the methods needed to quantify minute changes in the surrounding medium grows with them. The process may begin with the need to detect lead, nitrates, cadmium, and/or copper in water using resistance changes on a carbon nanotube sensor. Although various electrochemical methodologies could be utilized, voltammetry is an especially preferred technique. These measurements may be made with a potentiostat circuit along with a 3-electrode setup. Different aspects of the system design include development of 3-electrode sensors (such as the sensor 58 described above with respect to FIG. 1(*f*)), the potentiostatic measurement platform, and methods of their use.

Figure 3:
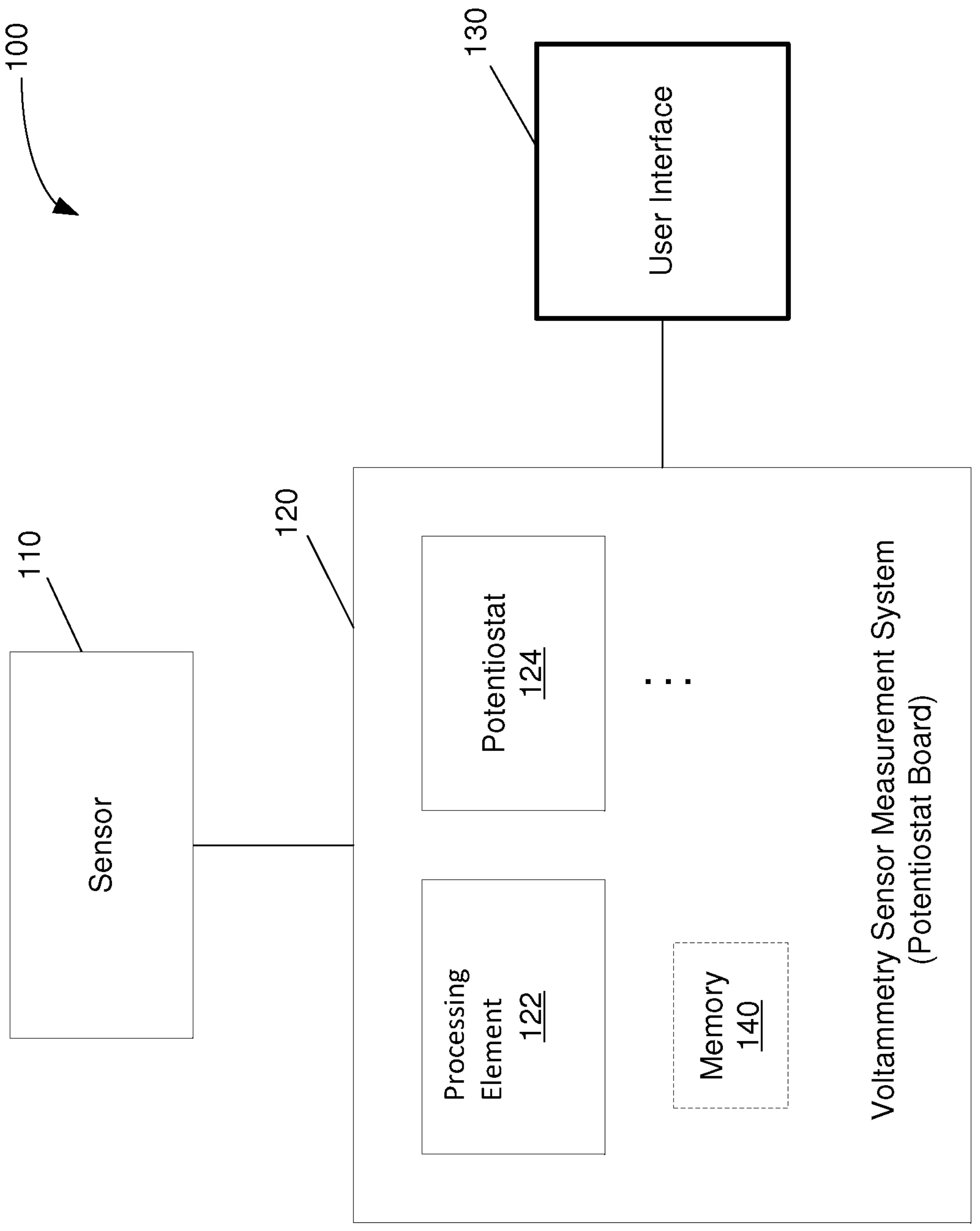
FIG. 3 is a block diagram of a voltammetry system according to an embodiment of the present invention.

This disclosure includes systems and methods of performing electrochemical measurements in aqueous operating environments to monitor analytes of interest, including hardware and software components for collecting, identifying, and transmitting environmental information. FIG. 3 is a block diagram of a voltammetry system according to an embodiment of the present invention. The voltammetry system 100 includes a sensor 110, which may be an electrochemical or a 3-electrode sensor such as the one described above, coupled to a potentiostat microcontroller combination 120 as an integrated component (IC) for performing electrochemical measurements based on electronic signal information received from the sensor 110. In one embodiment, sensor 110 is connected to microcontroller combination 120 through a multiplexer array (depicted in an exemplary configuration of FIG. 6) to prevent parasitic currents from one sensor on the array from interfering with electrochemical measurements of another sensor on the array when multiple sensors 110 are connected to the same microcontroller combination 120. The combination 120 includes a processing element 122 coupled with one or more potentiostats 124. The combination 120 is also referred to as a controller, a voltammetry or electrochemical sensor measurement system or a potentiostat board as discussed in more detail hereinbelow.

A user interface 130 is coupled with the measurement system 120, which may be done via a wireless connection. The user interface 130 generally allows the user to utilize inputs and outputs to interact with the controller 120 and is in communication with the processing element 122. Inputs may include buttons, pushbuttons, knobs, jog dials, shuttle dials, directional pads, multidirectional buttons, switches, keypads, keyboards, mice, joysticks, microphones, or the like, or combinations thereof. The outputs of the present invention include a display but may include any number of additional outputs, such as audio speakers, lights, dials, meters, printers, or the like, or combinations thereof, without departing from the scope of the present invention.

The processing element 122 in the measurement system 120 may have sufficient memory such as addressable memory to perform the processes of control and I/O (input/output) with the sensor 110 and user interface 130. The processing element 122 may include processors, microprocessors (single-core and multi-core), microcontrollers, DSPs, field-programmable gate arrays (FPGAs), analog and/or digital application-specific integrated circuits (ASICs), or the like, or combinations thereof. The processing element 122 may generally execute, process, or run instructions, code, code segments, software, firmware, programs, applications, apps, processes, services, daemons, or the like. The processing element 122 may also include hardware components such as finite-state machines, sequential and combinational logic, and other electronic circuits that can perform the functions necessary for the operation of the current invention. The processing element 122 may be in communication with the other electronic components through serial or parallel links that include address busses, data busses, control lines, and the like.

If additional memory is needed or desired, a memory 140 may be added to the measurement system 120. The memory element 140 may include data storage components, such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element 140 may be embedded in, or packaged in the same package as, the processing element 122. The memory element 140 may include, or may constitute, a "computer-readable medium". The memory element 140 may store the instructions, code, code segments, software, firmware, programs, applications, apps, services, daemons, or the like that are executed by the processing element 122.

The sensor includes a working electrode, a counter electrode, and a reference electrode for making measurements of the sample by applying a known signal to the working electrode and measuring the response with the potentiostat. In most cases, a potential is applied between the working and reference electrodes, and the current is measured between the working and counter electrodes. Alternatively, a drive current may be applied between the working and counter electrodes and a potential is measured between the working and reference electrodes.

Figure 4:
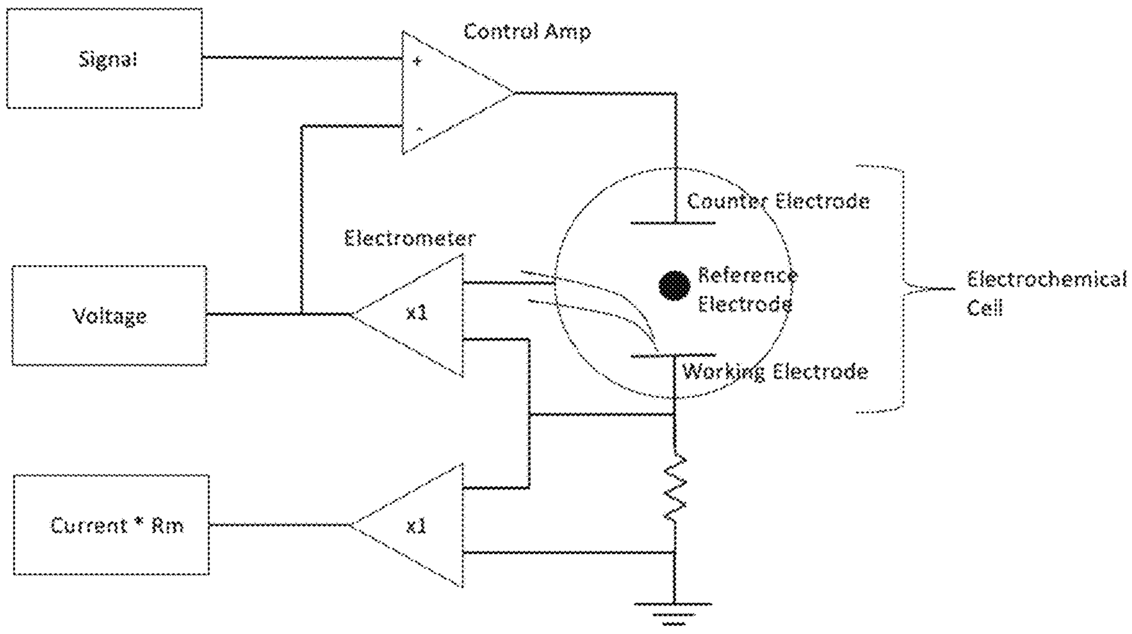
FIG. 4 shows an example of a simplified potentiostat equivalent circuit.

FIG. 4 shows an example of a simplified potentiostat circuitry that could be used as potentiostat 124, with it being designed to maintain potential changes between the working and reference electrodes of the 3-electrode sensor while measuring the current response between the working and counter electrodes. As shown, the "x1" on the amplifier indicates that the amplifier is a unity-gain differential amplifier. The output voltage of this circuit is the difference between its two inputs. The blocks labeled "Voltage" and "Current*Rm" are the voltage and current signals that are sent to the system A/D converters for digitization. The electrometer circuit measures the voltage difference between the reference and working electrodes (shown as 48 and 54, respectively, in FIG. 1). The I/E converter measures the cell current and forces the cell current to flow through a current-measurement resistor, Rm. The voltage drop across Rm is a measure of the cell current. The control amplifier compares the measured cell voltage with the desired voltage and drives current into the cell to force the voltages to be the same. The signal circuit is a computer-controlled voltage source that is generally the output of a digital-to-analog (D/A) converter that converts computer generated numbers into voltages. It will be appreciated that this is just one example, and the complexity of the potentiostat circuit may be changed without departing from the scope of the present invention. Hardware may be identified and designed to be able to implement a more complex version of the simplified potentiostat along with being able to relay the information into a human interpretable format without departing from the scope of the present invention.

As a possible embodiment of the voltammetry system controller 120 of FIG. 3, a computer device may comprise hardware elements including a processing unit with one or more processors, one or more input devices, and one or more output devices. Input to the computer system may be provided by analog-to-digital converters to convert the measurement signals from the potentiostat 124, and any other measurement devices into digital form for storage and/or processing. Output from the computer system may be provided to digital-to-analog converters to send control signals from the computer to the electrochemical sensor 110 and any other controlled components used in other embodiments. The computer system may further include (and/or be in communication with) one or more non-transitory storage devices. Such storage devices may be configured to implement any appropriate data storage.

Figure 6:
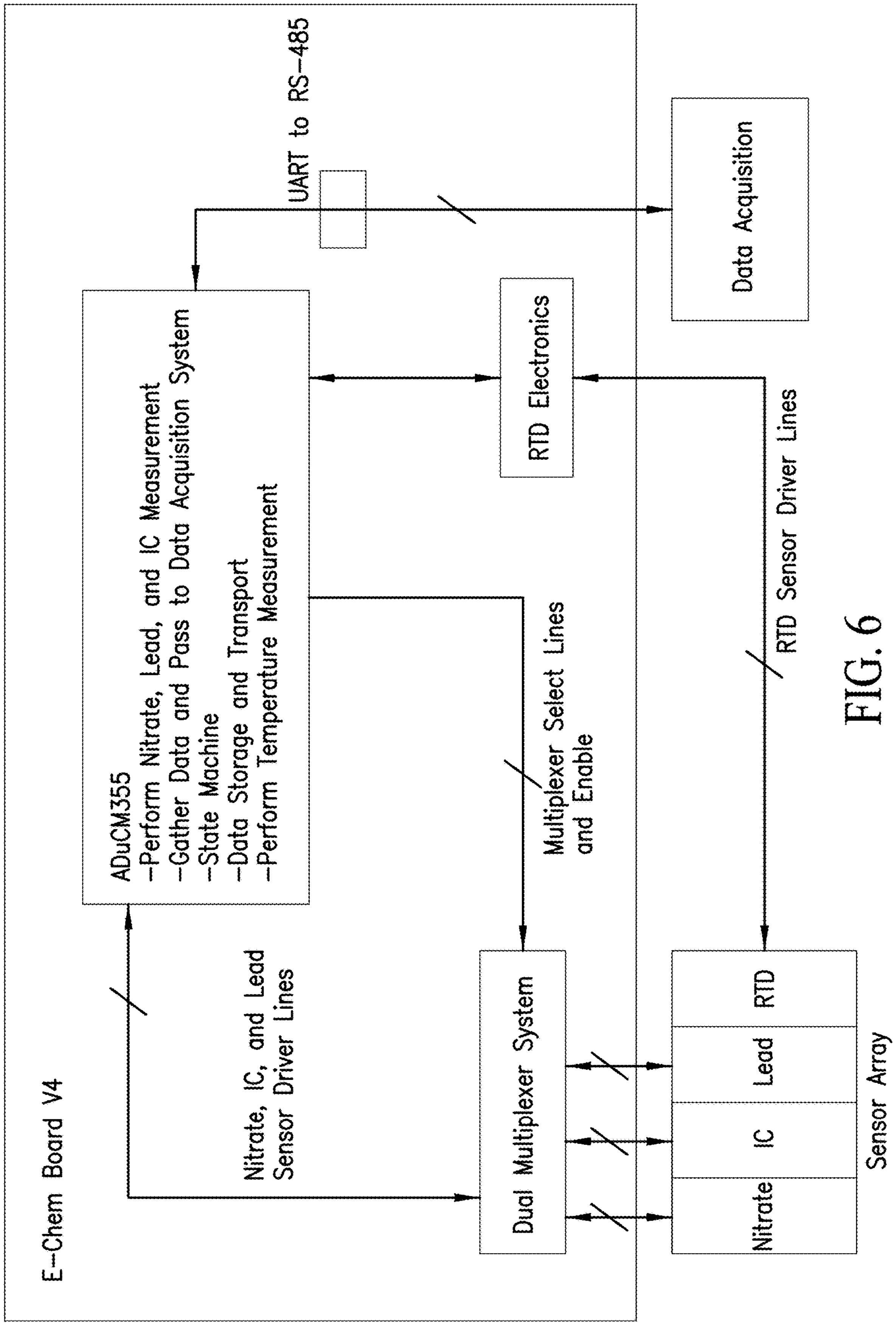
FIG. 6 is a schematic diagram of one embodiment of an electronic system for conducting voltammetry.

Turning to FIG. 6, a preferred embodiment of this system comprises a custom PCB that is based around an integrated component (IC) made by Analog Devices, such as the ADuCM355. This IC is a microcontroller and potentiostat combination that allows for traditional electrochemical techniques to be performed in a low cost, low power, minimal component package or system on chip (SoC). The ADuCM355 IC is a voltammetry system controller and may be referred to as a custom potentiostat board. The microcontroller can be used to control the driving potential for the analyte sensor, as well as to measure the sensors as necessary and send the information to the data acquisition system. The microcontroller can also accept commands from data acquisition software and to run and configure tests and pass data and system status messages. A conversion integrated circuit (IC) may be used to allow the PCB to output its serial communication to a data acquisition system. A UART to RS-485 conversion IC is preferably used to convert to the RS-485 protocol. The reliability of the RS-485 protocol is much higher than UART, which is the standard serial communication for a precision microcontroller such as the ADuCM355.

This potentiostat board may be used for performing electrochemical measurements based on known standards: linear sweep voltammetry, cyclic voltammetry (CV), square wave voltammetry (SWV), and electrochemical impedance spectroscopy (EIS). The tests are methods for quantifying the presence of analytes by applying a known signal and measuring the response on a voltammetry sensor. Firmware is developed and programmed onto the ADuCM355 to perform these measurements and output the data.

FIG. 6 depicts an exemplary schematic for an embodiment of the invention comprising the ADuCM355. The exemplary schematic includes various components for reading sensors and programming the board. FIG. 6 depicts the ADuCM355 as the main component, but in some embodiments, the system further comprises supporting components such as capacitors surrounding the ADuCM355. The system may include two outputs for connecting to sensors, EC Sensor 1 and EC Sensor 2, which interface with Chan0 and Chan 1, respectively. In this embodiment, the board has two potentiostats. In other embodiments, fewer or more potentiostats may be used. There may be an input header for programming and powering the device.

Additional sensors may be incorporated into the sensor system to compensate for environmental changes or otherwise improve analyte detection without departing from the scope of the present invention. In one embodiment, a temperature detector is used to compensate for the temperature where necessary. In one embodiment, the temperature detector is a resistive temperature detector (RTD), where the resistance of the sensor changes as the temperature changes. The microcontroller may be configured to take the measurement of the output potential of the RTD. This is a 4-point measurement where there is a constant current applied through the sensor and a differential voltage measurement taken on either side of the sensor load. In another embodiment, compensation sensors such as an ion conductivity sensor may be used.

Electrochemical Sensing

Voltammetry is one method for quantitative detection of analytes in water. In these systems, the potential is controlled and current is measured at the working electrode and the counter electrode is the conductor that completes the circuit. The working electrode and counter electrode make up one of the half cells. The other half cell is the reference electrode, which has a constant electrochemical potential, allows no current to flow through it, and is used to measure the working electrode potential. Voltammetry may be implemented in many forms that are well-understood by those having skill in the art, including, but not limited to, linear sweep voltammetry, cyclic voltammetry, and square wave voltammetry.

Square Wave Voltammetry

Figure 5:
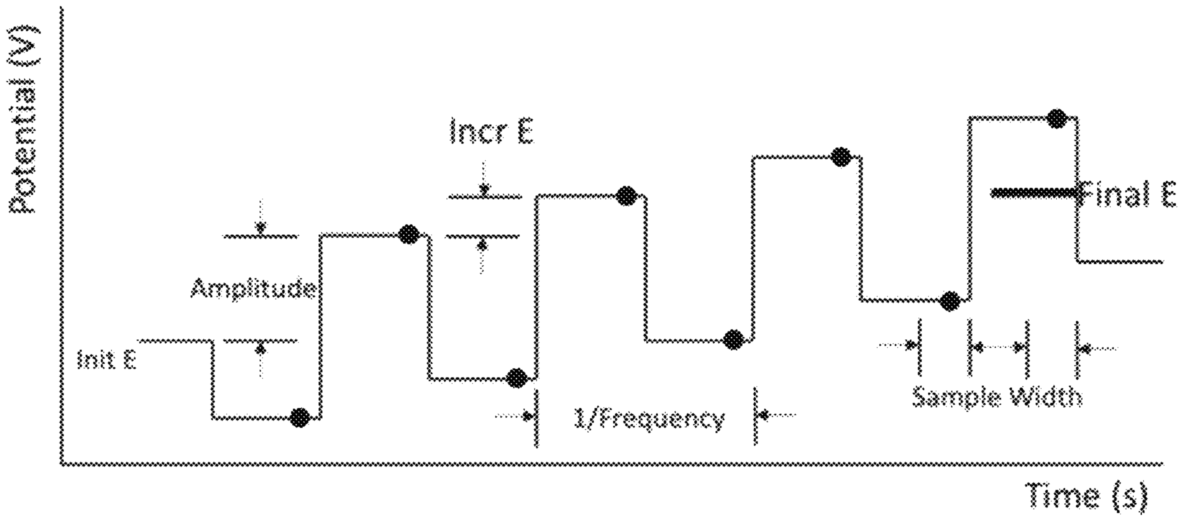
FIG. 5 shows an example of a simplified square wave voltammetry forcing function or excitation signal with measurement points.

FIG. 5 shows an example of a simplified square wave voltammetry forcing function or excitation signal with measurement points. The introduction of square wave voltammetry (SWV) is based on an understanding of square wave polarography in trace analysis. The Faradaic current is measured at a time when the double layer charging current is negligible. The output waveform on the counter electrode consists of a square wave superimposed with a DC bias increase. The resulting combined waveform develops a staircase-like output as seen in FIG. 5.

Square wave voltammetry is a form of linear potential sweep voltammetry that uses a combined square wave and staircase potential applied to an electrode. It has found numerous applications in various fields, including within medicinal and various sensing communities. In a square wave voltammetric experiment, the current at a working electrode is measured while the potential between the working electrode and a reference electrode is swept linearly in time. The potential waveform can be viewed as a superposition of a regular square wave onto an underlying staircase (see FIG. 5); in this sense, SWV can be considered a modification of staircase voltammetry. The current is sampled at two times: once at the end of the forward potential pulse and again at the end of the reverse potential pulse (in both cases immediately before the potential direction is reversed). As a result of this current sampling technique, the contribution to the current signal resulting from capacitive (sometimes referred to as non-faradaic or charging) current is minimal. As a result of having current sampling at two different instances per square-wave cycle, two current waveforms are collected. Both have diagnostic value and are therefore preserved. When viewed in isolation, the forward and reverse current waveforms mimic the appearance of a cyclic voltammogram (which corresponds to the anodic or cathodic halves but is dependent upon experimental conditions). Despite the fact that both the forward and reverse current waveforms have diagnostic worth, it is almost always the case in SWV for the potentiostat software to plot a differential current waveform derived by subtracting the reverse current waveform from the forward current waveform. This differential curve is then plotted against the applied potential.

In more detail, FIG. 5 illustrates an example of the SWV measurement methodology.

Init E=A prior known resistance of the reference resistor in Ohms

Amplitude=Measured voltage across the electrodes in Volts

1/Frequency (τ)=Measured voltage of the common bus in Volts

Pulse Width=The length of the forward portion of each cycle (for SWV, it will be the same as the reverse portion)

Sampled Period ($i_f$)=The first current measurement per step

Sampled Period ($i_r$)=The second current measurement per step

Final E=Voltage potential that is the final potential of the run.

The current response for SWV is the difference between measured values in sample period $i_f$ and $i_r$. Sampling lasts a few microseconds during each period, preferably from about 50 ms to about 150 ms, more preferably from about 70 ms to about 120 ms, even more preferably from about 90 ms to about 100 ms. The current is measured as a representative voltage through the use of a trans-impedance amplifier.

The scan rate of the measurements is determined by the step potential and the frequency as $$\frac{\text{Step } E}{\tau}$$

and defines how quickly the reaction takes place. The difference in current response is plotted as a function of the step potential to produce the voltammogram.

The double layer charging current is determined by $$e^{\left(-\frac{t}{(RC)}\right)}$$

where t is time, R is the solution resistance and, and C is the double layer capacitance. The other contributing current measurement, the Faradaic current, is determined as $$t^{-\frac{1}{2}}.$$

Based on these two responses, the double layer capacitance current decays faster than the Faradaic current. This leads to the ability to measure the Faradaic current with the double layer capacitance current having a negligible effect.

Dynamic Update of Electrochemical Window

A sensor system, such as the system 110 described above containing sensor 58/110, which is referred to in this discussion as a non-limiting example, is suitably configured to conduct a scan (e.g., square wave voltammetric scan or differential pulse voltammetric scan) over an electrochemical window defined by a start scan value and an end scan value. As discussed above, a square wave voltametric scan is a square wave superimposed on a rising staircase pattern. In FIGS. 8*a*-8*d* herein, the start scan value is to the left of the end scan value and the sensor system scans generally from left to right, left being a lower potential and right being a higher potential. This can be advantageous because the analyte peak that is of interest is typically to the left (lower potential) of an oxidation peak of the working electrode. The onset of this oxidation may be monitored by observing differential current compared to an established baseline. Through this observation, adjustments to the end scan voltage value and start scan voltage value of an electrochemical window can be adjusted to match the rate of drift and prevent the unwanted effects. Thus, by scanning generally from left to right, the sensor system's first scans the area where the analyte peak is expected and then ideally stops before reaching the oxidation peak of the working electrode. It has been observed that over time, the reference electrode can drift and can cause an established electrochemical window to no longer be valid. This shift is a result of a widening difference between the potential of the working electrode and the potential of the reference electrode. This drift forces an increase in the applied potential of the counter electrode. Without compensation, as this drift occurs the increased potential at the counter electrode may cause undesirable oxidation of the working electrode and thereby damage the sensor. The sensor system constructed according to embodiments of the present invention therefore suitably includes one or more systems for compensating for this drift.

The systems and methods according to embodiments of the present invention described herein determine baseline current prior to differential pulse voltammetry (e.g., square wave voltammetry) and provide information about both the state of the working electrode and the reference electrode. The systems and methods periodically update baseline current and may be used to make corrections to the deposition potential and voltammetry range adjustment. The onset of oxidation of the working electrode may be used for reference drift correction, using the electrode material as an internal standard. Baseline current can provide information as to the state of the working electrode, and data collected may be used to build a statistical model for output correction.

Referring to FIG. 3 the electronic system 100 constructed according to an embodiment of the present invention is configured to conduct, via the controller 120, the user interface 130, and/or the sensor 110, a square wave voltammetry scan according to at least a portion of an electrochemical window extending comprising a start scan voltage and an end scan voltage. The system 100 is configured to perform, via the controller 120, a dynamic electrochemical window calculator process 201 (FIG. 7) that periodically updates parameters of the electrochemical window of the system 100 using one or more of the processor(s), operating system, and/or applications of the controller 120. For example, by executing the dynamic electrochemical window calculator process 201, the controller 120 is suitably configured to change the end scan voltage value of the electrochemical window to account for drift in the reference electrode (e.g., move the end scan voltage value away from a value corresponding to the onset of the oxidation peak of the working electrode). In some cases, the system 100 may be configured to execute the dynamic electrochemical window calculator process 201 for updating the electrochemical window on a substantially continuous basis. In some embodiments, the system 100 may be configured to execute the dynamic electrochemical window calculator process 201 to update the electrochemical window on an ongoing-intermittent basis during operation of the sensor 110. In many cases the drift of the reference electrode may be relatively slow and perhaps even somewhat predictable. Thus, in some embodiments, the system 100 is configured to execute the process 201 to update the electrochemical window at an interval of only once per hour, or once per day, or once per week, or even longer. In some cases, it may not be necessary to conduct an initial reference scan. For example, the initial values for the baseline current, voltage of significance value, start scan value, and end scan value are suitably stored in the electronic system based on empirical knowledge of the sensor.

Figure 8A:
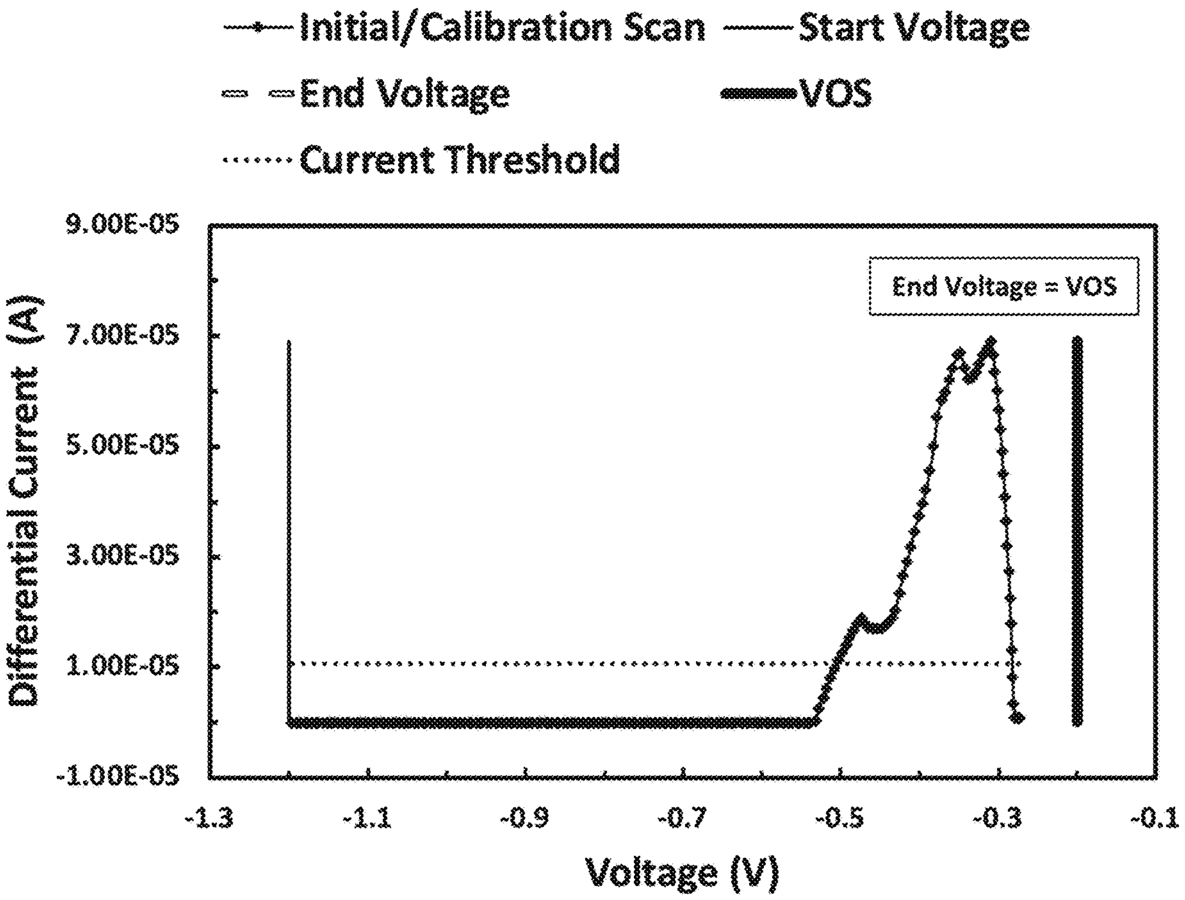
FIG. 8*a* is an example of an initial reference scan and electrochemical window, voltage of significance, and trigger voltage.

Referring to step 202, an initial baseline differential current is requested prior to voltametric analysis. For example, the request may be made via the user interface 130, such as to calibrate the sensor 110 prior to testing. Alternatively or additionally, the controller 120 may be configured to automatically trigger the process after a preset and/or selected time period or for initial calibration prior to testing. The processing element 122 may be configured to retrieve a first differential pulse voltametric (e.g., square wave voltametric) voltage waveform from the memory 140. The first voltage waveform may be based upon a preset electrochemical window and/or prior electrochemical window adjustment. The first voltage waveform is suitably based on an electrochemical window for an initial reference scan in which the end scan voltage is selected so the scan includes the oxidation peak of the working electrode (FIG. 8*a*).

The system 100 suitably determines baseline current using the initial reference scan by applying the first voltage waveform to the sensor 110. In some embodiments, this step may include performing an initial reference scan (FIG. 8*a*) before measurements begin (e.g., with no deposition time) to establish a clean current baseline with no analyte peak expressed. The differential current typically remains substantially constant during the initial reference scan up to a point where the current begins to rise due to oxidation of the working electrode of the sensor 110. The controller 120 is suitably configured to detect this substantially constant current portion of the initial reference scan to establish the initial baseline differential current. The controller 120 is suitably also configured to obtain information at this time about the initial state of the working electrode and reference electrode. For example, the controller 120 may be configured to determine surface area changes of the working electrode 54 based on the baseline current, which the processing element 122 may be configured to use in combination with a library of collected data stored on the memory 140 to build a statistical model with physical meaning for output corrections. The initial reference scan starting potential and planned end potential may be preset based upon an understanding of the environment in which the system 100 will be deployed. Additional reference scans can be conducted in substantially the same way after a period of measurement by the sensor to obtain updated information about the sensor.

Referring again to FIG. 8*a*, the initial reference scan suitably extends through voltages that result in oxidation of the working electrode to identify the oxidation peak. Although oxidation of the working electrode is undesirable in general, a single scan results in negligible oxidation and provides valuable information in return. Referring to FIG. 8*a*, in the representative initial reference scan, the start voltage (corresponding to the start scan value) is initially set at −1.2 V, the end voltage (corresponding to the end scan value) is set to −0.2 V, and the threshold current is set to 1 μA. During the initial scan, differential current is monitored, via the controller 120, for example, as the voltage is swept (e.g., in square wave voltammetry fashion) from the start scan voltage value to the end scan voltage value. In the case of the initial scan illustrated in FIG. 8*a*, the oxidation peak of the electrode is determined to be between about −0.53 V and −0.29 V.

Figure 8B:
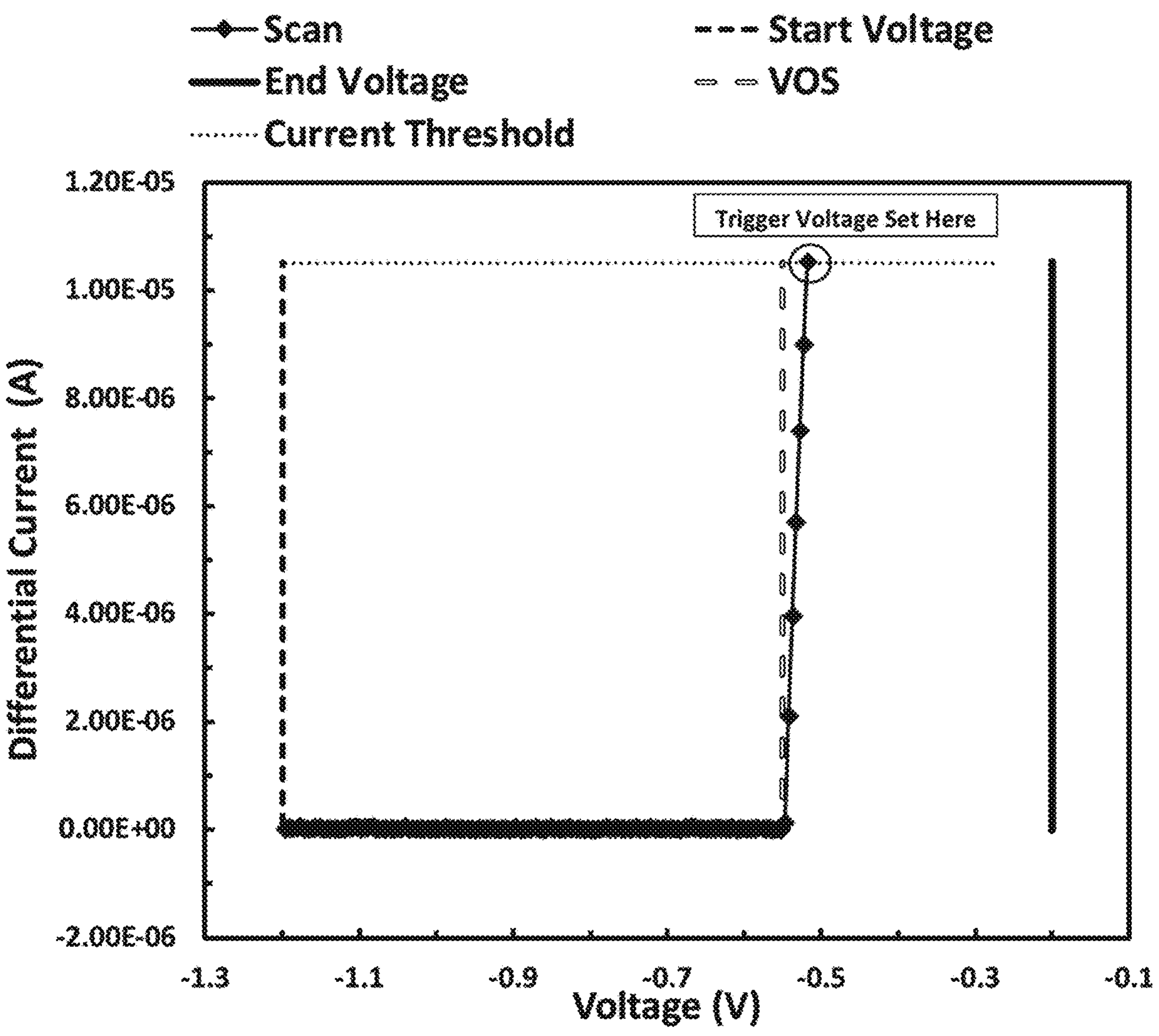
FIG. 8*b* is an example of setting the voltage of significance corresponding to where the differential current exceeds the threshold current in the initial reference scan.

Referring to FIG. 8*b*, the system 100 is suitably configured to use information from the initial reference scan to create an initial electrochemical window comprising initial start and end scan voltage values. For example, the system suitably sets a trigger voltage value equal to the voltage value that first caused the current to exceed the threshold current during the initial reference scan. The initial end scan voltage value for the first measurement scan is suitably set equal to the trigger voltage value. The initial VOS value for the first measurement scan is suitably offset from the trigger voltage value (e.g., by a user-defined and/or predetermined amount). For example, referring to FIG. 8*b*, in the representative scan, the end scan voltage value in the initial measurement scan is set, for example, at about 0.55 V to about 50 mV more negative than the point at which the differential current between the counter electrode and working electrode exceed the set threshold current of 1 μA.

Figure 7:
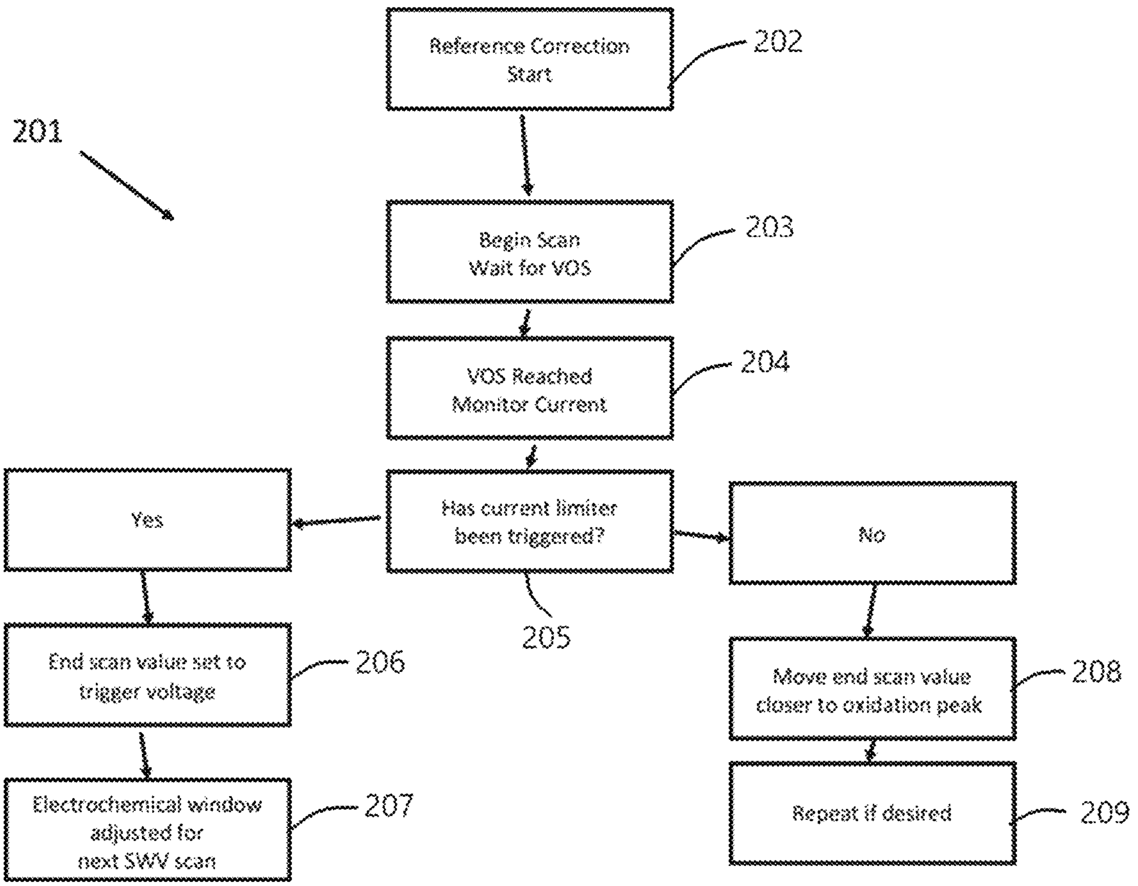
FIG. 7 is a block diagram of the dynamic electrochemical window calculator.

The flow chart of FIG. 7 depicts the steps of an exemplary method 201 of adjusting parameters, such as the electrochemical window, of an analyte testing system. In some alternative implementations, the functions noted in the various blocks may occur out of the order depicted in FIG. 7. For example, two blocks shown in succession in FIG. 7 may in fact be executed substantially concurrently, or the blocks may sometimes be executed in the reverse order depending upon the functionality involved. In addition, some steps may be optional.

The method 201 is described below, for ease of reference, as being executed by exemplary devices and components introduced with the embodiments illustrated in FIGS. 1-6. The steps of the method 201 may be performed by the controller 120, such as with the processing element 122 and/or the potentiostat 124, through the utilization of processors, transceivers, hardware, software, firmware, or combinations thereof. However, some of such actions may be distributed differently among such devices or other devices without departing from the spirit of the present invention. Control of the system may also be partially implemented with computer programs stored on one or more computer-readable medium(s). The computer-readable medium(s) may include one or more executable programs stored thereon, wherein the program(s) instruct one or more processing elements to perform all or certain of the steps outlined herein. The program(s) stored on the computer-readable medium(s) may instruct processing element(s) to perform additional, fewer, or alternative actions, including those discussed elsewhere herein.

Figure 8C:
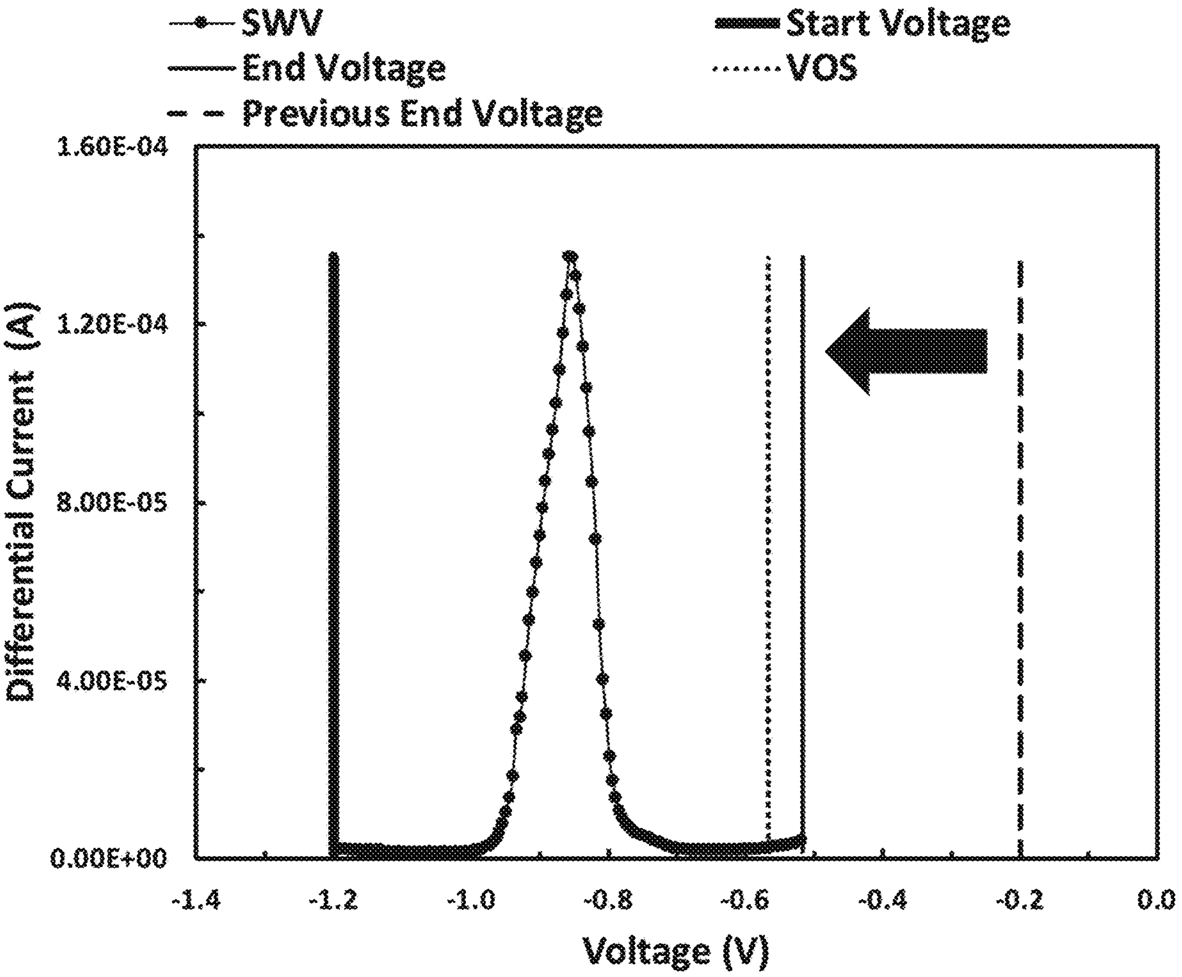
FIG. 8*c* is an example of shifting the end voltage of an SWV scan based on the VOS established in the baseline reference scan.

Referring to step 203, the system 100 suitably uses the start scan voltage value and end scan voltage value to retrieve or calculate a second differential pulse voltametric (e.g., square wave voltametric) waveform extending between the start and end scan voltage values for the initial measurement scan. The second waveform is applied to the sensor 110 (FIG. 8*c*). For example, the processing element 122 may be configured to direct the potentiostat 124 to apply the second voltage waveform. The potentiostat 124 may detect the current values corresponding to voltages of the voltage waveform, and the processing element 122 may be configured to store these values on the memory 140.

Referring to step 204, the scan is applied until a voltage of significance (VOS) is reached. The VOS may be set to be the voltage that is offset from the beginning of the oxidation peak (FIG. 8*c*). The differential current values may be detected and stored. For example, the processing element 122 may be configured to receive from the potentiostat 124 the measured differential current values corresponding to voltage levels applied to the sensor 110 according to the initial reference scan.

Referring to step 205, it is determined whether the differential current between the counter electrode and working electrode exceeds a threshold current, which can be offset above the baseline current by a user-defined amount. For example, the processing element 122 may be configured to compare the differential current values measured by the potentiostat 124 to the threshold current. Further, the processing element 122 may be suitably configured to receive a user input representative of an offset value and store the threshold current offset above the baseline current by the user-defined offset value in the memory 140. If the current rises above the threshold current after the scan has reached the VOS, but before the scan has reached the end scan voltage value, the scan is terminated to limit oxidation of the working electrode. Allowing the current to exceed the threshold current during a measurement scan before the scan has reached the VOS allows the system to fully characterize the analyte peak even if this results in high differential current. Because the system allows the differential current to exceed the threshold current until the scan has progressed to the VOS, monitoring the current before the scan has reached the VOS is optional.

Referring to step 206, if the scan is terminated due to the current rising above the threshold current between the VOS and end scan voltage value, the end scan voltage value is adjusted accordingly. For example, the processing element 122 may be configured to set or reset a trigger voltage value to equal the voltage at which the threshold current was exceeded and then set an updated end scan voltage value to be equal to or within a predetermined range of that trigger voltage value.

Referring to step 207 (FIG. 7), the dynamic electrochemical window can be updated in response to a measurement scan in which the differential current exceeds the threshold current after the scan has reached the VOS, but before it has reached the end scan voltage value. For example, the system 100 suitably sets/resets a trigger voltage value to equal the voltage that triggered the current limiter to interrupt the scan. Then the end scan voltage value is adjusted, via the controller 120, to coincide with the trigger voltage value at which the current exceeded the threshold current. Referring to FIG. 8*c*, in the representative example, in the first square wave voltammetry scan, the new VOS is offset from the new end scan value by the same amount as the difference between the old end voltage and the previous VOS. As shown in FIG. 8*c*, the end scan voltage value has changed from −0.2 V to about −0.55 V.

Figure 8D:
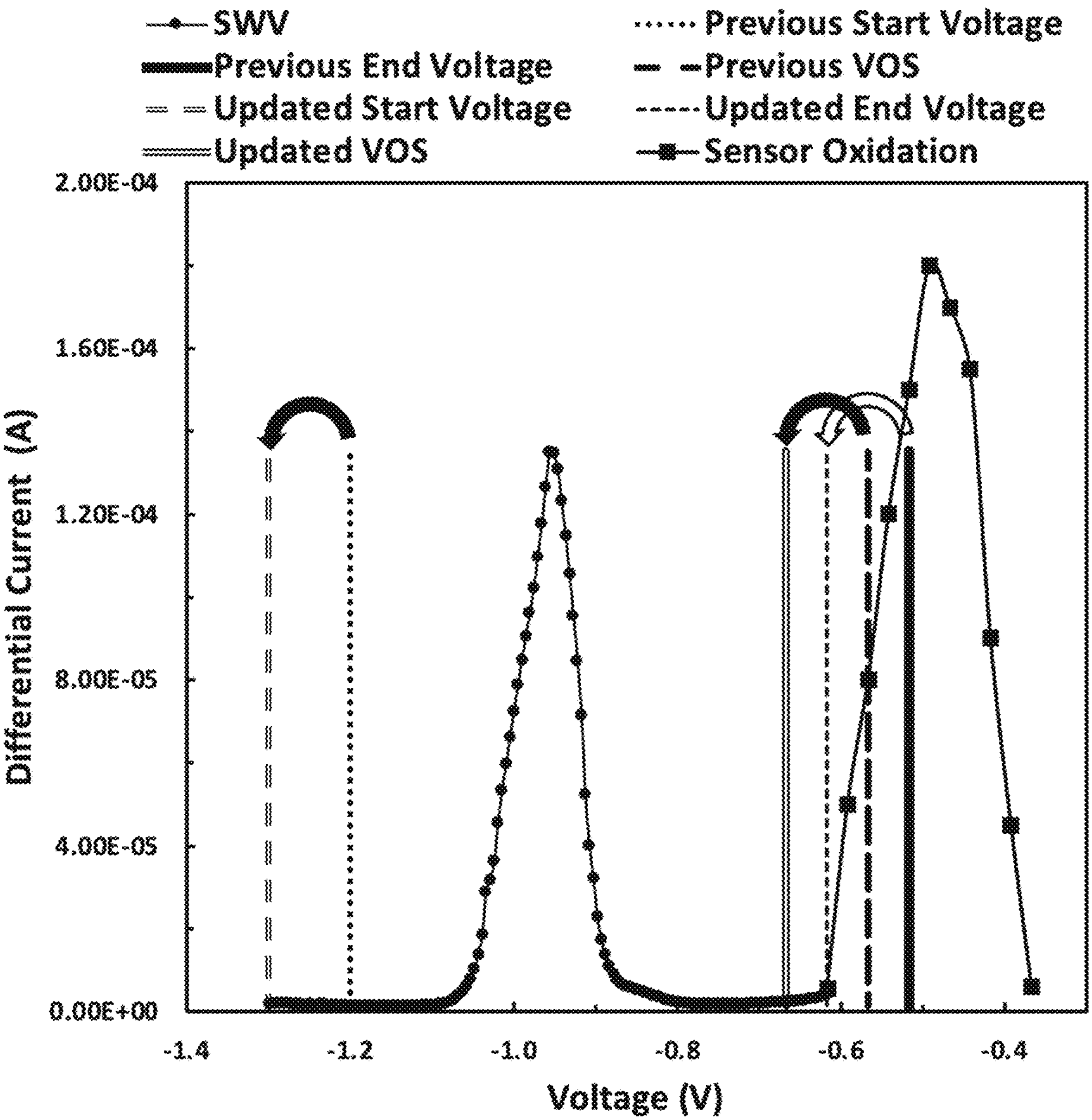
FIG. 8*d* is an example shifting the entire electrochemical window for an SWV scan after doing a subsequent reference scan.

This step 207 may include changing the start scan value a corresponding amount so it shifts the entire electrochemical window without changing its range. For example, the processing element 122 may be configured to determine the new start scan voltage value and store this value in the memory 140. Moreover, this step 207 may suitably also include changing the value of the voltage of significance (e.g., so that it remains offset from the end scan value by the same amount). For example, the processing element 122 may be configured to determine the new VOS and store the VOS in the memory 140. Thus, in the case where the current exceeds the threshold current before the end of the scan is reached, the method 201 shifts at least the end scan value, and suitably the entire electrochemical window, farther away from the oxidation peak associated with the working electrode 54. Referring to FIG. 8*d*, in the representative example, after a subsequent reference scan, the Updated VOS is about 0.1 V more negative than the Previous VOS, and so the Updated End Voltage (corresponding to the new end scan value) is about 0.1 V more negative than the Previous End Voltage (corresponding to the previous end scan value). Correspondingly, the Updated Start Voltage (corresponding to the new start scan value) is about 0.1 V more negative than the Previous Start Voltage (corresponding to the previous start scan value). In this representative example, the entire electrochemical window (both the start scan value and the end scan value) is shifted about 0.1 V more negative. As a result, the electrochemical window does not include the oxidation peak of the working electrode.

Referring to step 208, the electrochemical window may also be adjusted if the scan reaches the end scan value without causing the current to exceed the threshold current. For example, the processing element 122 may be configured to determine a new end scan value closer to the oxidation peak and store the value in the memory 140. For example, this step 208 may include suitably moving at least the end scan voltage value closer (e.g., between about 1 mV and about 10 mV, such as about 5 mV closer) to the oxidation peak associated with the working electrode. This step 208 may suitably also include moving the voltage of significance and start scan voltage value a corresponding amount to shift the entire electrochemical window closer to the oxidation peak of the working electrode.

Referring to step 209, this process can be repeated until the current exceeds the threshold current, at which point the end scan voltage value is set equal to the value that caused the current to exceed the threshold current, as described above. In this case, the start scan voltage value may also be shifted in an amount corresponding to the shift of the end scan value so that the electrochemical window remains the same.

Collectively, the abilities of the controller 120 to shift the end scan value (e.g., the entire electrochemical window) closer to and farther from the oxidation peak associated with the working electrode allows the sensor 110 to operate over a dynamic electrochemical window that is adjusted to allow full analysis and characterization of the analyte peak with only minimal oxidation of the working electrode.

During operation of the system 100 to measure an analyte, the controller 120 may be configured to not execute method 201. Once the controller 120 has determined the electrochemical window, it is possible in some cases to conduct many repeated measurements without any updates for an extended time, especially when the drift of the reference electrode is low. Regardless of whether the dynamic electrochemical window calculator process is active during measurement, an important feature is that the system 100 allows the current to exceed the threshold current during the portion of the scan corresponding with the analyte peak. This allows full characterization and analysis of the analyte peak—in contrast to prior art sensors that strictly enforce a current threshold to protect the sensor from oxidation.

This may be used to make corrections to the deposition potential and voltammetry range adjustment. When using a sensor with bismuth on the working electrode, the onset of bismuth oxidation may be used for reference drift correction, using the electrode material as an internal standard.

The method 201 may include additional, less, or alternate steps and/or device(s), including those discussed elsewhere herein. For example, the potential window end voltage may be selected to scan over the sensor oxidation material or to stop at the onset of oxidation. This decision may be made based on the understanding the user has of the electrochemical window for the unique solution in which the sensor is deployed. For instance, the user may choose to scan a large electrochemical window to get a large view of sensor material oxidation current peak. From this information, the user can instruct, via the user interface 130, the program on an acceptable ending potential for the duration of the experiment/water monitoring. In doing so, the user is also specifying, via the user interface 130, a potential that is the voltage of significance (VOS). The purpose of the VOS is to instruct the firmware on which range of potentials to consider when monitoring for current spikes. This can help mediate unplanned current spikes and premature triggers in potential ranges outside of the sensor material oxidation potential window.

Specific Use Case for Lead Sensor

In the case of a lead sensor, baseline current is established from 5 samples taken to the positive side of the VOS. VOS is established as a −50 mV offset from the trigger voltage to allow time for a baseline to be established. The 50 mV space is also small enough to exclude unplanned current spikes that would not be caused by sensor material oxidation.

After the baseline is established, the routine will begin monitoring the current for magnitudes equal to or greater than the threshold current. The threshold current is a calculated value based on a current offset provided by the software/user. This can be specified as current but is passed to the firmware as an ADC count because some settings can change the significance of the ADC counts. These settings and their calculations are handled in the software. Next, the square wave voltammetry step is performed. This routine has a user-programmable set of parameters that will allow the user to specify deposition time, deposition potential, and the characteristics of the waveform itself. The parameters include frequency (Hz), amplitude (mV), step (mV), start and end voltage (mV) corresponding to the start scan value and end scan value, and current sensitivity with respect to the resistance of current measuring resistor (R TIA). The first step of square wave voltammetry is the accumulation process. When using sensor 58 with a silver working electrode, constant voltage (Init E) −0.7 V vs external Ag/AgCl in pH 7 solution is held on the working electrode, causing negative current from the counter to working. Here, the lead ions are adsorbed and reduced from $Pb^{2+}$ (aq) to Pb(s) on the working electrode. When plotting current measured versus time, the current should be allowed to stabilize for a certain amount of time. The longer the potential is held, the more $Pb^{2+}$ that is reduced and the higher the sensitivity of the device. In one preferred embodiment, the accumulation process is performed for a time of preferably from about 30 seconds to about 300 seconds, more preferably about 60 seconds, at a voltage of preferably from about −1.0 V to about −0.6 V, more preferably about −0.7 V. The second step in square wave voltammetry is the stripping process. In this process, the voltage on the working electrode is increased slowly to oxidize the Pb(s) to $Pb^{2+}$ (aq) off the working electrode, allowing ions to flow from the working electrode to counter electrode and generating current through the circuit. The lead oxidation peak is generated around −0.55 V. The current generated and measured from this step is the difference between the forward oxidation current and the reverse reduction current.

Thus, in one cycle of square wave voltammetry, forward current is measured when going from a more negative to a more positive voltage. The reverse current is measured when going from a more positive to a more negative voltage. The difference (forward-reverse) is determined to increase signal and filter out any capacitive current that is generated from a double layer in the sensor. This difference in current is then plotted on the y-axis against voltage on the x-axis in a line graph to generate a voltammogram with the lead oxidation peak around −0.5 V.

There are several parameters in square wave voltammetry that can be modified to produce better current signal and the most optimal voltammogram. First, the electrochemical voltage window is preferably from about −0.7 V to about −0.3 V versus AgCl in pH 7 solution. The voltage stepping increment is preferably from about 5 mV to about 25 mV, more preferably from about 15 mV to about 5 mV, and more preferably about 5 V. The frequency of the square wave is preferably from about 5 Hz to about 25 Hz, and more preferably about 5 Hz. Lower frequency allows full transport of the ions and maximum current generation. The amplitude is preferably from about 10 mV to about 50 mV, more preferably from about 15 mV to about 30 mV. Lower voltages show the redox currents produced at specific voltages during the voltage incrementing and produce a narrower/sharper current peak when entering the analyte voltage oxidation range.

The next step is the clean cycle step, where the deposited analyte that was not removed during the stripping process of the square wave voltammetry cycle is cleaned from the sensor. The user may specify a DC potential to hold for a specified amount of time. The potential is chosen to oxidize the analyte remaining on the sensor and is automated to equal the VOS used in reference correction.

A "quiet time" step is then performed to wait in between scans and to allow the analyte to redistribute within the solution and move away from the sensor. This step is performed so that a clean differential current baseline can be achieved again when doing additional reference scans.

The reference correction scan is automated based off the setup done in the initial baseline scan. It will scan the potential window without deposition and monitor for current spikes after the VOS has been exceeded. The trigger voltage is defined as the potential at which the current is equal to or greater than the threshold current. This voltage is recorded and used to establish the end voltage for the scan window. When a trigger is hit, the end voltage and VOS are adjusted appropriately, preferably adjusting the start voltage by an equal magnitude and direction.

In the case of a lead sensor, the VOS is preferably set about 50 mV more negative than the end/trigger voltage. This is subject to change depending on the solution.

This cycle, including the reference correction scan, the SWV scan, the clean cycle, and the quiet time, can be programmed to repeat. The reference correction scan and clean cycle have the options of running every cycle or skipping a certain number of cycles before running again. FIG. 7 shows a logical flow of the steps the firmware and software follow if adjustments are needed and the relationship between the two. As will be appreciated by one of ordinary skill in the art, the present invention may be embodied as an apparatus (including, for example, a system, a machine, a device, and/or the like), as a method (including, for example, a business process, and/or the like), as a computer-readable storage medium, or as any combination of the foregoing. Embodiments of the invention can be manifest in the form of methods and apparatuses for practicing those methods.

Advantageously, the sensors and methods described herein allow the detection and/or measurement of analyte(s) in water, even when those analyte(s) are present at trace levels. For example, Pb ions can be detected in water at levels as low as about 10 ppb, preferably as low as about 7.5 ppb, and more preferably as low as about 5 ppb. Cd ions can be detected in water at levels as low as about 10 ppb, preferably as low as about 5 ppb, and more preferably as low as about 3 ppb. Cu ions can be detected in water at levels as low as about 800 ppb. Nitrates can be detected in water at levels as low as about 1 ppm.

In one embodiment, two or more of Pb ions, Cd ions, Cu ions, and/or nitrates can be detected and/or measured at the noted ranges. In other embodiments, three or more or even all four can be detected and/or measured at the noted ranges.

Additional advantages of the various embodiments will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments but is not necessarily included. Thus, the present disclosure encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

EXAMPLES

The following examples set forth methods in accordance with the disclosure. It is to be understood, however, that these examples are provided by way of illustration, and nothing therein should be taken as a limitation upon the overall scope.

Example 1A

Preparation of Screen-Printable Ink Comprising PFSA/PTFE Polymer and Sodium

In this procedure, 100 grams of a dispersion of a chemically stabilized perfluorosulfonic acid ("PFSA")/polytetrafluoroethylene ("PTFE") copolymer (Nafion™ PFSA 20% Dispersions-D2021; Fuel Cell Store, College Station, Texas) was placed into a flask with an overhead agitator. The copolymer dispersion had a polymer content of 20-22% by weight in a mixture of water, alcohols, mixed ethers, and other VOCs. The starting polymer had an available acid capacity of >0.92 meq/g on a H+ polymer basis.

Next, 1 gram of the same dispersion was then diluted with 49 grams of deionized (DI) water (18.2Ω). The diluted solution was then titrated with 0.1M $NaOH/H_2O$ solution (sodium hydroxide pellets for analysis; Sigma Aldrich, St. Louis, MO). Once the pH approached 7, a wait period of 3-5 minutes was used for every added drop of $NaOH/H_2O$ to allow the neutralization complete, which converted the solution from proton form to sodium form. The titration was performed using a HI-902C2 potentiometric titrator (Hanna Instruments, Pages Industrial Park, Leighton Buzzard, Bedfordshire, UK).

Based on the titration result for 1 gram of the dispersion, the amount of $NaOH/H_2O$ solution necessary to titrate 100 grams of the dispersion was calculated and added into the original flask. The resulting dispersion was stirred for about 8-12 hours at 30° C. to complete the neutralization. Then, 80 grams of 2-methyl-1,3-propanediol (Sigma Aldrich, St. Louis, MO) was added to the neutralized dispersion, and was then stirred for another 2-4 hours to completely solubilize the dispersion. The solution was then transferred into a round glass flask and was rotor evaporated at 60° C. with vacuum, becoming increasingly viscous. The sample was tested for solids content, and rotor evaporation was stopped when the sample reached 25% by weight solids.

Example 1B

Fabrication of Lead Sensor with Bismuth Working Electrode

A gold current collector was sputtered using an Angstrom Engineering Deposition System (07665) with a ¼"-thick 99.999% pure Au target onto a ZEONEX® ZF14-188 substrate (Zeon Europe GmbH, Germany) at a rate of 2 Å/s for about 8.3 minutes using a molybdenum shadow mask for patterning to achieve a thickness of 100 nm. The patterned substrate was then plasma treated using an AST Products Inc. PS-350 plasma etcher (0.1 Torr chamber pressure, 50 sccm $O_2$ flowrate, 50 W RF power, and 30 seconds RF time). A conductive carbon material, DuPont BQ242 (DuPont, Circleville, OH), was screen printed over the gold current collector and working electrode area using a stainless-steel screen (mesh 230 cal with 0.0011" wire diameter), on an ATMA OE67 screen printer, fitted with a 70-durometer polyurethane squeegee. The squeegee speed was set to 250 mm/s, and off contact was set to 1.0 mm. Cure was done in a HIX Corporation NP-2410 IR cure oven with a belt speed of 28 inches per minute and temperature of 130° C. Reference electrode material, Sun Chemical-Gwent C2130809D5 (60:40 Ag:AgCl) (Gwent Electric Material Ltd, UK), was screen printed over the gold current collector to for the reference electrode, using a stainless-steel screen (mesh 230 cal with 0.0011" wire diameter), on an ATMA OE67 screen printer, fitted with a 70-durometer polyurethane squeegee. The squeegee speed was set to 250 mm/s, and off contact was set to 1 mm. Cure was done in a HIX Corporation NP-2410 IR cure oven with a belt speed of 28 inches per minute and temperature of 130° C. To define the working electrode area, DuPont 5018A (DuPont, Circleville, OH) was screen printed over the gold current collector using a stainless steel screen (mesh 230 cal with 0.0011" wire diameter), on an ATMA OE 67 screen printer, fitted with a 70 durometer polyurethane squeegee. The squeegee speed was set to 250 mm/s, and off contact was set to 1.0 mm. Cure was done in a Heraeus DRS 10/12 UV belt oven with two passes at a belt speed of 4.0 feet per minute. Bismuth pellets (99.999% purity) (Kurt J. Lesker Company, Jefferson Hills, PA) was E-beam deposited using Angstrom Engineering Deposition System 07665 (Angstrom Engineering Canada Kitchener, Ontario) at a rate of 2 Å/s for 16.6 minutes using a molybdenum shadow mask for patterning to achieve a thickness of 200 nm.

over the working electrode to a thickness of 200 nm using a molybdenum shadow mask and an Angstrom Engineering Deposition System (07665) and bismuth pellets with 99.999% purity.

Figure 9:
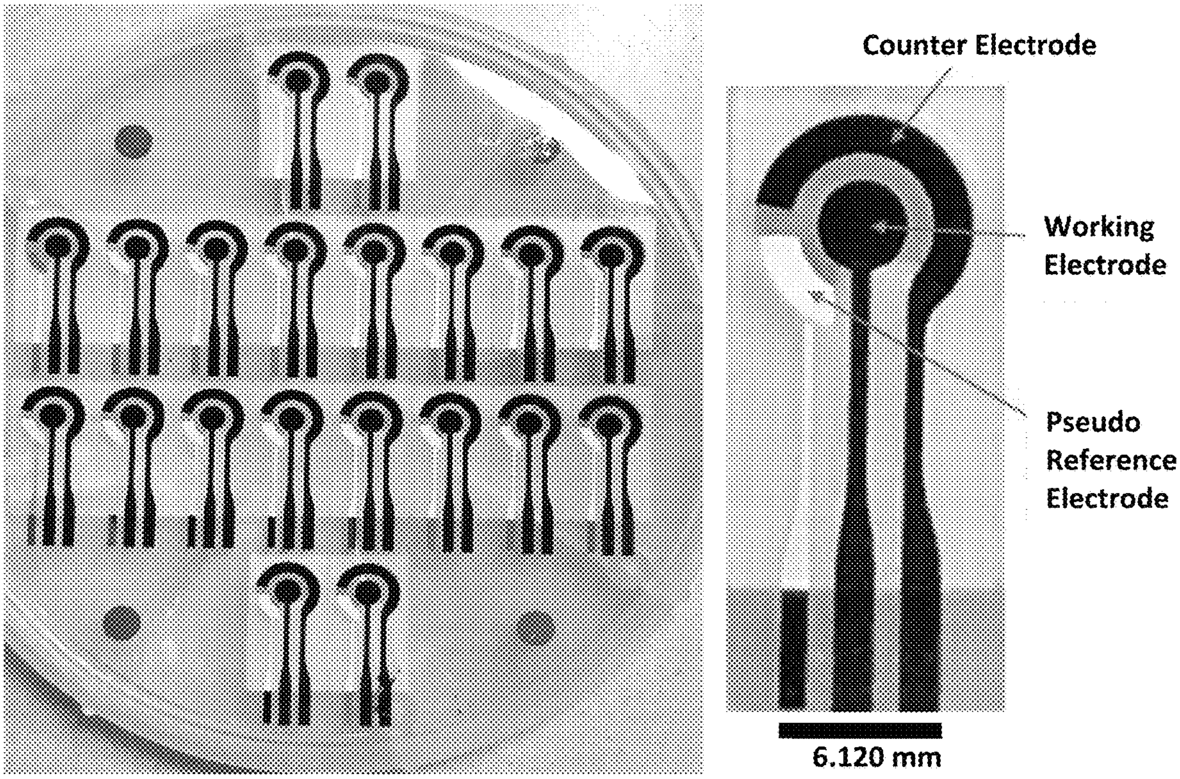
FIG. 9 is a photograph of sensors prepared as described in Example 1B.

The material formulated as described in Example 1A above was stencil coated over all of the working, counter, and reference electrodes with a 175-µm-thick stencil using the following parameters: Squeegee/Flood bar angle set to 10 degrees, flood bar stop at 360 mm, squeegee stop at 550 mm, squeegee height of 11 mm, flood bar height of 10 mm, print head speed of 150 mm/s for both squeegee and flood bar, squeegee pressure 35 kgf, floodbar Pressure of 3 kgf, 1.0 mm off print contact, and dwell time=0.1 second. The Nafion™-Na layer was then baked at 120° C. for 5 minutes in the HIX oven. FIG. 9 is a photograph of the sensors formed herein, with the sensor dimensions as shown in FIG. 2.

Example 2

Sensing of Lead in Synthetic Natural Water

A synthetic water solution was prepared, using the ion concentrations shown in Table 1, with addition of 40 mM HEPES buffer at pH 7, and lead chloride to give a $Pb^{2+}$ concentration of 100 ppb. The chemicals used for solutions were all obtained from Sigma-Aldrich (St. Louis, MO) and are as follows: potassium nitrate (99.999% trace metals basis), iron (III) nitrate nonahydrate (≥99.999% trace metals basis), manganese nitrate hydrate (99.99% trace metals basis), calcium nitrate tetrahydrate (≥99.0%), magnesium nitrate hexahydrate (99.999% trace metals basis), zinc nitrate hydrate (99.999% trace metals basis), potassium fluoride (≥99.97% trace metals basis), iron (III) chloride (sublimed grade, ≥99.9% trace metals basis), manganese (II) chloride (powder and chunks, ≥99% trace metals basis), zinc chloride (99.999% trace metals basis), magnesium chloride (AnhydroBeads™, −10 mesh, 99.99% trace metals basis), calcium sulfate (≥99.99% trace metals basis), lead standard for AAS (TraceCERT, 1000 mg/L Pb from $Pb(NO_3)_2$ in 2% nitric acid), HEPES (≥99.5% (titration)), sodium hydroxide (reagent grade, ≥98%, pellets (anhydrous)).

Figure 10:
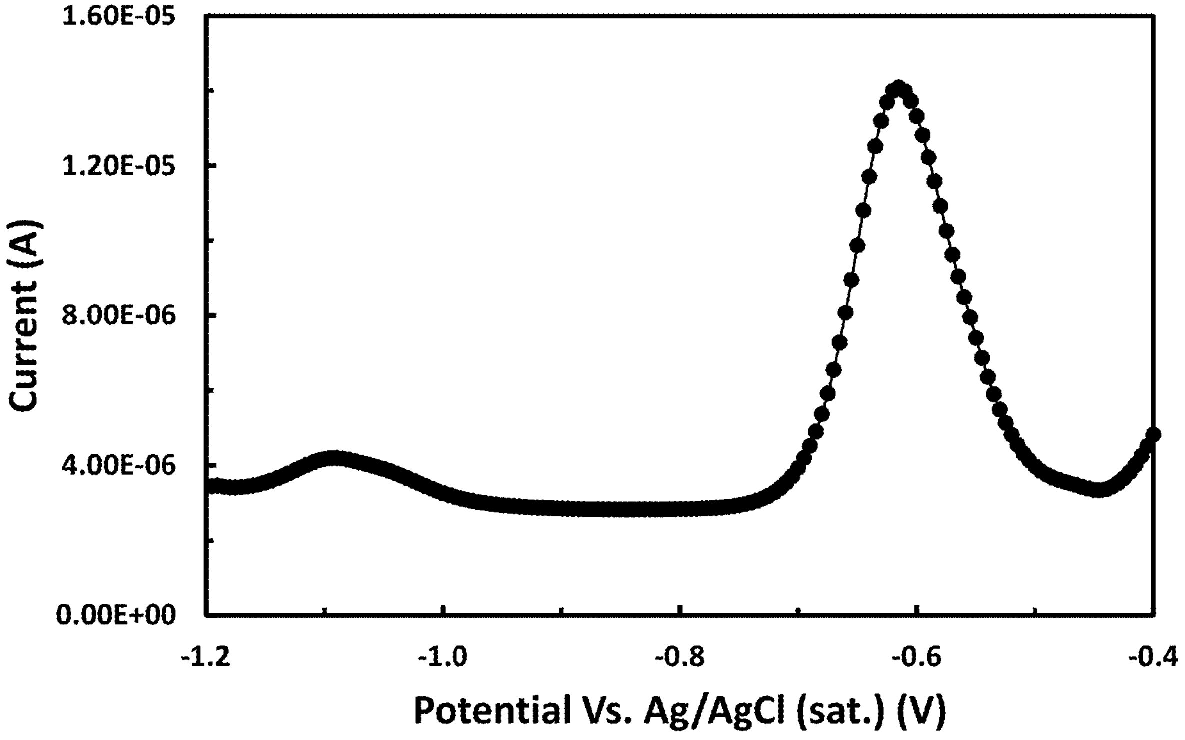
FIG. 10 is an example square wave voltammogram.
Figure 11:
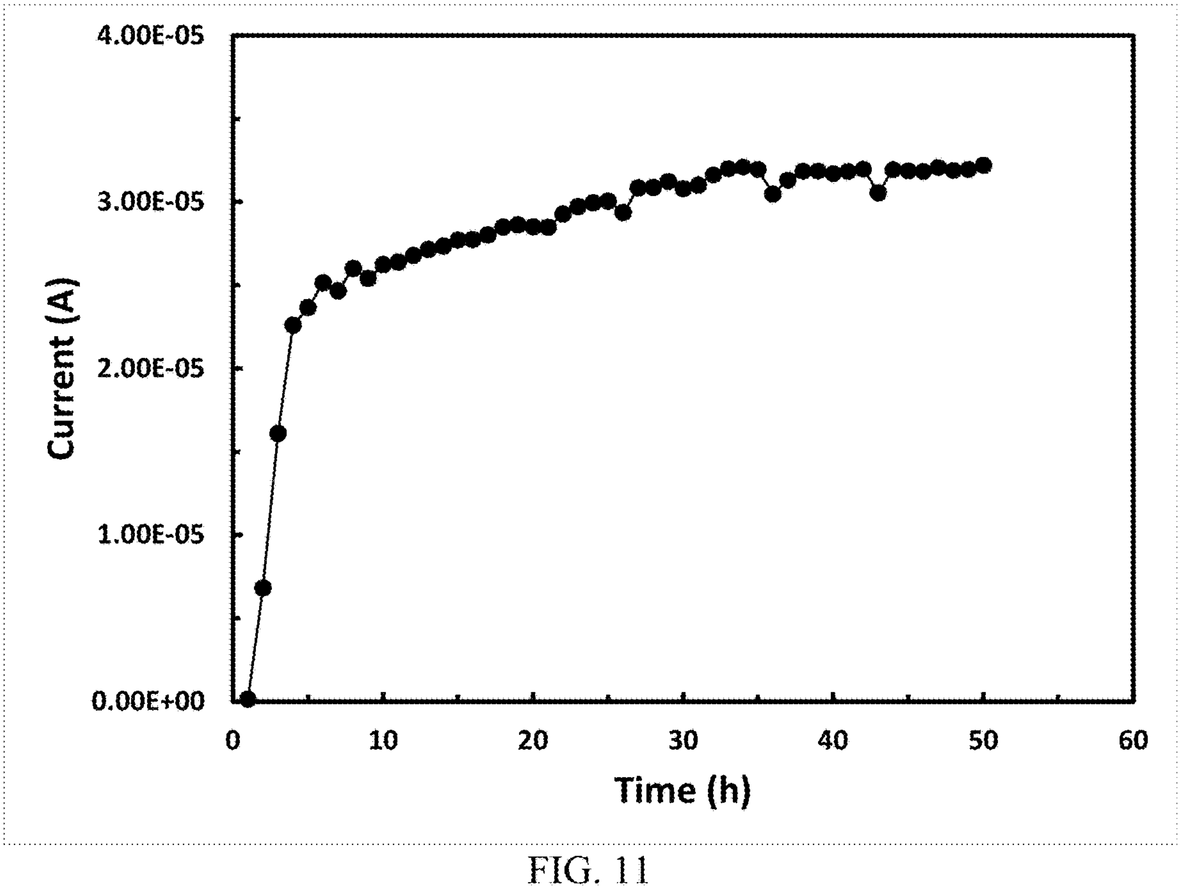
FIG. 11 is a graph showing the ion exchange equilibration in synthetic surface water containing 100 ppb $Pb^{2+}$ (Example 2).

The device prepared as described in Example 1B was submerged in the solution and square wave stripping voltammetry was performed every hour for 24 hours. The square wave stripping voltammetry parameters were as follows: Deposition potential −1.2 V vs. saturated Ag/AgCl, deposition time 300 seconds, pulse amplitude 40 mV, potential step 1 mV, frequency 5 Hz. FIG. 10 shows an example of a square wave voltammogram, and FIG. 11 shows the ion exchange equilibrium over time. The linear increase in peak current due to lead oxidation is indicative of a diffusion-limited exchange process.

TABLE 1

Synthetic Surface Water Composition

| ION | CONCENTRATION (meq/L) |
|---|---|
| Nitrate | 2.345322581 |
| Bicarbonate | 0 |
| Chloride | 1.602614729 |
| Sulfate | 1.463570685 |
| Fluoride | 0.017547368 |
| Potassium | 0.120194484 |
| Iron | 0.005989793 |
| Manganese | 0.001812261 |
| Calcium | 3.281251559 |
| Magnesium | 1.725949393 |
| Zinc | 0.294019578 |

Example 3

Sensing of Lead in Low Conductivity Water with and without Solid State Electrolyte Layer Square wave anodic stripping analysis was performed using a CHI660E electrochemical workstation coupled with CHI 684 multiplexer (CH Instruments Inc., USA). Sodium chloride, sodium hydroxide, 99.999% lead chloride and 4-(2-hydroxyethyl) piperazine-1-ethanesulfonic (HEPES) acid were purchased from Sigma-Aldrich (St. Louis, MO).

All solutions were processed in deionized water (resistivity≥18 MΩ·cm). The effects of electrical conductivities of test solutions on the respective performances of bare (i.e., uncoated) bismuth electrodes and of bismuth electrodes coated with an electrolyte layer (i.e., the modified-Nafion™ D2021 polymer layer formed as described in Example 1A) were investigated and compared. The bare bismuth electrodes were fabricated as in Example 1B except without depositing the modified-Nafion™ material over the working, counter, and reference electrodes. To control the pH of the test solutions, 10 mM HEPES buffer was prepared in DI water and titrated to pH 7 using 0.1M NaOH. Test solutions containing 100 µg/L of lead chloride in HEPES buffer with varying electrical conductivity values were prepared by adding 2M NaCl solution. The measured electrical conductivities of the test solutions were between 23 µS/cm and 1500 µS/cm, which is a typical range for environmental water, drinking water, and river water. Coated electrodes were prepared as described in Example 1B. The coated electrodes and bare bismuth electrodes (prepared as in Example 1B but not coated) were immersed in separate 20 mL electrochemical cells containing test solutions and left to equilibrate for 24 hours. After equilibration, each electrochemical cell was connected to separate multiplexer channel, and −1.2 V accumulation potential was applied for 300 seconds. Following the accumulation steps, the voltammograms were recorded by applying a positive-going square wave potential between −1.2 V and −0.5 V with a frequency 5 Hz, amplitude of 25 mV, and step potential of 5 mV.

Figure 12:
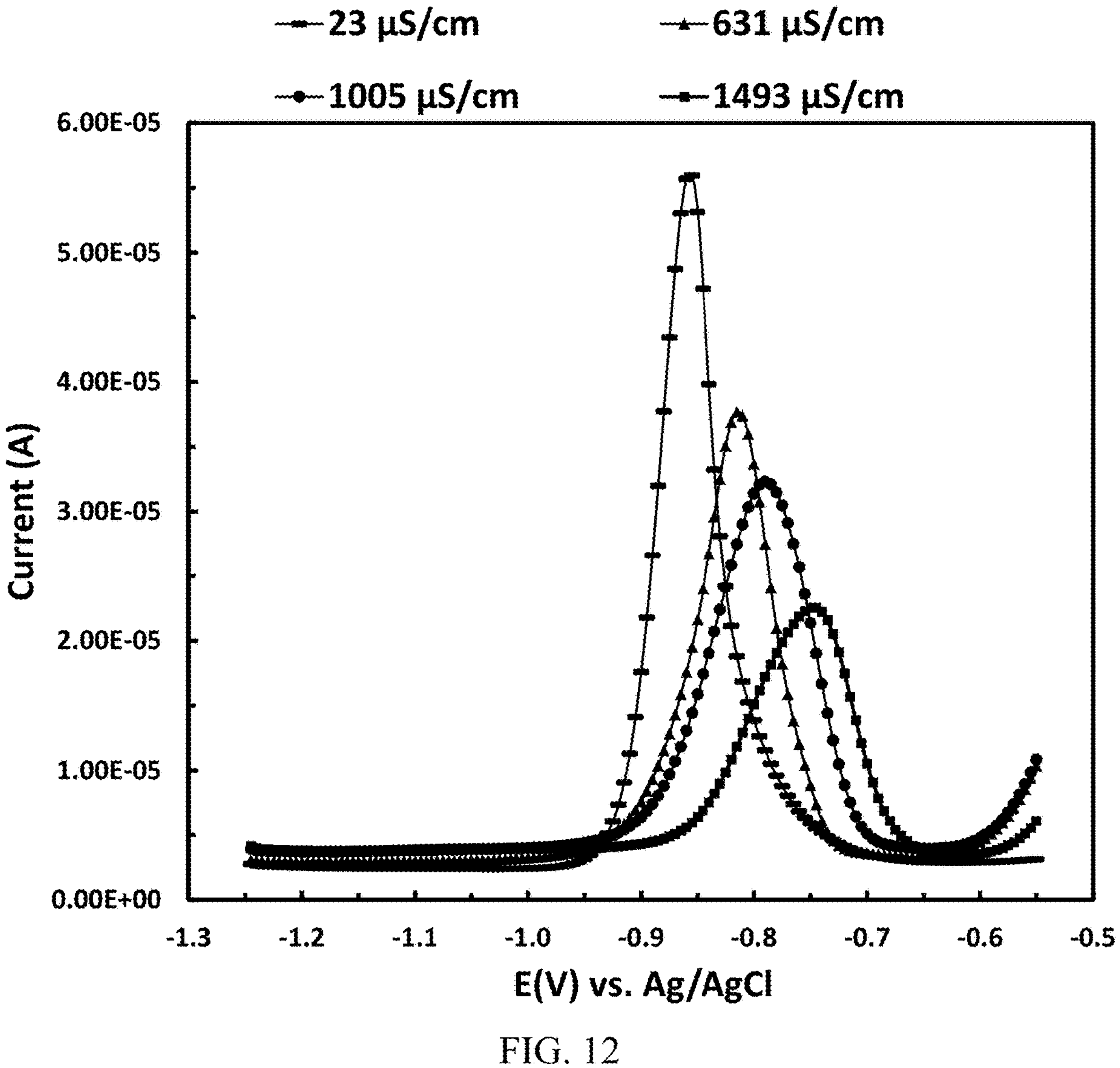
FIG. 12 provides voltammograms of coated sensors obtained as described in Example 3.

As shown FIG. 12, all voltammograms for coated sensors were sharp and very well defined. The peak current intensity had an inverse relation with electrical conductivity due to competition of the counter ions, such as sodium ion, with lead ion to adsorb in the Nafion™ membrane as shown the following equilibrium reaction.

$$2\mathrm{Na}R + \mathrm{Pb}^{2+} = \mathrm{Pb}R_2 + 2\mathrm{Na}^{+}\cdot$$

$$K_{Pb}^{2Na} = \frac{X_{Pb}a^2\mathrm{Na}}{X^2{}_{Na}.a\mathrm{Pb}},$$

where K is the exchange constant, $X_{Pb}$ is the equivalent ionic fraction of lead in the membrane, $a_{Pb}$ is the activity of free $Pb^{2+}$, $X_{Na}$ is the fraction of sodium ion in membrane, and aNa is the activity of sodium in the solution.

Figure 13:
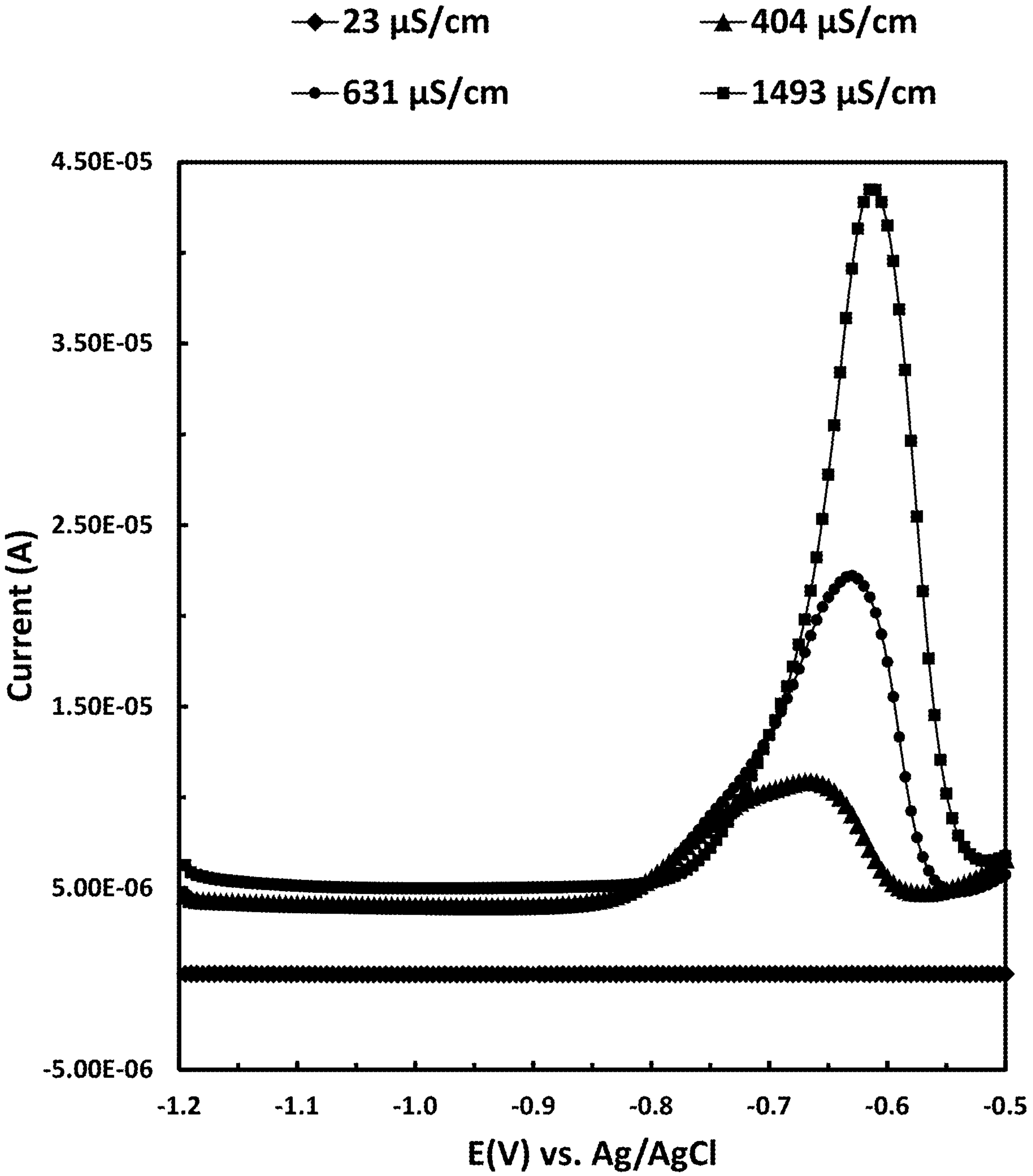
FIG. 13 provides voltammograms of uncoated sensors obtained as described in Example 3.

The above equilibrium equation suggests that the response of metal stripping analysis with the coated sensor is sensitive to the presence of other secondary ions in the water samples, and that the response is significantly enhanced when these counter ions are present at low amounts. Since the concentration of dissolved counter ions in an environmental water sample is low, the coated sensor is highly desirable for detection of metal ions in such water samples. In contrast, due to the presence of large uncompensated solution, resistance between the working and counter electrodes for a bare electrode lead ion stripping voltammogram at lower ionic strength solution were greatly diminished as shown in FIG. 13. Therefore, metal stripping analysis with bare electrodes in low ionic strength water sample requires supporting electrolytes, which limits its practical application for field measurements.

Example 4

Detection Limit in Small Volumes and Associated Ion Depletion Effects

Figure 14:
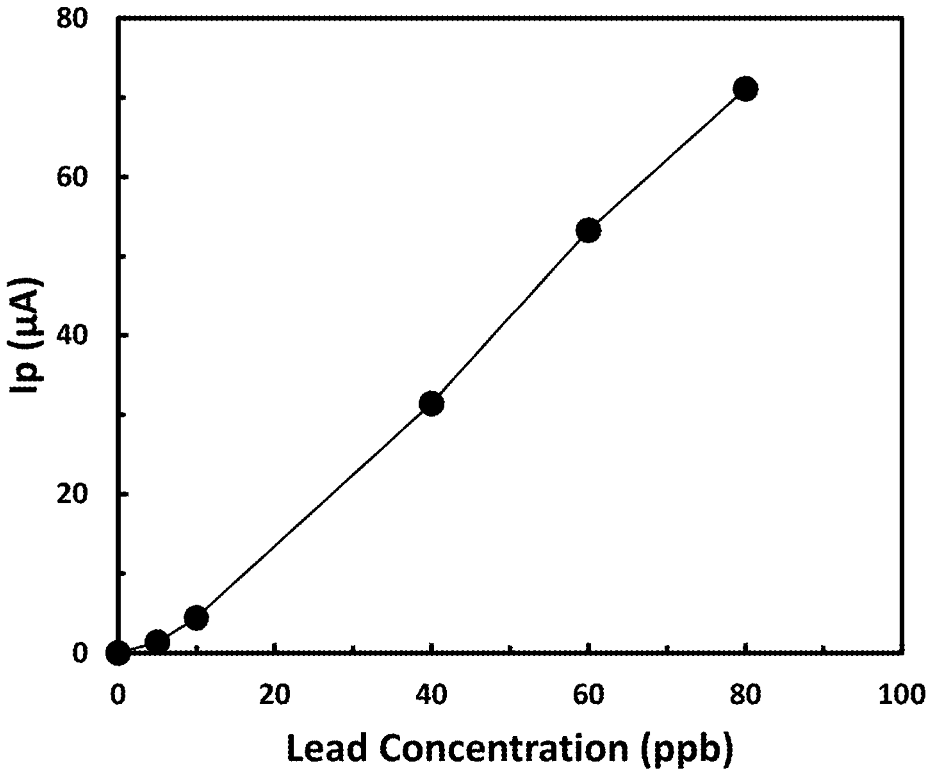
FIG. 14 shows the calibration plot for a sensor of Example 4 with a 20-mL solution volume.
Figure 15:
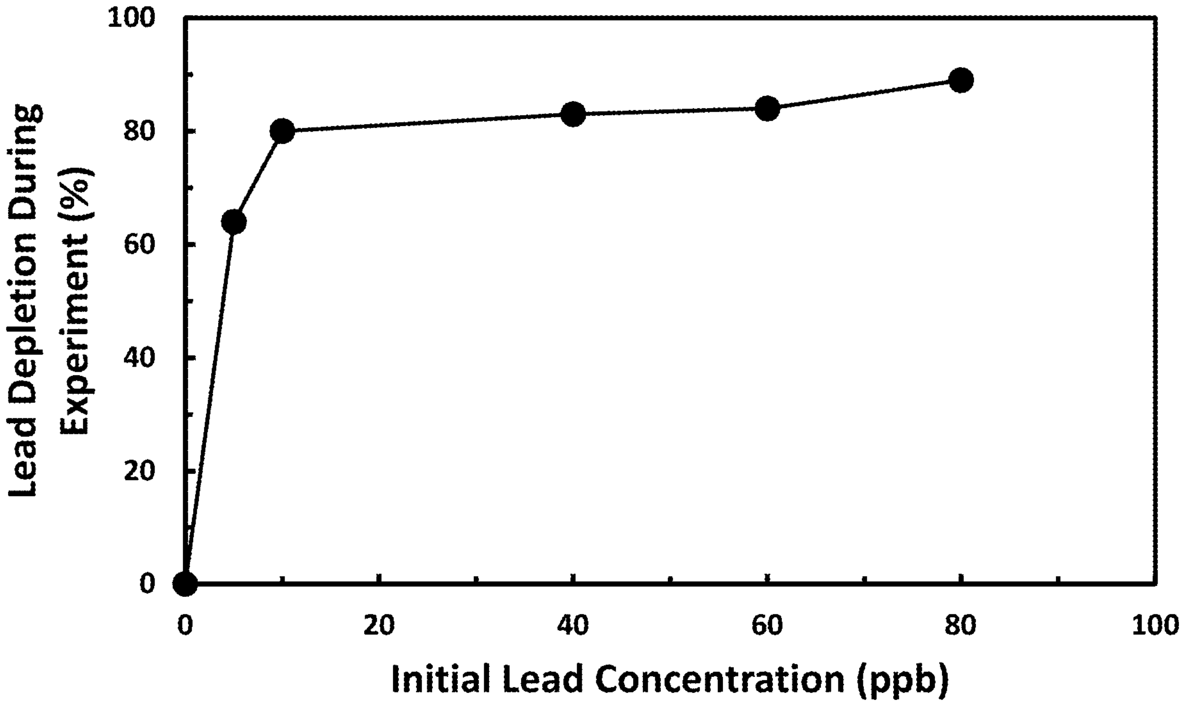
FIG. 15 is a graph of lead depletion as a function of initial lead concentration (Example 4).
Figure 16:
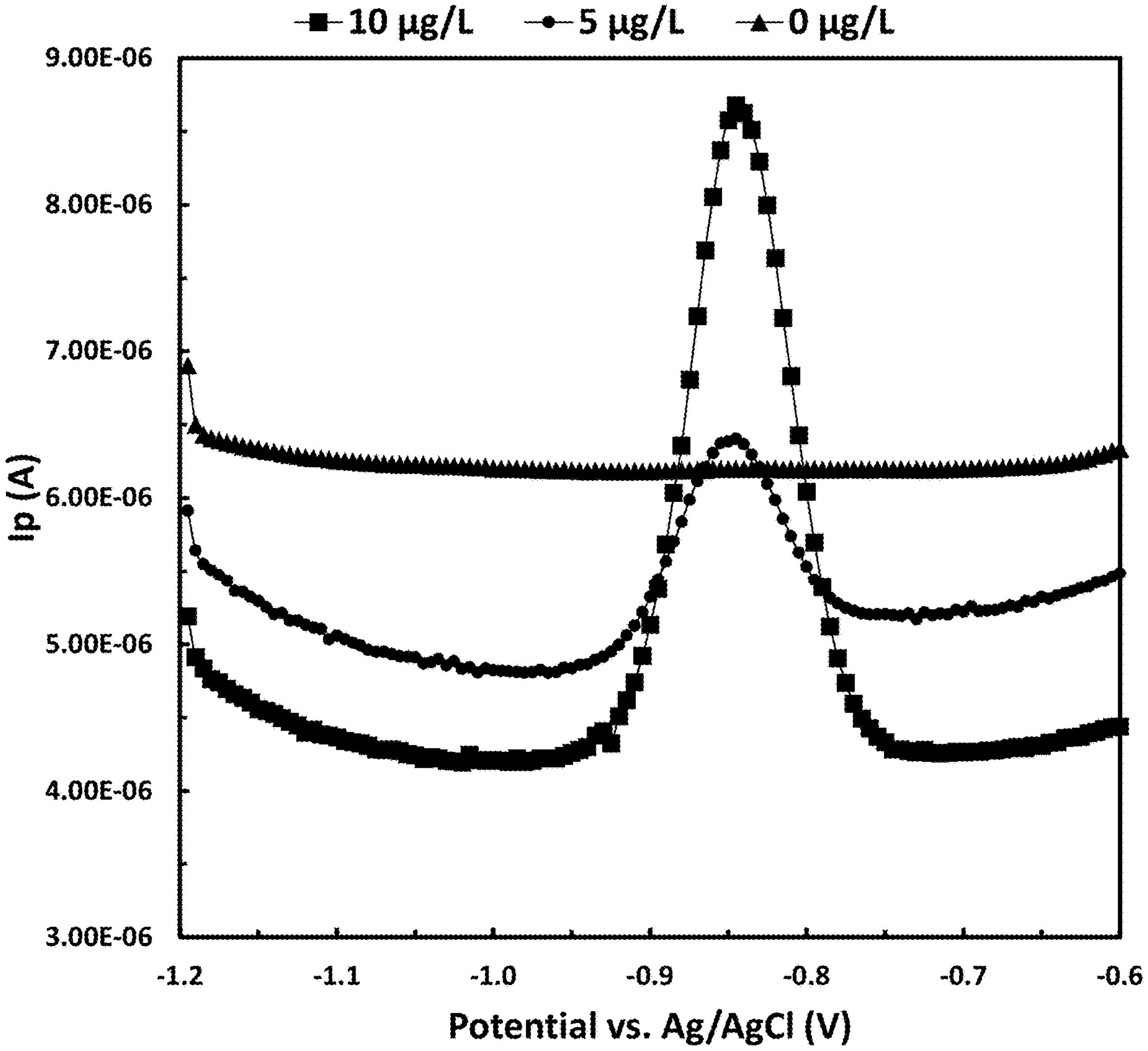
FIG. 16 provides voltammograms of solutions at 0, 5, and 10 ppb initial lead concentrations (Example 4).

Devices fabricated as described in Example 1B were submerged in deionized water containing a variable concentration of lead (II) chloride. Samples were allowed to equilibrate for 24 hours, and anodic stripping square wave voltammetry was performed. The stock solutions used for the experiments as well as the sample water post-experiment were analyzed for lead concentration by Inductively Coupled Plasma-Optical Emission Spectrometry ("ICP-OES") using a Thermo Scientific™ iCAP 7600 ICP-OES Duo (Thermo Fisher Scientific Inc., Germany). The observed peak lead oxidation current vs. lead concentration is shown in FIG. 14. The calculated lead depletion due to ion exchange of the device vs. lead concentration is given in FIG. 15. The voltammograms acquired at 0, 5, and 10 ppb initial lead concentrations are given in FIG. 16. These results indicate that the Nafion™ membrane is successful in absorbing lead, and test volume should be considered when performing a measurement.

Example 5

Lead Detection in Synthetic Water

Figure 17:
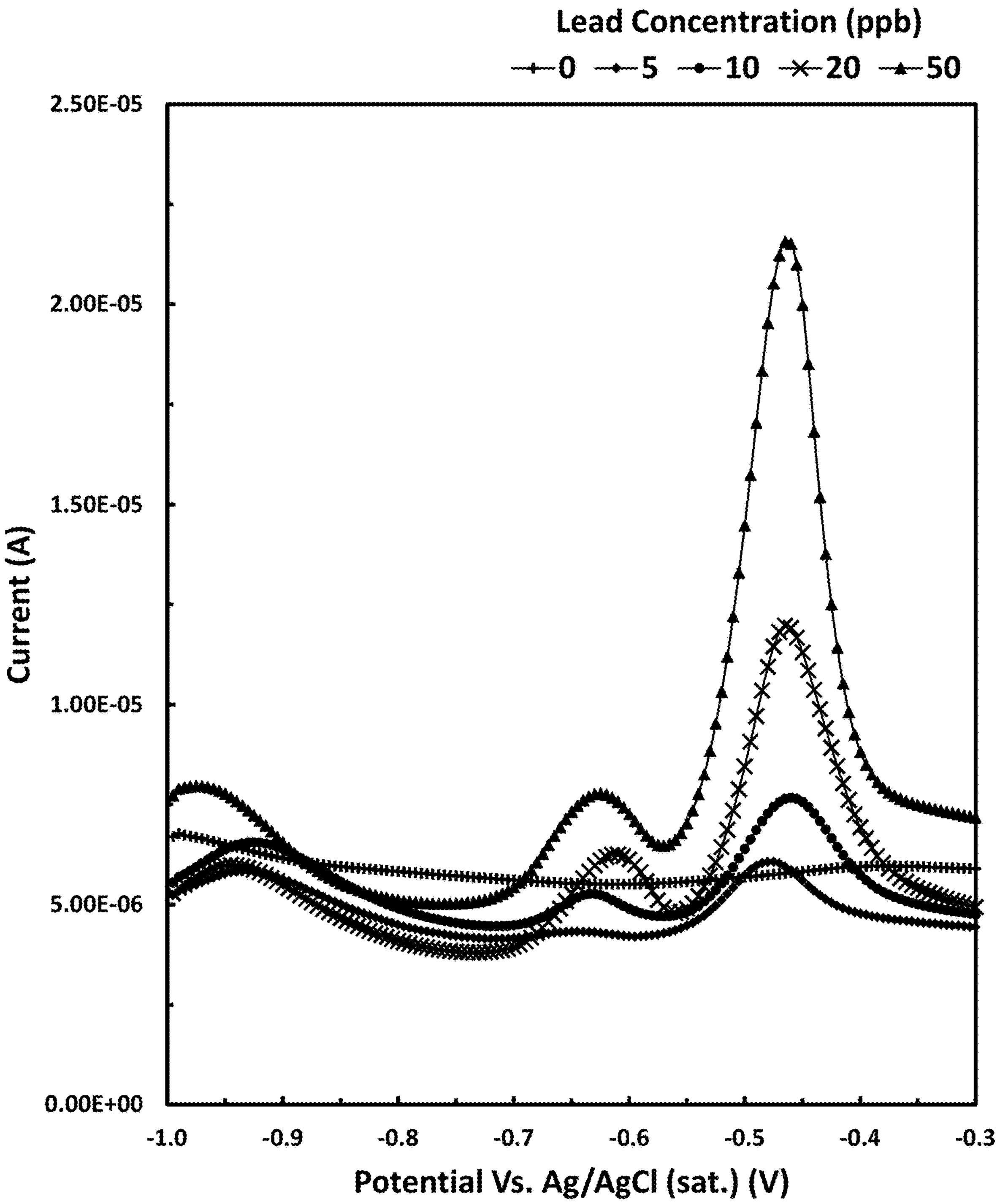
FIG. 17 provides voltammograms of solutions at various lead chloride concentrations determined as described in Example 5).

This example demonstrates lead detection in synthetic water of solid state electrodes that are coated with the Nafion™-modified polymer membrane. Standard solutions of 0, 5, 10, 20, and 50 µg/L lead nitrate were prepared in synthetic water as described in Table 1. For comparison purposes, the lead ion standards were analyzed by Thermo Scientific™ iCAP 7600 ICP-OES Duo. Coated sensors prepared as described in Example 1B were each immersed in 20 mL electrochemical cell containing each lead standard and left for 24 hours to equilibrate the membrane with the lead ion in test solution. After equilibration, each electrochemical cell was connected to a separate multiplexer channel, and stripping analysis for lead ion detection was performed in the same way as Example 4. The data in FIG. 17 clearly shows that the voltammogram recorded at all lead nitrate concentrations were well defined. The appearance of such well-resolved voltammograms suggests that there was a well-formed double layer structure on the electrode surface by the ions trapped in the ion exchange membrane.

Figure 18:
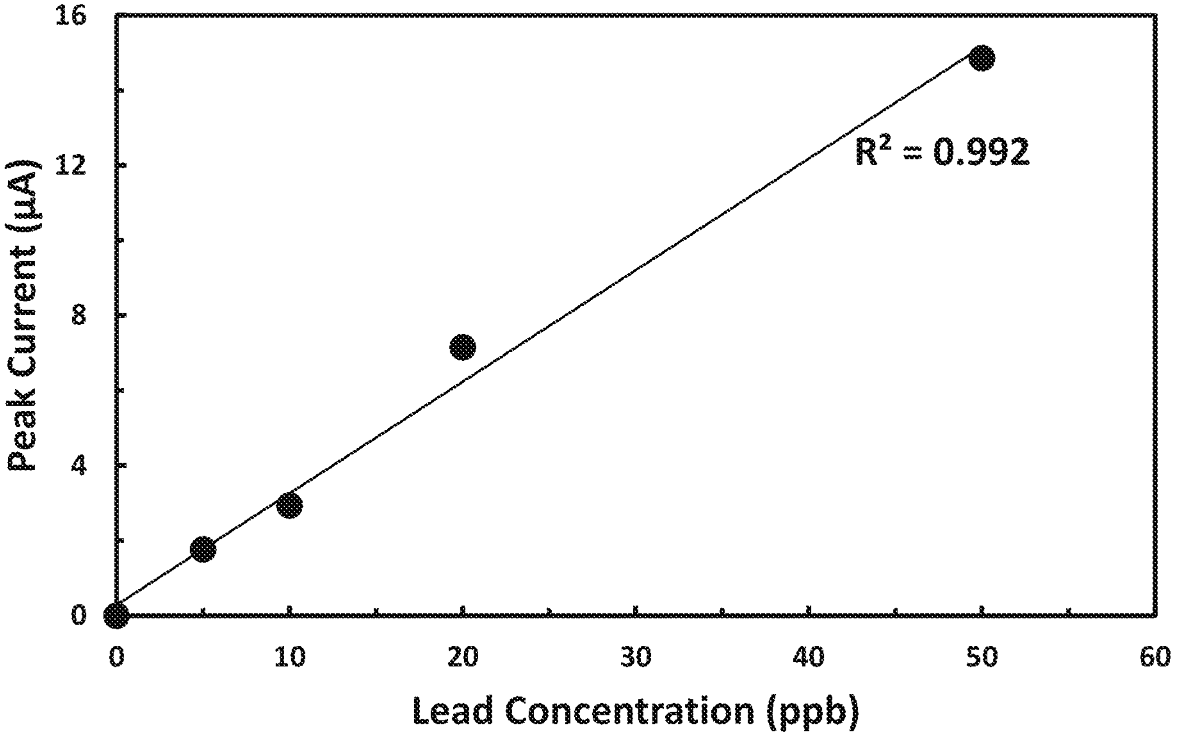
FIG. 18 is a graph of measured peak currents compared to initial lead concentrations (Example 5).
Figure 19:
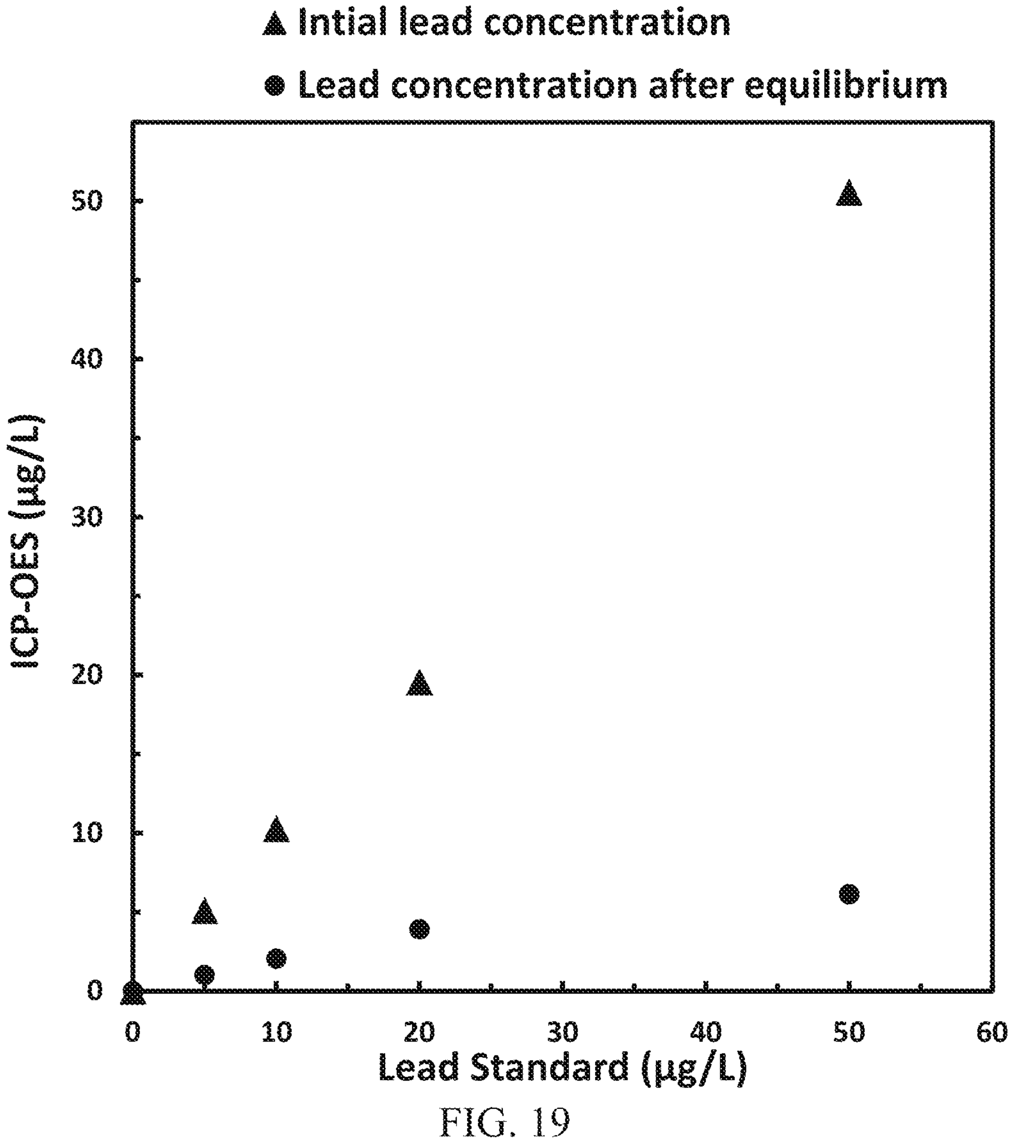
FIG. 19 is a graph showing post-experimental ICP-OES measurements of lead ion quantities extracted from the test solutions by the membrane formed from the Nafion™-modified polymer as described in Example 5.

The measured peak current and initial lead concentration showed a good level of correlation over the range of 5 µg/L to 50 µg/L ($R^2$=0.992) as shown in FIG. 18. Additionally, lead concentrations measured by ICP-OES and anodic stripping voltammetry were significantly comparable. Post-experimental ICP-OES lead ion concentration measurements indicated that significant amount of lead ion was extracted from the test solution by the membrane formed from the modified Nafion™ polymer (see FIG. 19). Therefore, that membrane played a role not only by reducing the impedance of the solution but also as a lead ion enrichment compartment that increases the sensitivity of electrochemical measurements. All the above data support that printed sensors coated with these membranes are suitable for accurate determination of lead ion concentrations from unpopulated and low ionic strength fresh water without external supporting electrolytes.

Example 6

Square Wave Voltammetry with Reference Correction Algorithm

A sensor was fabricated as described in Example 1B. This sensor was connected to the counter, working, and reference electrode connections on sensor channel 0 of the and an EVAL-AduCM355QSPZ Rev. B evaluation circuit board (Analog Devices, Norwood, MA).

A standard solution of 100 ppb $Pb^{2+}$ in deionized water was made by adding 0.1 mL of 1,000 ppm lead standard to a 1-L volumetric flask and filled with deionized water. The sensor was immersed in the standard solution.

Figure 20:
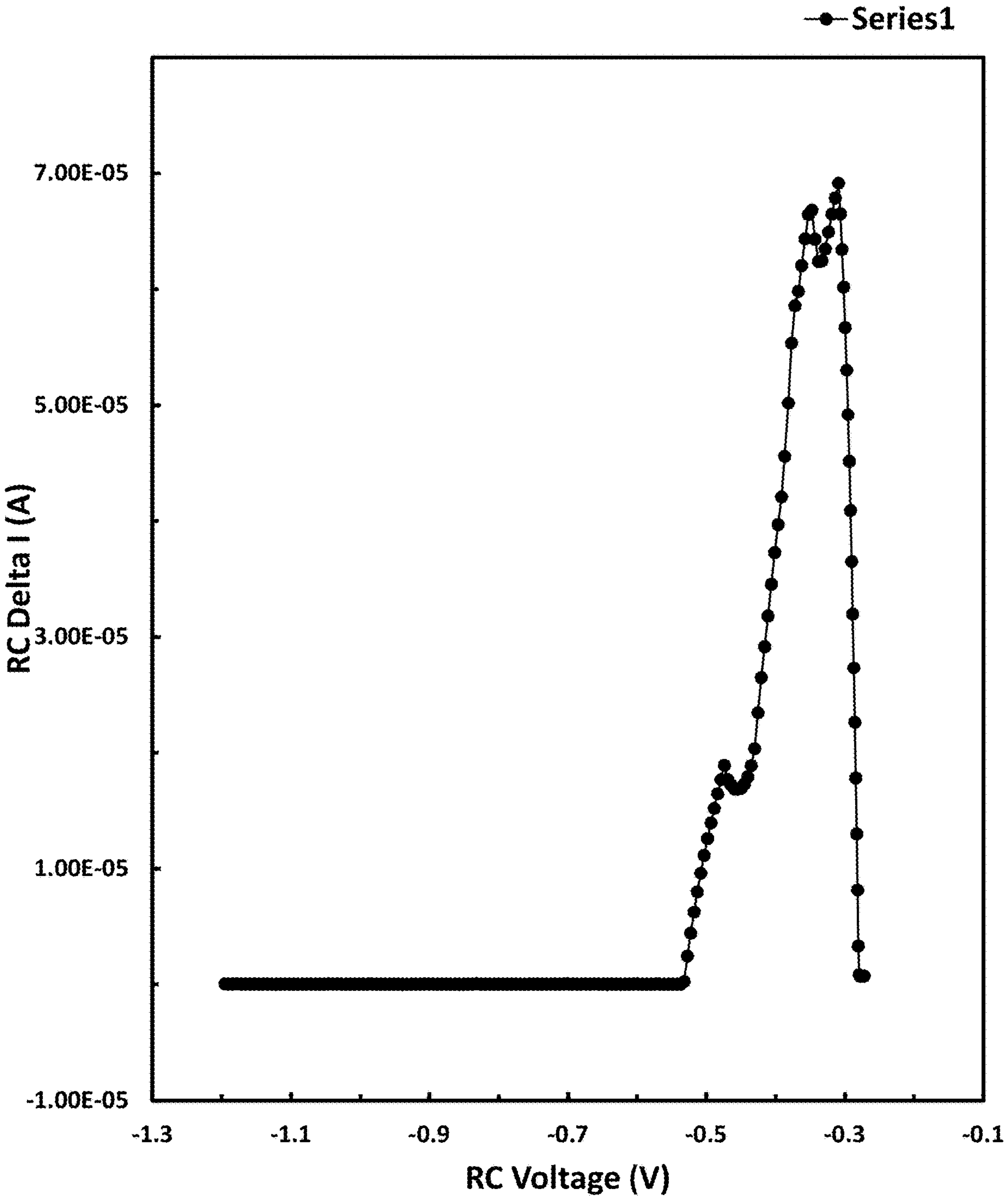
FIG. 20 is a graph showing the initial scan carried out in Example 6 to identify oxidation of the sensor material and establish the voltage of significance.

An initial scan was run with zero deposition time to get a clear picture of the electrochemical window. This scan was carried out by starting at approximately −1.2 V and ending at approximately −0.2 V. This range was determined to be sufficient to capture the oxidation of the sensor material. As shown in FIG. 20, a clean baseline was observed, with the large peak representing oxidation of the sensor material. The voltage of significance ("VOS") was set based on this result, and the reference correction auto generated the trigger voltage and adjusted the end voltage accordingly.

Figure 21:
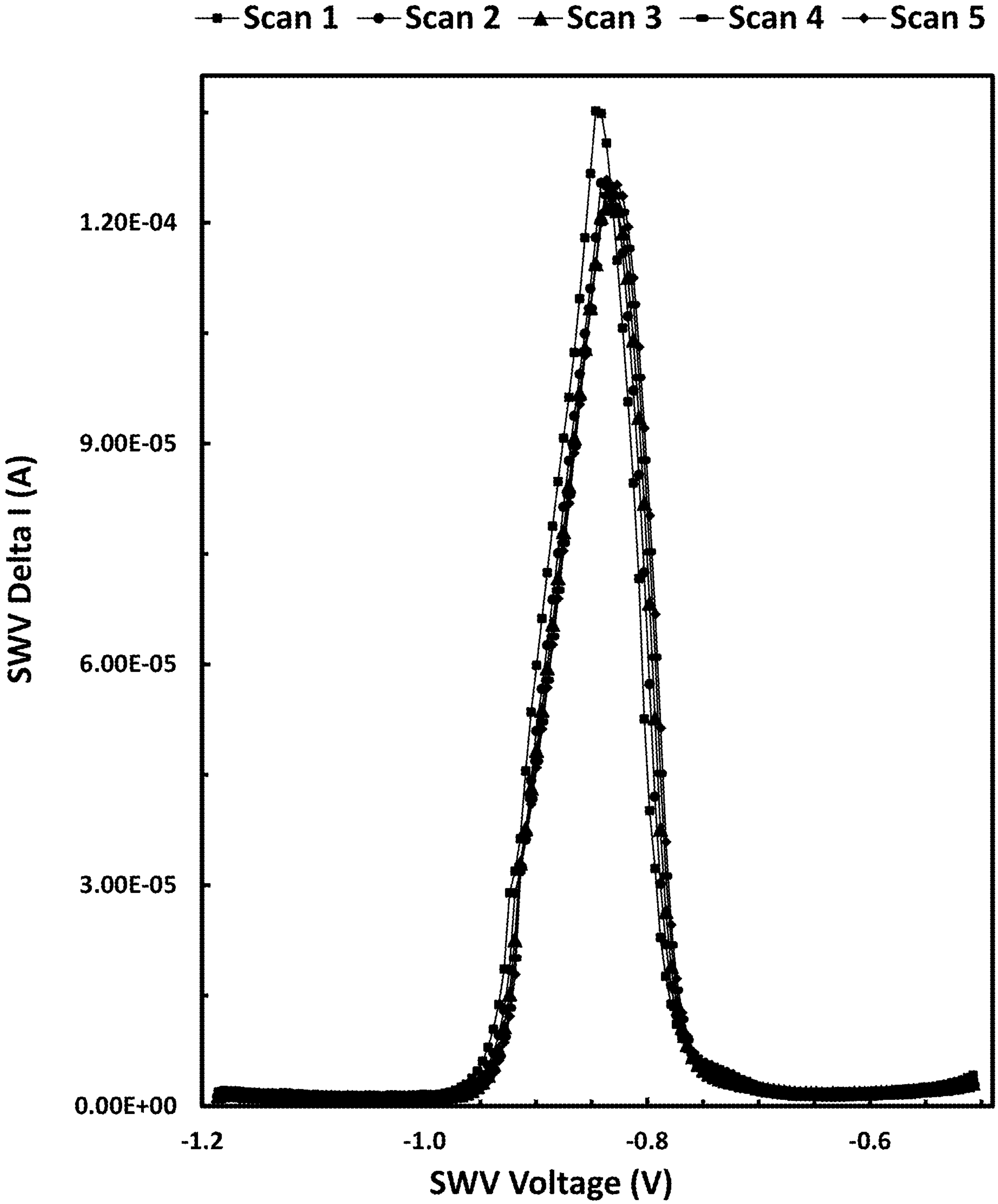
FIG. 21 shows the five square wave voltammetry scans conducted in Example 6.

A total of five square wave voltammetry scans were run per reference correction scan. Based on the initial reference correction scan, each scan started at approximately −1.2 V. As shown in FIG. 21, the routine adjusted the end voltage to approximately −0.5 V based on the initial reference correction scan, and the 5 first scans closely match each other.

A cleaning cycle was then performed by holding a set potential at approximately −0.5 V, completing cycle 1. Another reference correction scan was run, followed by five more square wave voltammetry scans, followed by another cleaning cycle, completing cycle 2. This was repeated three more times (cycles 3, 4, and 5), for a total of 5 reference correction scans, 25 square wave voltammetry scans, and 5 cleaning cycles.

Figure 22:
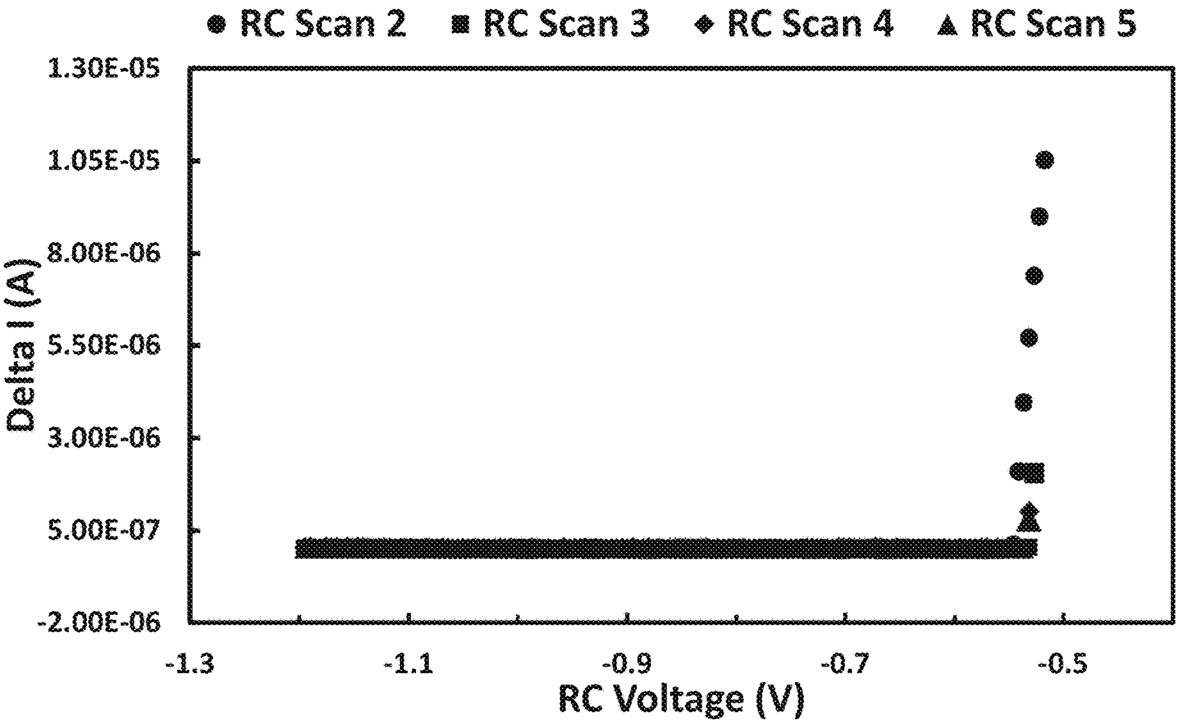
FIG. 22 is a graph showing the reference correction scans for cycles 2 to 5 (Example 6).
Figure 23:
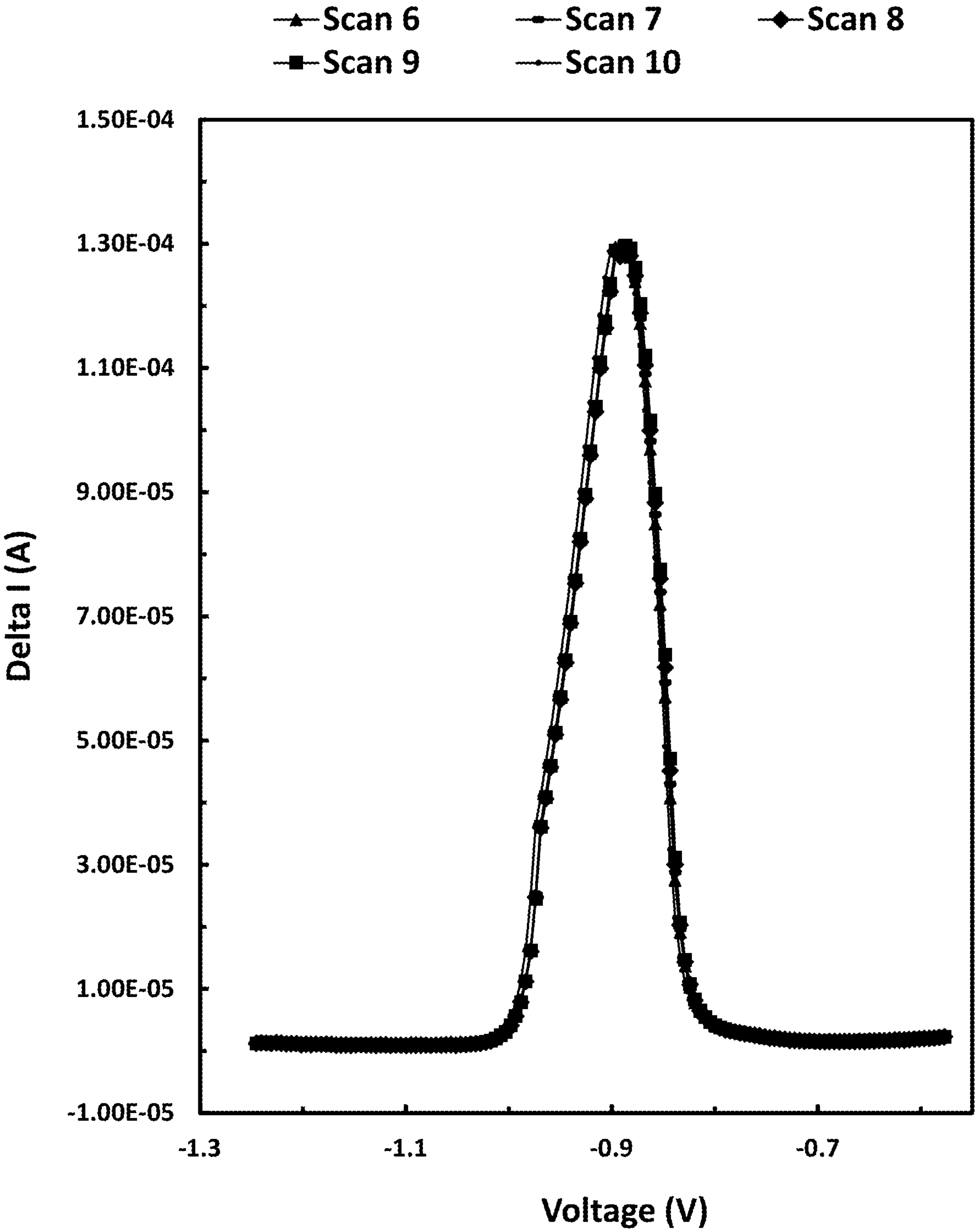
FIG. 23 provides the square wave voltammetry scan for cycle 2 of Example 6.
Figure 24:
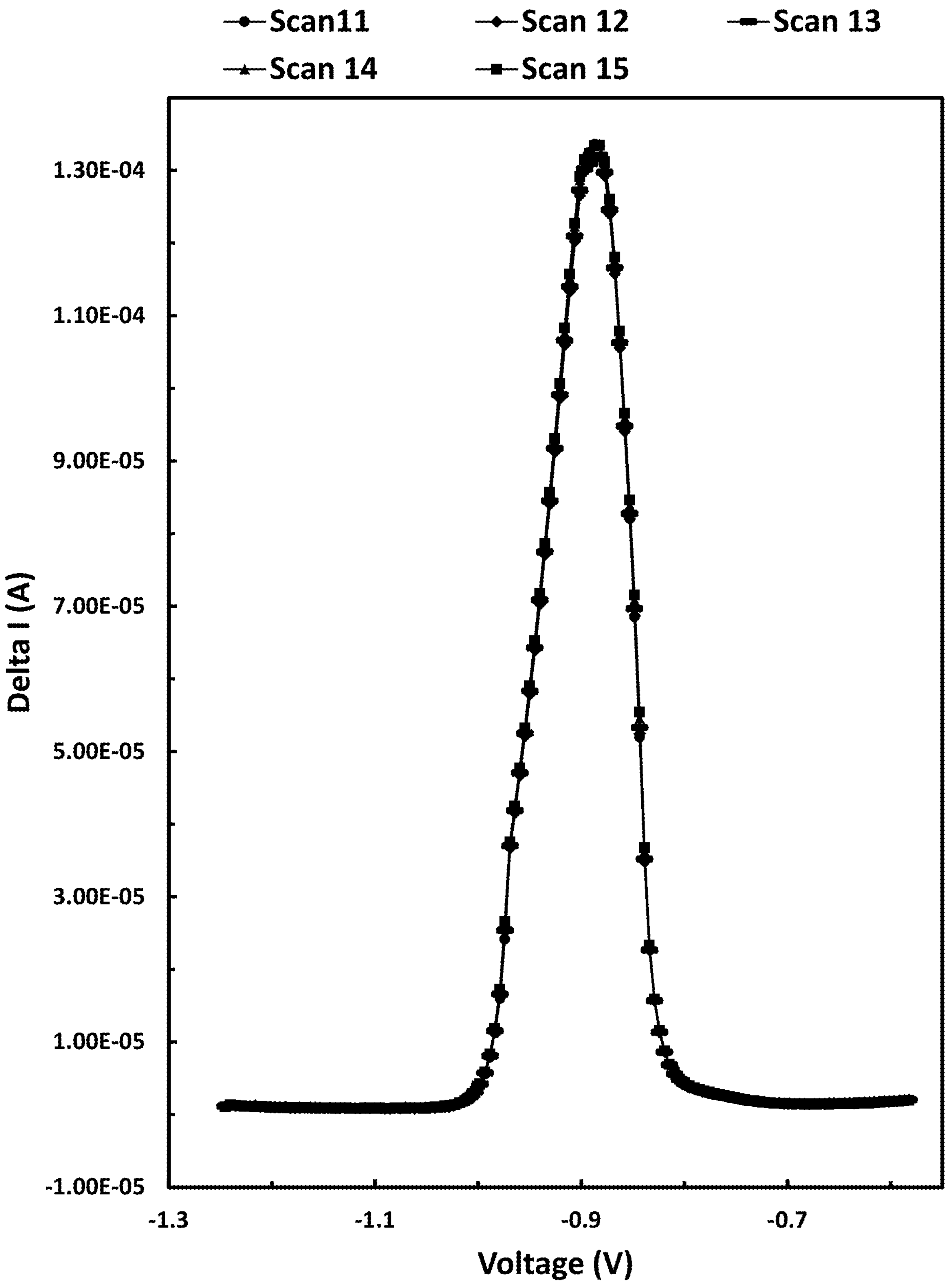
FIG. 24 provides the square wave voltammetry scan for cycle 3 of Example 6.
Figure 25:
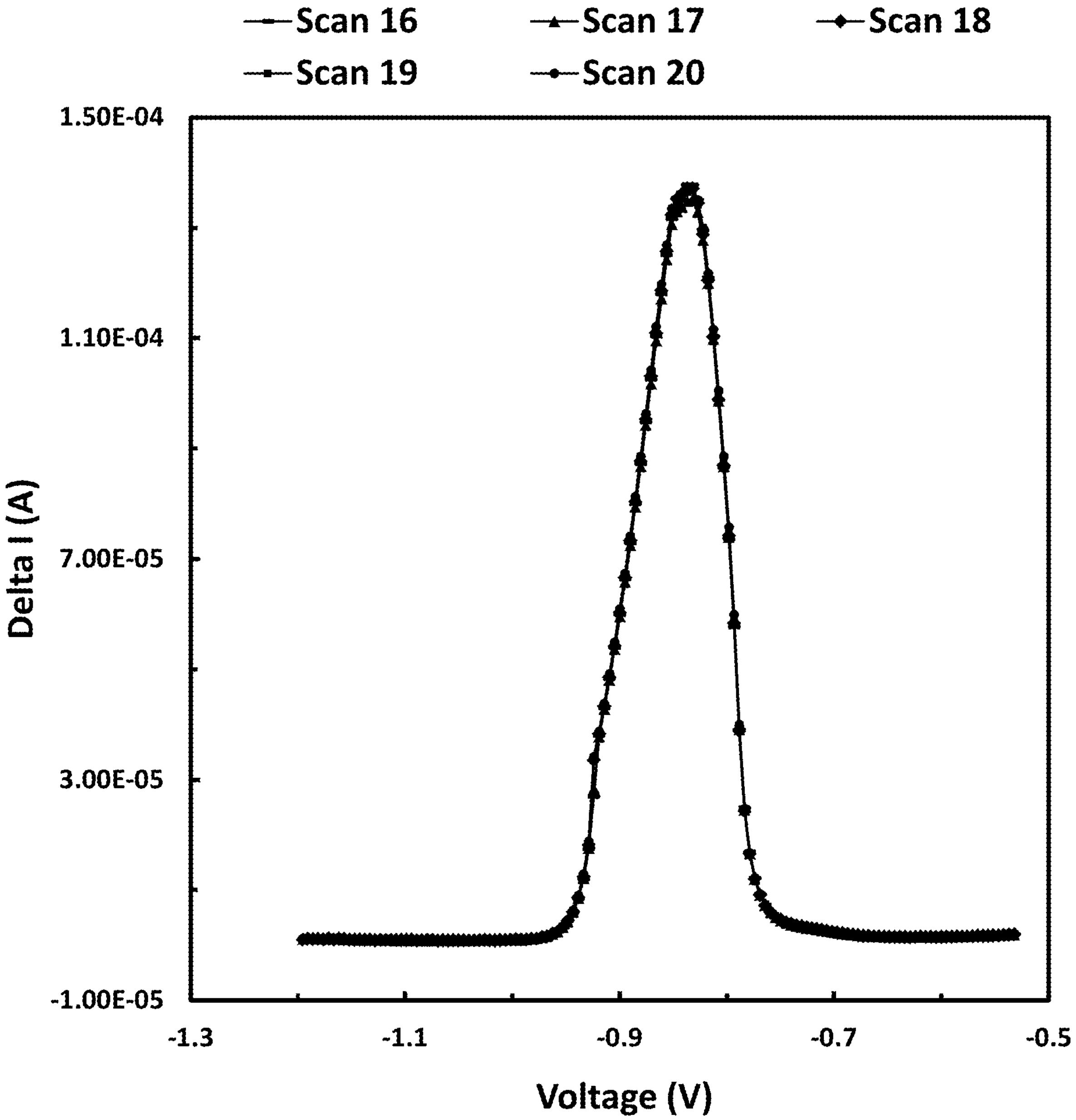
FIG. 25 provides the square wave voltammetry scan for cycle 4 of Example 6.
Figure 26:
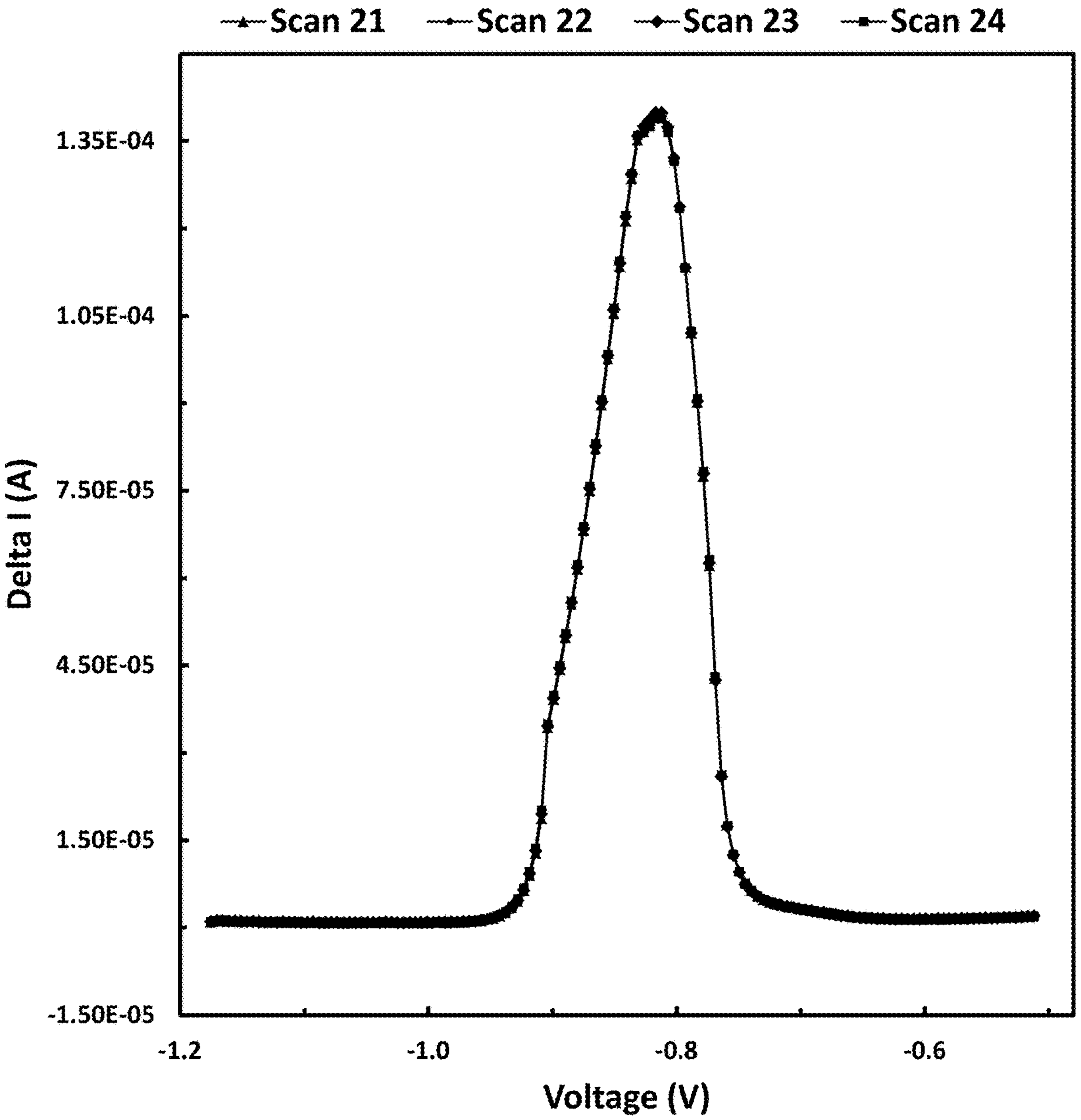
FIG. 26 provides the square wave voltammetry scan for cycle 5 of Example 6.

As shown in FIG. 22, each cleaning cycle was able to completely remove the presence of lead from the sensor and could repeatedly do so over several scans of deposition. FIG. 22 also shows consistency between scans and low drift. From sweep 2 to 3, a small correction can be observed that was automatically made to lower the current draw of the sensor material oxidation peak. FIGS. 23-26 show the SWV cycles for each of cycles 2-5 of testing, respectively. These experimental results show that the SWV sweeps between each reference correction closely match and are quite repeatable over a 24-hour period using the ADuCM355 firmware.

Example 7

Lead Sensor with Silver Working Electrode

Figure 27:
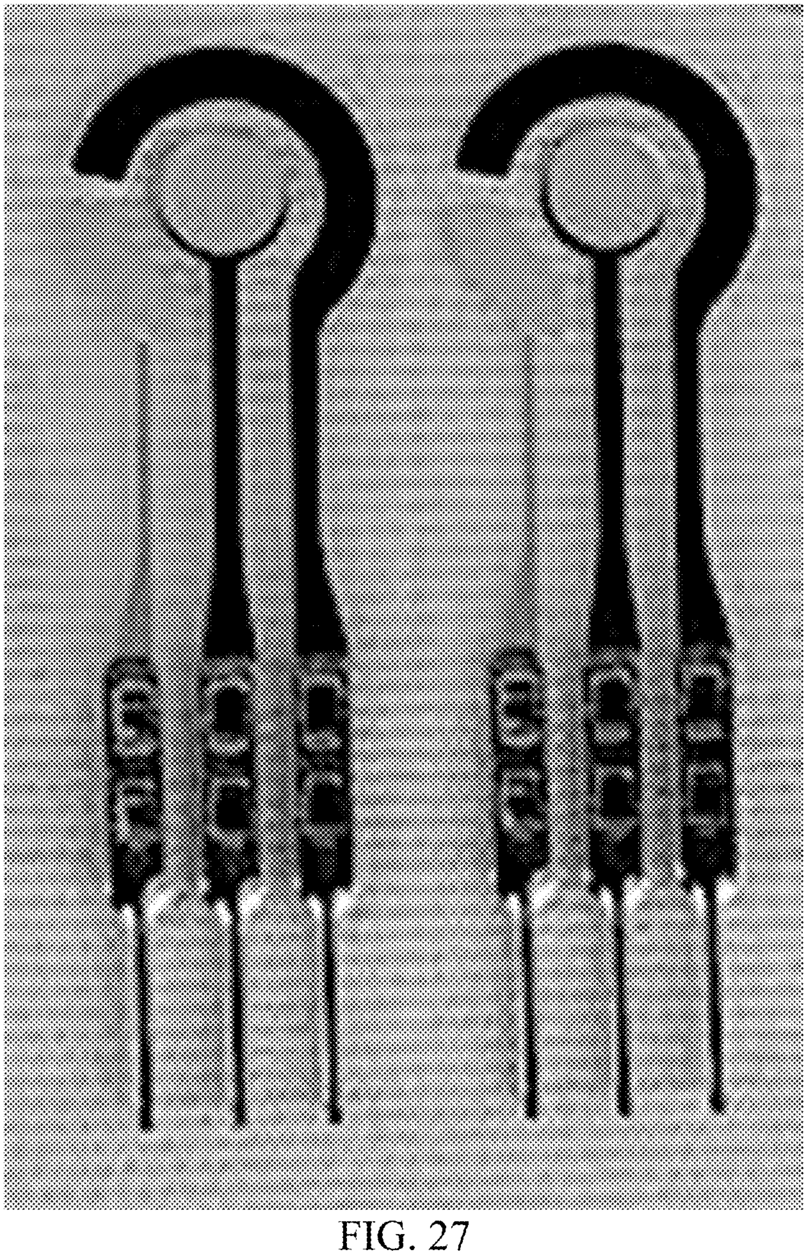
FIG. 27 is a photograph of sensors prepared as described in Example 7.

A gold current collector was sputtered using an Angstrom Engineering EVOVAC 016 Deposition System (Angstrom Engineering Canada Kitchener, Ontario) and Au target with ¼" thickness and 99.999% purity (Angstrom Engineering Canada Kitchener, Ontario) onto a ZEONEX® ZF14-188 substrate (Zeon Europe GmbH, Germany) at a rate of 2A/s for 8.3 minutes using a molybdenum shadow mask for patterning to achieve a thickness of 100 nm. The patterned substrate was then plasma treated using an AST Products Inc. PS-350 plasma etcher (0.1 Torr chamber pressure, 50 sccm $O_2$ flowrate, 50 W RF power, and 30 seconds RF time). A conductive carbon material, DuPont BQ242 (DuPont, Circleville, OH), was screen printed over the gold current collector using a stainless-steel screen (mesh 230 cal with 0.0011" wire diameter), on an ATMA OE67 screen printer, fitted with a 70-durometer polyurethane squeegee. The squeegee speed was set to 250 mm/s, and off contact was set to 1.0 mm. Cure was done in a HIX Corporation NP-2410 IR cure oven with a belt speed of 28 inches per minute and temperature of 130° C. The reference electrode material (60:40 Ag:AgCl; Dupont 5874 Ag/AgCl Ink), was screen printed over the gold current collector to form the reference electrode. The screen printing process used a stainless-steel screen (mesh 230 cal with 0.0011" wire diameter) on an ATMA OE67 screen printer that was fitted with a 70-durometer polyurethane squeegee. The squeegee speed was set to 250 mm/s, and off contact was set to 1 mm. Curing was carried out in a HIX Corporation NP-2410 IR cure oven with a belt speed of 28 inches per minute and temperature of 130° C. To define the working electrode area, DuPont 5018A (DuPont, Circleville, OH) was screen printed over the gold current collector using a stainless-steel screen (mesh 230 cal with 0.0011" wire diameter), on an ATMA OE67 screen printer, fitted with a 70 durometer polyurethane squeegee. The squeegee speed was set to 250 mm/s, and off contact was set to 1.0 mm. Cure was done in a Heraeus DRS 10/12 UV belt oven with two passes at a belt speed of 4.0 feet per minute. Silver (silver target 99.999% pure, Angstrom Engineering, Kitchener, Canada) was sputter deposited over the working electrode to a using an Angstrom Engineering EVOVAC 016 Deposition System (Angstrom Engineering Canada Kitchener, Ontario) at a rate of 2 Å/s for 16.6 minutes using a molybdenum shadow mask for patterning to achieve a thickness of 200 nm. using an Angstrom Engineering EVOVAC 016 Deposition System (Angstrom Engineering Canada Kitchener, Ontario) at a rate of 2 Å/s for 16.6 minutes using a molybdenum shadow mask for patterning to achieve a thickness of 200 nm. A formulation comprising a Nafion™-modified polymer prepared as described in Example 1A was degassed using a PDM-800V planetary mixer from KMtech at 1,350 rpm for revolutions and 0 rpm rotations for 30 minutes. A 10-mil layer of the Nafion™ material was stencil coated over all of the working, counter, and reference electrodes with an MC600 stencil printer from Manncorp. The stencil used was 10 mil (250 μm) thickness, the flood bar speed was set to 25%, and the table separation was set to 100%. Next, 10 mL of the Example 1A ink was loaded evenly onto the stencil. The sensors were then printed and placed on a piece of 10 mil PET backing for curing. Curing was done using a Thermolyne type 42000 incubator with heating at 50° C. for 36 hours. The formed electrodes are shown in FIG. 27, with the sensor dimensions being as shown in FIG. 2.

Example 8

Effect of Solution Type

The sensors' ability to detect $Pb^{2+}$ in low conductivity DI water and in different ion concentrations of synthetic water was studied. The procedure described in Example 1B was followed to form sensors with a 1,000-Å-thick, 3-mm diameter bismuth working electrode coated with a 10-mil layer of the Nafion™ material prepared as described in Example 1A. The sensor was tested in DI water with one blank solution containing 0 ppb $Pb^{2+}$ and another solution containing 100 ppb $Pb^{2+}$. The impedance of the membrane formed from the Nafion™-modified polymer, the pH, and the ionic conductivity ("IC") of solution were then measured using conductivity (Cond probe InLab 752-6 mm) and pH (InLab® Expert Pro) probes from Mettler Toledo, and the results are shown in Table 2.

TABLE 2 pH, IC, and Impedance for Deionized Water Test

| Solution | Average pH (before test) | Average Conductivity/ µS/cm (before Test) | Average Sensor Impedance/ kΩ (before test) | Average Sensor Impedance/ kΩ (after test) |
|---|---|---|---|---|
| DI water | 4.54 | 0.95 | 1.350 | 1.529 |
| 100 ppb Pb in DI water | 4.39 | 18.61 | 1.475 | 1.052 |

Multiple cycles of SWV were run on the same cell with constant solution. All tests used an in-house developed Ag/AgCl external reference electrode comprising an Ag/AgCl wire in 3.5M (saturated) KCl in agarose in a glass tube filled and sealed from the environment, such as by an epoxy adhesive.

Figure 28:
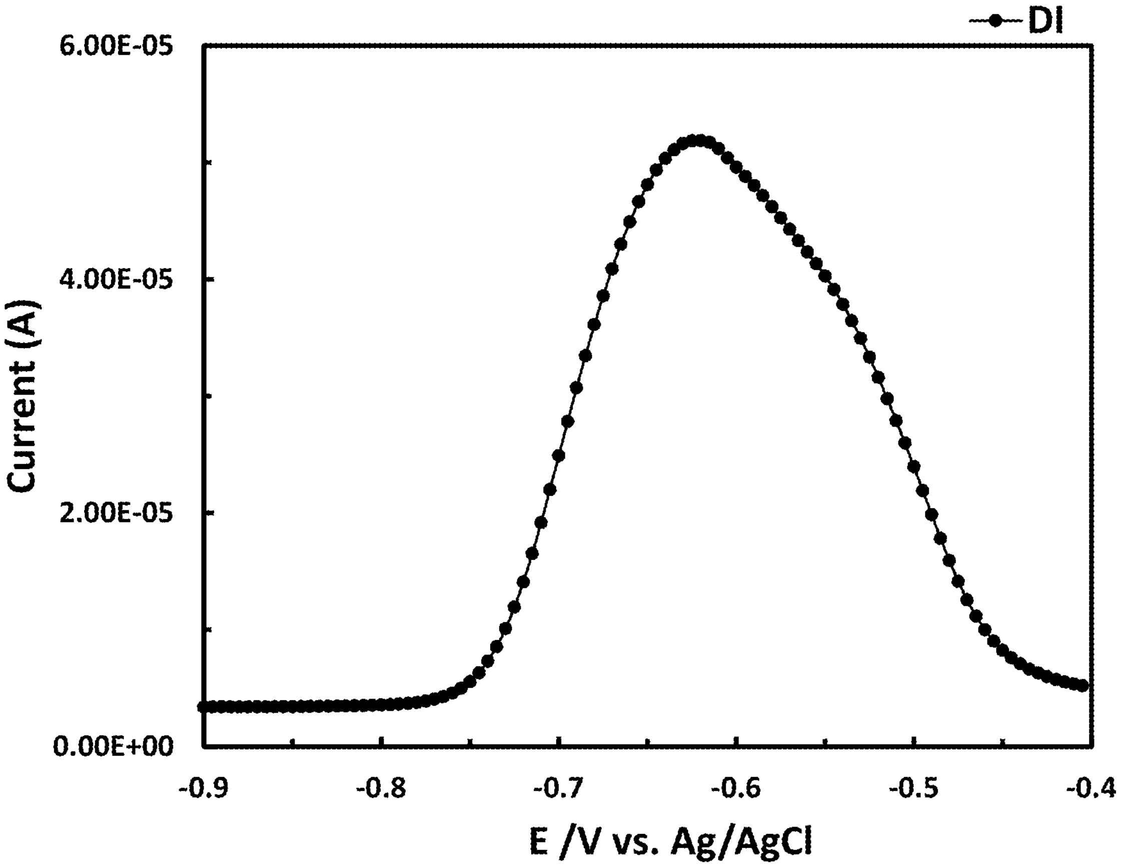
FIG. 28 is a voltammogram of the $25^{th}$ cycle of 50 total square wave voltammetry scan cycles (Example 8).

To effectively display the ion exchange process, which can take several hours, and to generate calibration curves, the sensors were not allowed to soak in solution prior to the first cycle of SWV. The solution volume for each test was 500 mL per sensor. The main electrochemical technique used in all studies was square wave voltammetry performed with a CHI660E potentiostat/CHI 684 multiplexer from CH Instruments. The parameters for this method were initial voltage: −1.2 V, final voltage: −0.4 V, step increment: 0.005 V, amplitude: 0.025 V, frequency: 5 Hz, accumulation time: 300 s, and sensitivity: $1e^{-5}$. The test was run for 50 cycles with a 1-hour delay between each cycle. FIG. 28 shows the voltammogram of the $25^{th}$ cycle this testing.

Next, the sensor was tested in synthetic water solutions (A & B) of varying ions and concentrations based on average surface water values recorded from United States Geological Survey ("USGS"). The respective ion matrices of Solutions A and B are shown in Tables 3 and 4. Solution A's ion matrix included only nitrate anions whereas Solution B contained a variety of ions (i.e., nitrate, chloride, fluoride, and sulfate).

TABLE 3

Solution A Ions and Concentrations
SOLUTION A

| Compound | mg/L |
|---|---|
| $KNO_3$ | 6.7292 |
| $Fe(NO_3)_3$ * $9H_2O$ | 164.4211 |
| $Mn(NO_3)_2$ * X $H_2O$ | 27.7991 |
| $Ca(NO_3)_2$ * 4 $H_2O$ | 200.3504 |
| $Mg(NO_3)_2$ * 6 $H_2O$ | 87.7003 |
| $Zn(NO_3)_2$ * X $H_2O$ | 4.2635 |

TABLE 4

Solution B Ions and Concentrations
SOLUTION B

| Compound | mg/L |
|---|---|
| KF | 0.4849 |
| $KNO_3$ | 5.8857 |
| $FeCl_3$ | 0.06602 |
| $MnCl_2$ | 0.01955 |
| $ZnCl_2$ | 1.95361 |
| $MgCl_2$ | 24.29715 |
| $Mg(NO_3)_2$ * $6H_2O$ | 22.28440 |
| $Ca(NO_3)_2$ * $4H_2O$ | 369.17078 |
| $CaSO_4$ | 10.52937 |

A blank of each solution and a duplicate solution with 100 ppb $Pb^{2+}$ was prepared and used for testing. The impedance of the membrane in DI water, pH, and ionic conductivity of solutions were measured and are shown in Table 5.

TABLE 5 pH, IC, and Impedance for Synthetic Water Test

| Solution | Average pH (before test) | Average Conductivity/ µS/cm (before Test) | Average Sensor Impedance/ kΩ (before test) | Average Sensor Impedance/ kΩ (after test) |
|---|---|---|---|---|
| Solution A | 2.79 | 780 | 1.414 | 2.158 |
| 100 ppb $Pb^{2+}$ in Solution A | 2.90 | 810 | 1.411 | 2.245 |
| Solution B | 5.50 | 547 | 1.464 | 2.215 |
| 100 ppb $Pb^{2+}$ in Solution B | 4.45 | 565 | 1.461 | 2.240 |

Figure 29:
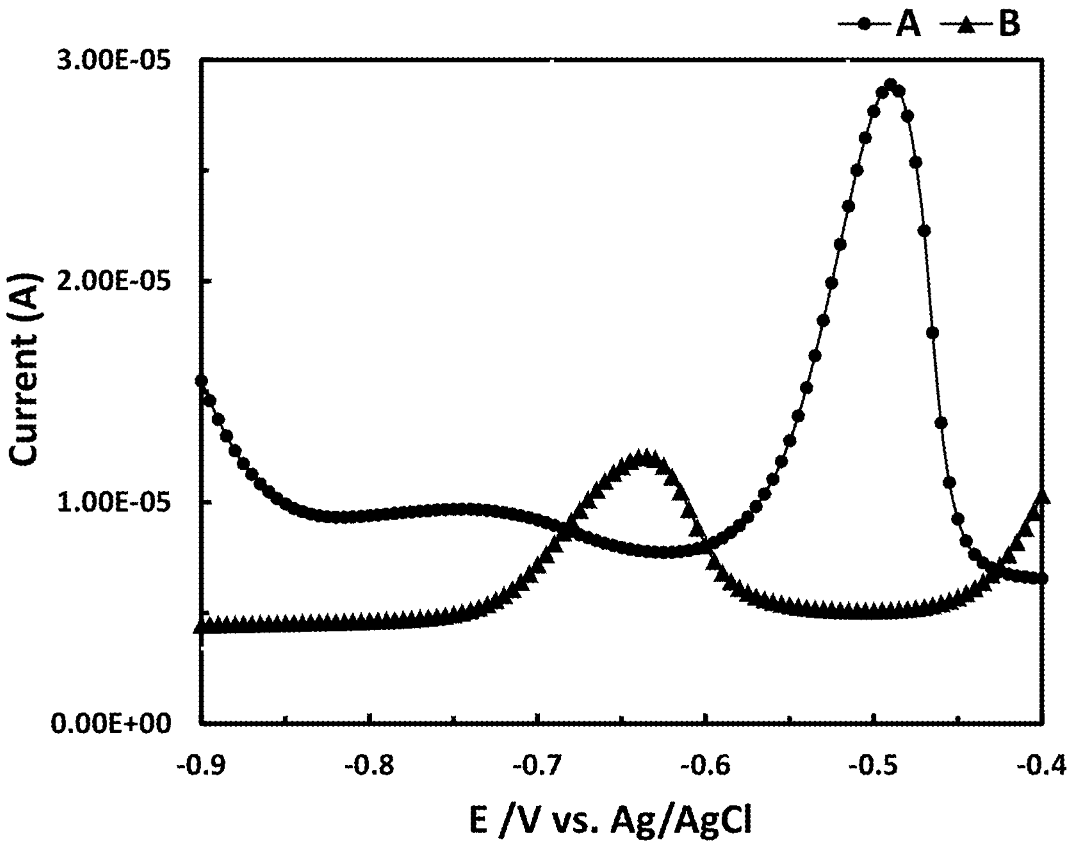
FIG. 29 provides the voltammograms of the $25^{th}$ cycle of 50 total square wave voltammetry scan cycles in each of Solutions A and B, as described in Example 8.

The sensor was then used to perform 50 cycles of SWV as described earlier in this Example. FIG. 29 shows the voltammograms of the sensor in each of Solutions A and B. The $Pb^{2+}$ oxidation peak in DI water, Solution A, and Solution B arose at −0.695 V, −0.575 V, and −0.623 V, respectively. The equilibrium calibration curve for the peak height (Ip) was made and is shown in Table 6.

TABLE 6

Tabulated Data from Equilibrium Calibration Curves and Fits

| Solution | Slope (A/Cycle) | Equilibration Time (hr) | Equili-bration Cycle | Linear Range | $R^2$ | Ip Max (µA) |
|---|---|---|---|---|---|---|
| DI Water | $2.367e^{-6}$ | 31.8 | 18 | 1-18 | 0.964 | 39.6 |
| Solution A | $1.116e^{-5}$ | 3.5 | 3 | 1-3 | 0.974 | 32.2 |
| Solution B | $3.36e^{-7}$ | 54 | 30 | 1-4, 4-30 | 0.840 | 15.2 |

Interestingly, the highest current was observed in DI water. This suggests that higher Ip is more dependent on ion variation and concentration in solution and selectivity of the membrane to ions other than Pb than it is dependent on solution conductivity. The fastest equilibration time was observed in Solution A, with 3.5 hours or 3 cycles.

Example 9

Effect of Interfering Ions

Bismuth's ability to detect $Pb^{2+}$ was tested in the presence of cadmium, a known interfering ion, using a sensor fabricated as described in Example 8. Twelve different matrices of varying concentrations of Pb and Cd were formulated as shown in Table 7, with each using Solution B of Example 8.

TABLE 7

Concentrations of Pb and Cd Ions

| Matrix | Pb/ppb | Cd/ppb |
|---|---|---|
| 1 | 65 | 57 |
| 2 | 83 | 74 |
| 3 | 100 | 40 |
| 4 | 40 | 100 |
| 5 | 57 | 31 |
| 6 | 48 | 48 |

TABLE 7-continued

| Concentrations of Pb and Cd Ions | | |
|---|---|---|
| Matrix | Pb/ppb | Cd/ppb |
| 7 | 14 | 22 |
| 8 | 31 | 91 |
| 9 | 22 | 14 |
| 10 | 5 | 65 |
| 11 | 91 | 83 |
| 12 | 74 | 5 |

Figure 30:
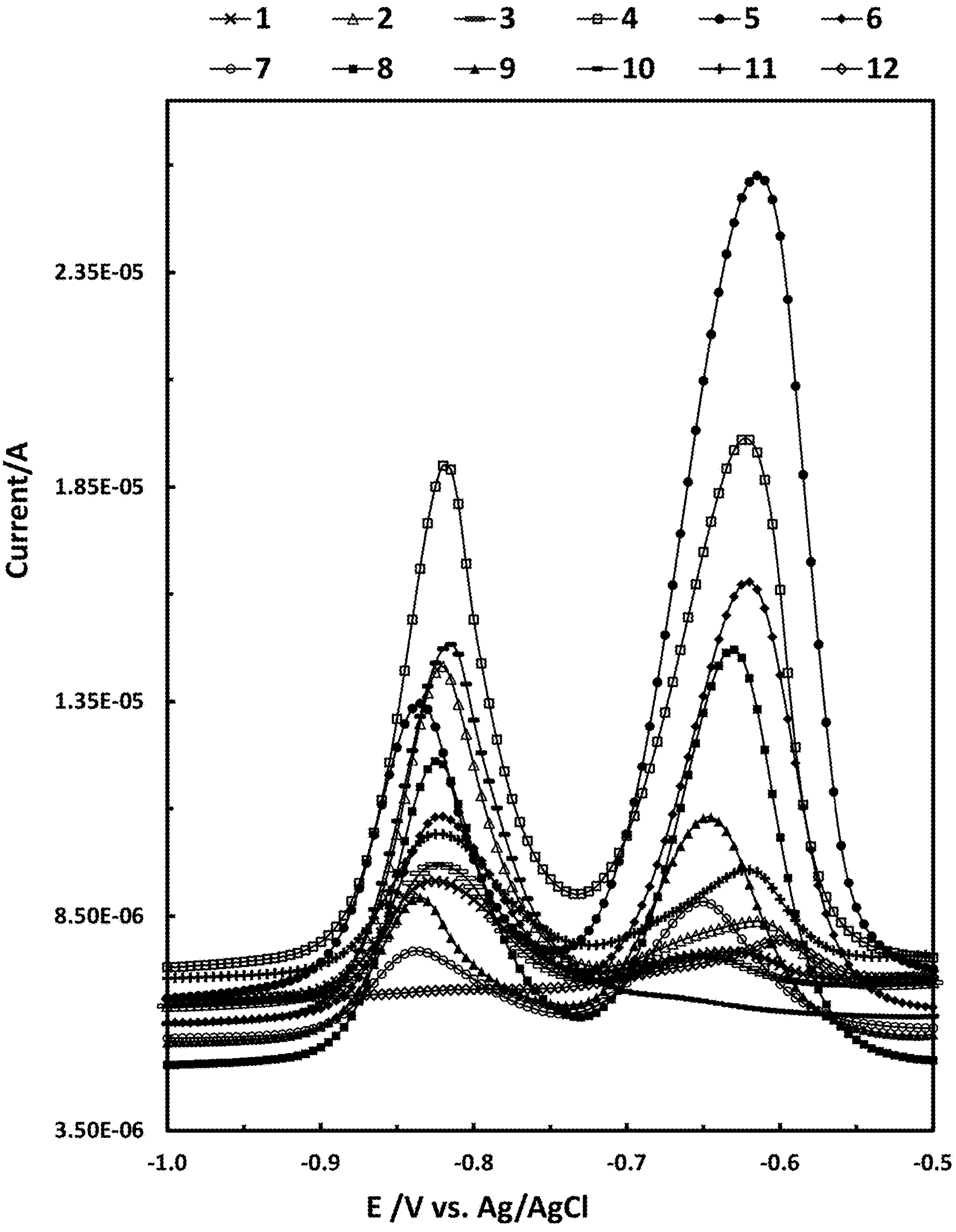
FIG. 30 provides the voltammograms of the $25^{th}$ cycle of 50 total square wave voltammetry scan cycles as described in Example 9.

Each matrix was run for 50 cycles of SWV with 1 hour between each cycle (as in Example 8). The voltammogram shown in FIG. 30 was produced from the $25^{th}$ cycle. This interfering ions study showed that the sensors could detect $Pb^{2+}$ reliably in the presence of Cd. The Pb oxidation peak clearly shows at −0.61 V, with little interference from the Cd peak at −0.82 V.

Example 10

Effect of Internal Reference

Figure 31:
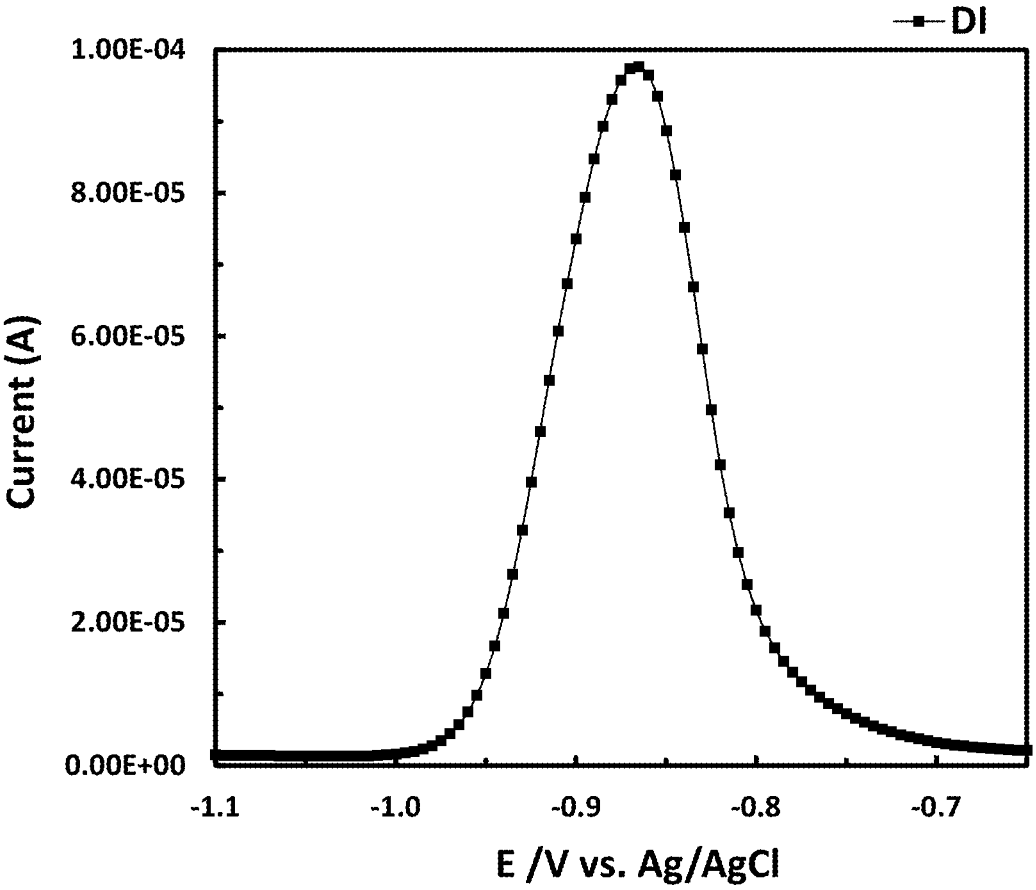
FIG. 31 is a voltammogram of the $25^{th}$ cycle of 50 total square wave voltammetry scan cycles using an internal reference in DI water, as described in Example 10.
Figure 32:
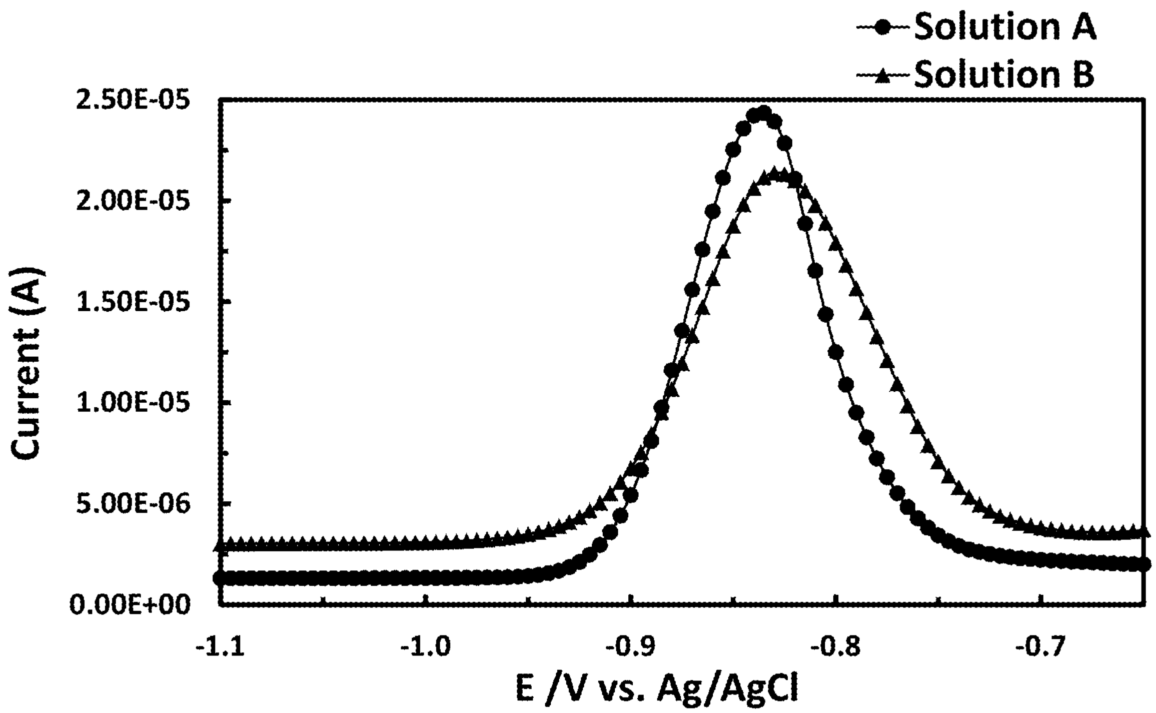
FIG. 32 provides the voltammograms of the $25^{th}$ cycle of 50 total square wave voltammetry scan cycles using an internal reference in each of Solutions A and B, as described in Example 10.

The efficacy of the internal reference for Pb detection was evaluated, using a sensor fabricated as described in Example 8. The same 50-cycle voltammetry test was run as described in Example 8 but, instead of using an external reference electrode, a screen-printed Ag/AgCl reference electrode described in Example 1B was used. The electrochemical SWV parameters were different for this study as the $Pb^{2+}$ oxidation peak shifted to a more negative potential. The initial voltage was changed to −1.3 V, and the final voltage was changed to −0.5 V. The remaining parameters were identical to those described in Example 8. The internal reference was tested in blank and 100 ppb $Pb^{2+}$ DI water, Solution A, and Solution B from Example 7. FIGS. 31 and 32 show the voltammograms generated after 25 cycles into the 50 SWV cycle tests in deionized water (FIG. 31) and in Solutions A and B (FIG. 32). These data showed a shift in Pb potential from ≈−0.55 V (with external reference) to ≈−0.88 V (with internal reference).

Example 11

Effect of Solution Volume

Figure 33:
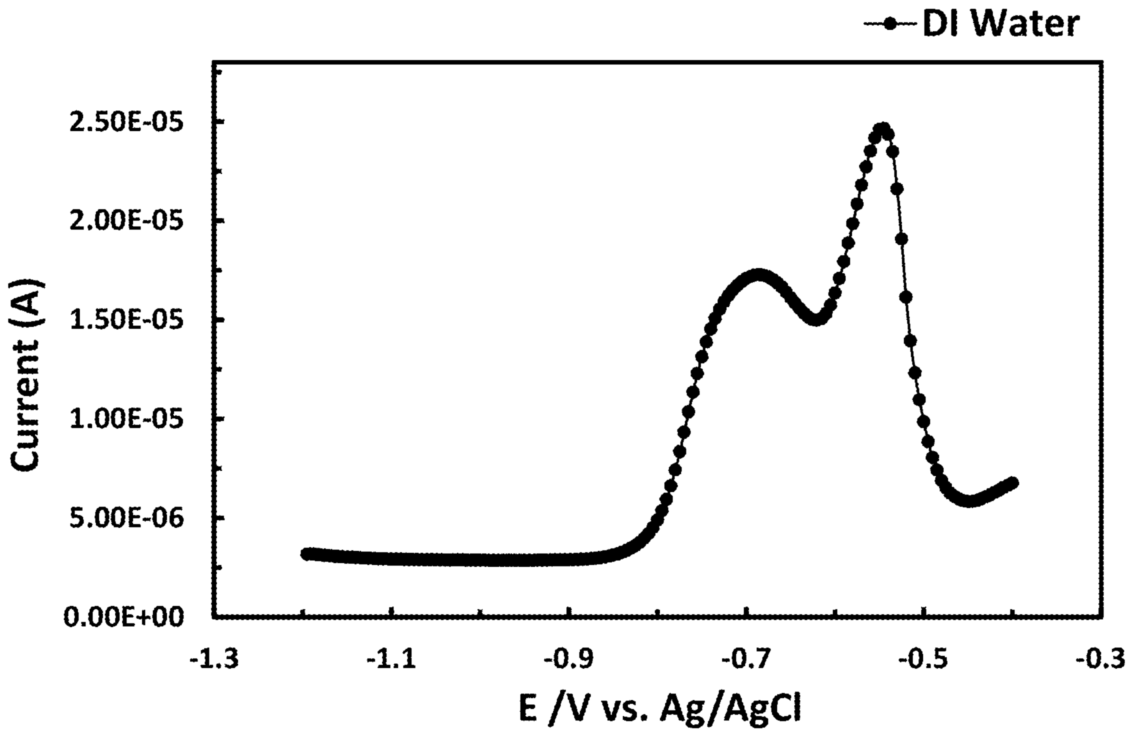
FIG. 33 is a voltammogram of the $25^{th}$ cycle of 50 total square wave voltammetry scan cycles in DI water, as described in Example 11.
Figure 34:
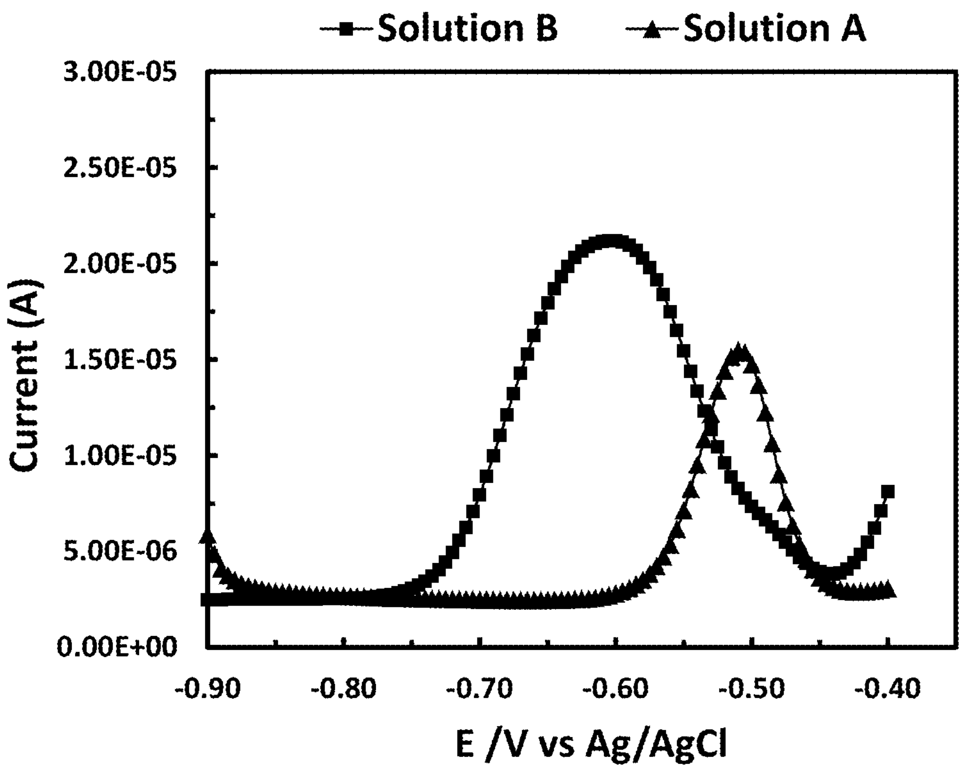
FIG. 34 provides the voltammograms of the $25^{th}$ cycle of 50 total square wave voltammetry scan cycles using an internal reference in each of Solutions A and B, as described in Example 11.
Figure 35:
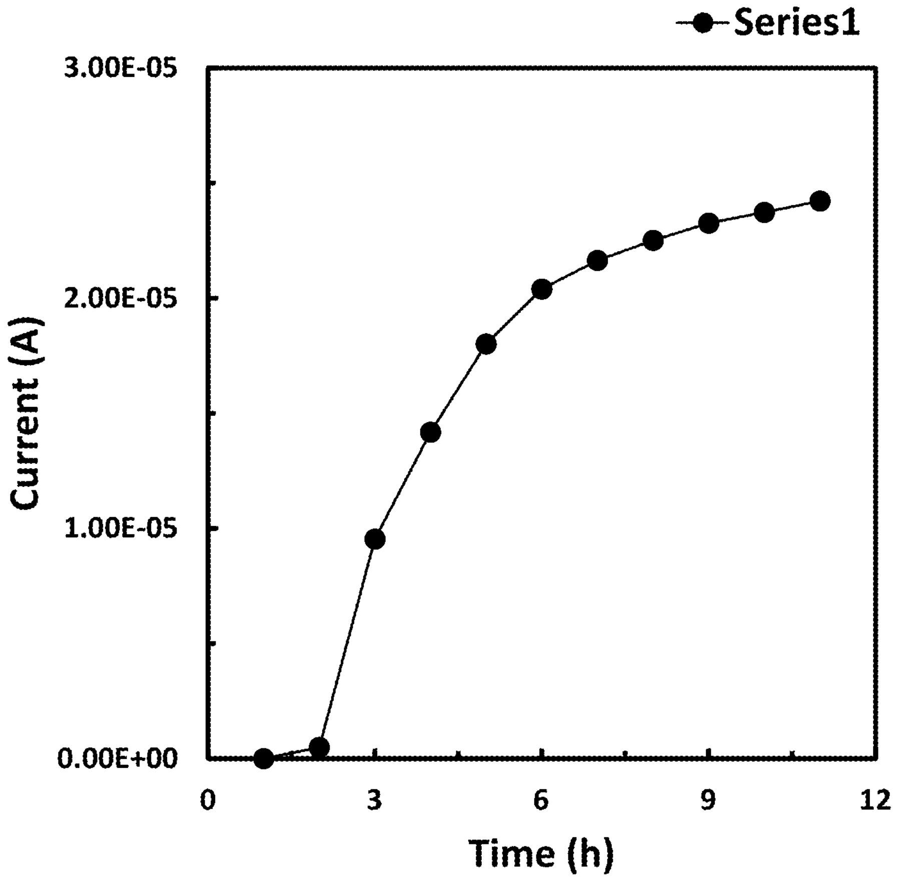
FIG. 35 is a calibration curve of a sensor in a low volume of DI water (Example 11).
Figure 36:
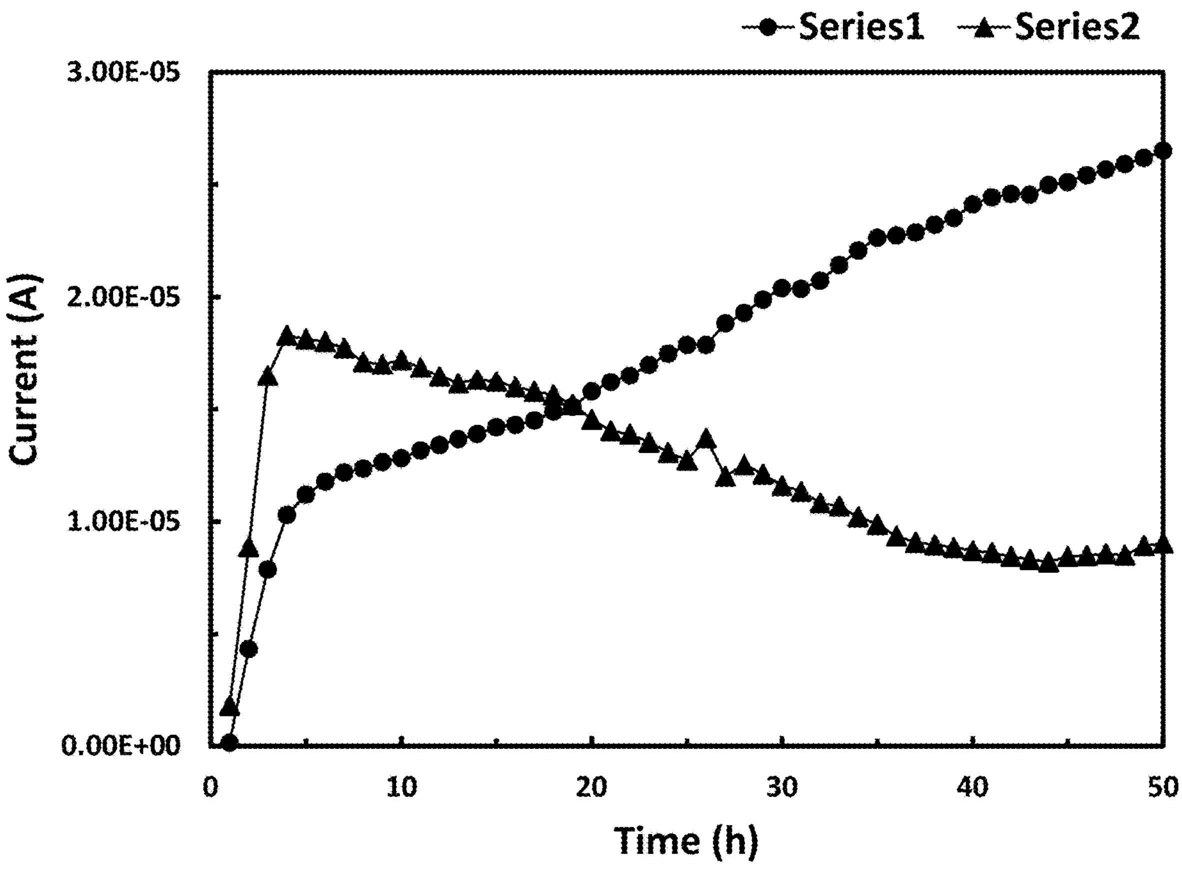
FIG. 36 is a calibration curve of a sensor in a low volume of Solutions A (ascending curve) and B (descending curve) as described in Example 11.

This testing was conducted to demonstrate the difference in signal when the solution volume was changed from 500 mL per sensor to 20 mL. A sensor fabricated as described in Example 8 was used, and the same 50-cycle voltammetry test was run as described in Example 8. FIGS. 33 and 34 show the voltammograms generated after 25 cycles into the 50 SWV cycle tests in deionized water (FIG. 33) and in Solutions A (FIG. 34) and B (FIG. 34). These voltammograms were analyzed for differences and compared to the solution type effect study of Example 8. These data showed that volume affects the behavior of the sensor. Lower volume solutions of DI water and Solution B were less stable, as shown by the calibration curves. DI became convoluted and began to split into two peaks after cycle 11 (FIG. 35), and Solution B actually began to slowly diminish in current after the fourth cycle (descending curve of FIG. 36). Solution A, on the other hand, was stable but never reached equilibrium as the signal continued to increase by 8.8 μA from cycle 25 to 50 (ascending curve of FIG. 36).

Example 12

Fabrication of Nitrate Sensor with Copper Oxide Working Electrode

A gold current collector was sputtered onto a ZEONEX® ZF14-188 substrate (Zeon Europe GmbH, Germany) at a rate of 2 Å/s using a molybdenum shadow mask for patterning to achieve a thickness of 100 nm as in Example 1B. The patterned substrate was then plasma treated using an AST Products Inc. PS-350 plasma etcher (0.1 Torr chamber pressure, 50 sccm $O_2$ flowrate, 50 W RF power, and 30 seconds RF time). A conductive carbon material, DuPont BQ242 (DuPont, Circleville, OH), was screen printed over the gold current collector using a stainless steel screen (mesh 230 cal with 0.0011" wire diameter), on an ATMA OE67 screen printer, fitted with a 70 durometer polyurethane squeegee. The squeegee speed was set to 250 mm/s, and off contact was set to 1.0 mm. Cure was done in a HIX Corporation NP-2410 IR cure oven with a belt speed of 28 inches per minute and temperature of 130° C. Reference electrode material, Sun Chemical-Gwent C2130809D5 (60:40 Ag:AgCl) (Gwent Electric Material Ltd, UK), was screen printed over the gold current collector to for the reference electrode, using a stainless steel screen (mesh 230 cal with 0.0011" wire diameter), on an ATMA OE67 screen printer, fitted with a 70 durometer polyurethane squeegee. The squeegee speed was set to 250 mm/s, and off contact was set to 1 mm. Cure was done in a HIX Corporation NP-2410 IR cure oven with a belt speed of 28 inches per minute and temperature of 130° C. To define the working electrode area, DuPont 5018A was screen printed over the gold current collector using a stainless steel screen (mesh 230 cal with 0.0011" wire diameter), on an ATMA OE 67 screen printer, fitted with a 70 durometer polyurethane squeegee. The squeegee speed was set to 250 mm/s, and off contact was set to 1.0 mm. Cure was done in a Heraeus DRS 10/12 UV belt oven with two passes at a belt speed of 4.0 feet per minute. Copper (Kurt J. Lesker Company, Jefferson Hills, PA) was E-beam deposited over the working electrode to a thickness of 200 nm using a molybdenum shadow mask. After completing the copper deposition, the devices were placed into the AST Products Inc. PS-350 radio frequency oxygen plasma chamber at 150 W for 2 minutes. This oxidized the orange and red copper to a purple and blue color.

Example 13

Fabrication of Nitrate Sensor with Cnt and Copper Electrodeposited Working Electrode A gold current collector was sputtered onto a ZEONEX® ZF14-188 substrate (Zeon Europe GmbH, Germany) at a rate of 2 Å/s using a molybdenum shadow mask for patterning to achieve a thickness of 100 nm as in Example 1B. The patterned substrate was then plasma treated using an AST Products Inc. PS-350 plasma etcher (0.1 Torr chamber pressure, 50 sccm $O_2$ flowrate, 50 W RF power, and 30 seconds RF time). A conductive carbon material, DuPont BQ242 (DuPont, Circleville, OH), was screen printed over the gold current collector using a stainless steel screen (mesh 230 cal with 0.0011" wire diameter), on an ATMA OE67 screen printer, fitted with a 70 durometer polyurethane squeegee. The squeegee speed was set to 250 mm/s, and off contact was set to 1.0 mm. Cure was done in a HIX Corporation NP-2410 IR cure oven with a belt speed of 28 inches per minute and temperature of 130° C. Reference electrode material, Sun Chemical-Gwent C2130809D5 (60:40 Ag:AgCl) (Gwent Electric Material Ltd., UK), was screen printed over the gold current collector to for the reference electrode, using a stainless steel screen (mesh 230 cal with 0.0011" wire diameter), on an ATMA OE67 screen printer, fitted with a 70 durometer polyurethane squeegee. The squeegee speed was set to 250 mm/s, and off contact was set to 1 mm. Cure was done in a HIX Corporation NP-2410 IR cure oven with a belt speed of 28 inches per minute and temperature of 130° C. To define the working electrode area, DuPont 5018A (DuPont, Circleville, OH) was screen printed over the gold current collector using a stainless steel screen (mesh 230 cal with 0.0011" wire diameter), on an ATMA OE 67 screen printer, fitted with a 70 durometer polyurethane squeegee. The squeegee speed was set to 250 mm/s, and off contact was set to 1.0 mm. Cure was done in a Heraeus DRS 10/12 UV belt oven with two passes at a belt speed of 4.0 feet per minute. Next, thin-walled CNTs (Cheaptubes) were functionalized with pyrene, as described in U.S. Pat. No. 9,157,003, incorporated by reference herein, after which 5 layers of the pyrene-functionalized CNTs were spray coated onto the working electrode using a circular metal stencil on a SonoTek spray coater. These CNTs were sprayed at a rate of 0.5 mL/min, 60 kPa shaping air, and 50 mm/see head speed. Once the CNTs were deposited, the sensors were pinned with Sn crimp connectors; and connected properly to a Gamry Instruments, Reference 3000 potentiostat along with Ag/AgCl (Sat. KCl) reference electrode described in Example 8 electrodeposit copper onto the working electrode. A premade solution of 1M copper sulfate (Sigma Aldrich, St. Louis, MO) with 0.5M sulfuric acid (Sigma Aldrich) and 18 MΩ deionized water was used for copper electrodeposition. The devices connected to the Gamry potentiostat were placed into this solution. The method applied from the Gamry potentiostat was cyclic voltammetry. The parameters were 5 cycles running from 0 V (vs. reference electrode) to −0.4 V (vs. reference electrode) at a scan rate of 100 mV/s. Once all 5 cycles were run, the sensor had a smooth layer of orange and red copper deposited on the working electrode.

Example 14

Sensing of Nitrate Using Square Wave Voltammetry

Figure 37:
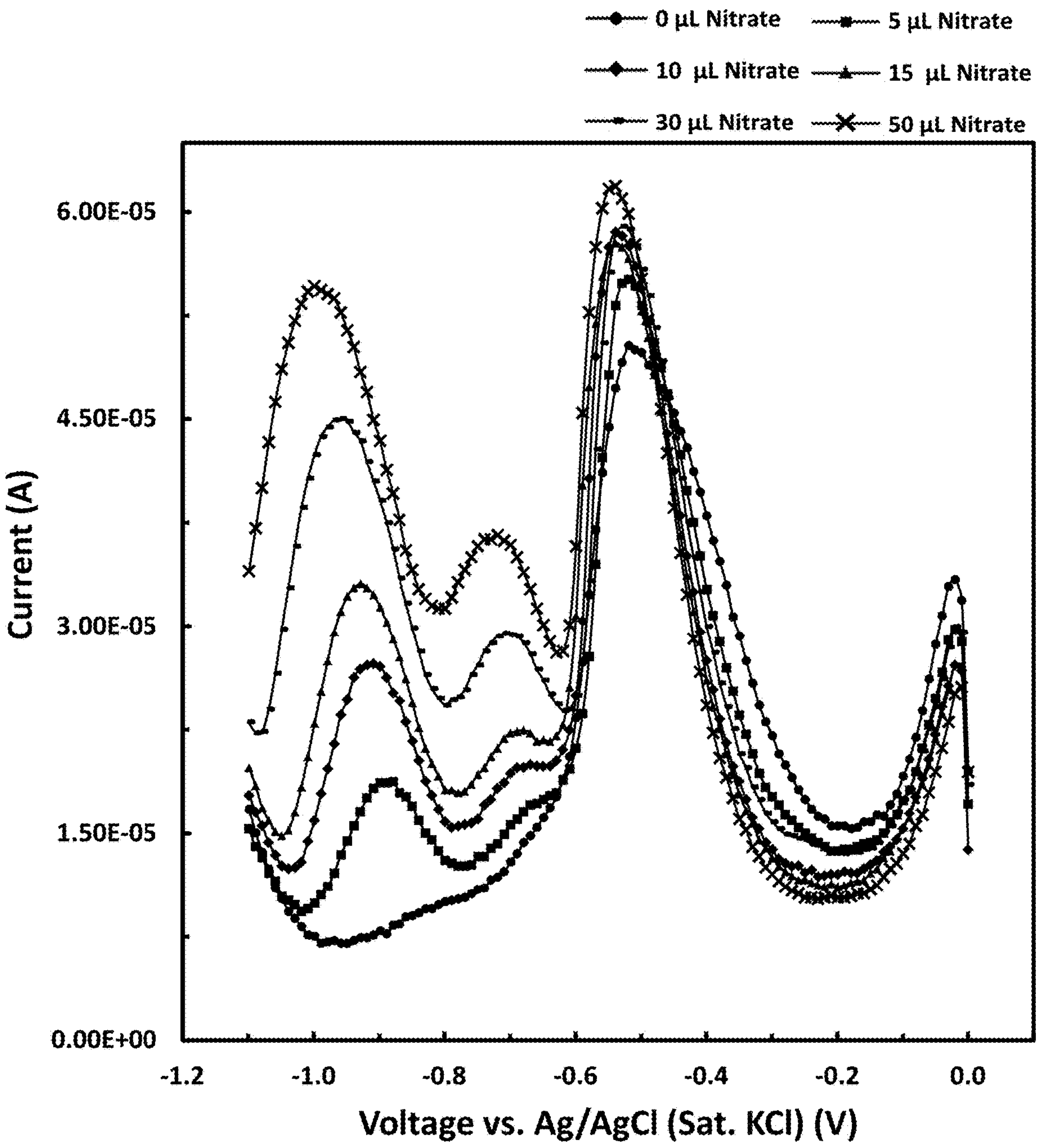
FIG. 37 is a voltammogram of square wave voltammetry scan cycles of nitrate, as described in Example 14.

Solutions of 10 mM KCl were made with 18 MΩ deionized water along with stock solution of 10 mM, 100 mM, and 500 mM $KNO_3$. The KCl solutions were around 5.5 pH and not buffered. The sensors tested contained a CNT electrode with copper electrodeposited on the working electrode (described in detail in Example 14). For this experiment, the devices were connected to a Gamry Instruments, Reference 3000 potentiostat. A voltammogram was produced for 0, 8.41, 16.83, 25.3, 50.4, and 94 ppm of nitrate in 10 mM KCl. Voltammograms were produced using square wave voltammetry. Parameters used for performing SWV were a 0 V to −1.1 V electrochemical window, a 35 mV amplitude, a frequency of 4 Hz, with 111 datapoints taken along the whole range of the scan. The voltammogram produced from this experiment is shown in FIG. 37. It can be seen starting with the blue voltammogram line (0 ppm nitrate) that as nitrate increases, the Gaussian-like peaks become larger, hence the peaks can be correlated to nitrate concentration using a calibration curve.

Example 15

Sensing of Nitrate Using Square Wave Voltammetry

Figure 38:
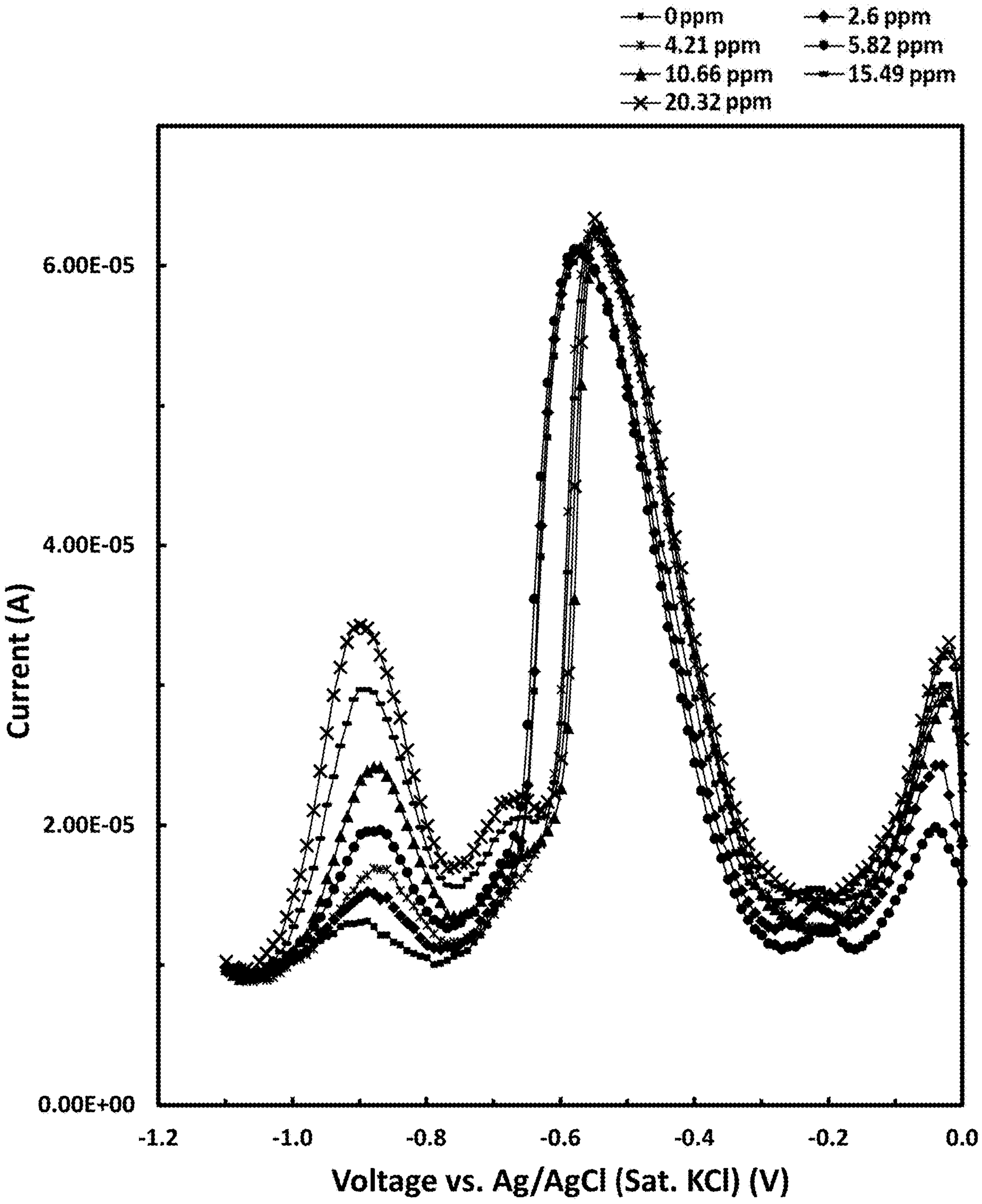
FIG. 38 is a voltammogram of square wave voltammetry scan cycles of nitrate, as described in Example 15.

Solutions of 10 mM KCl were made with 18 MΩ deionized water along with stock solution of 10 mM, 100 mM, and 500 mM $KNO_3$. The KCl solutions were around 5.5 pH and not buffered. The sensors tested contained a copper sputtered electrode (described in detail in Example 13 but without the plasma treatment to explore use of non-oxidized electrode). The devices were connected to a Gamry Instruments, Reference 3000 potentiostat. A voltammogram was produced for 0.98, 2.6, 4.2, 5.8, 10.6, 15.5, and 20.3 ppm of nitrate in 10 mM KCl. Voltammograms were produced using square wave voltammetry. Parameters used for performing SWV were a 0 V to −1.1 V electrochemical window, a 35 mV amplitude, a frequency of 4 Hz, with 111 datapoints taken along the whole range of the scan. The voltammogram produced from this experiment is shown in FIG. 38. It can be seen starting with the blue voltammogram line (0 ppm nitrate) that as nitrate increases, the Gaussian-like peaks become larger, and the peaks can be correlated to nitrate concentration using a calibration curve.

Example 16

Calibration Curve Testing for Cadmium Detection

Figure 39:
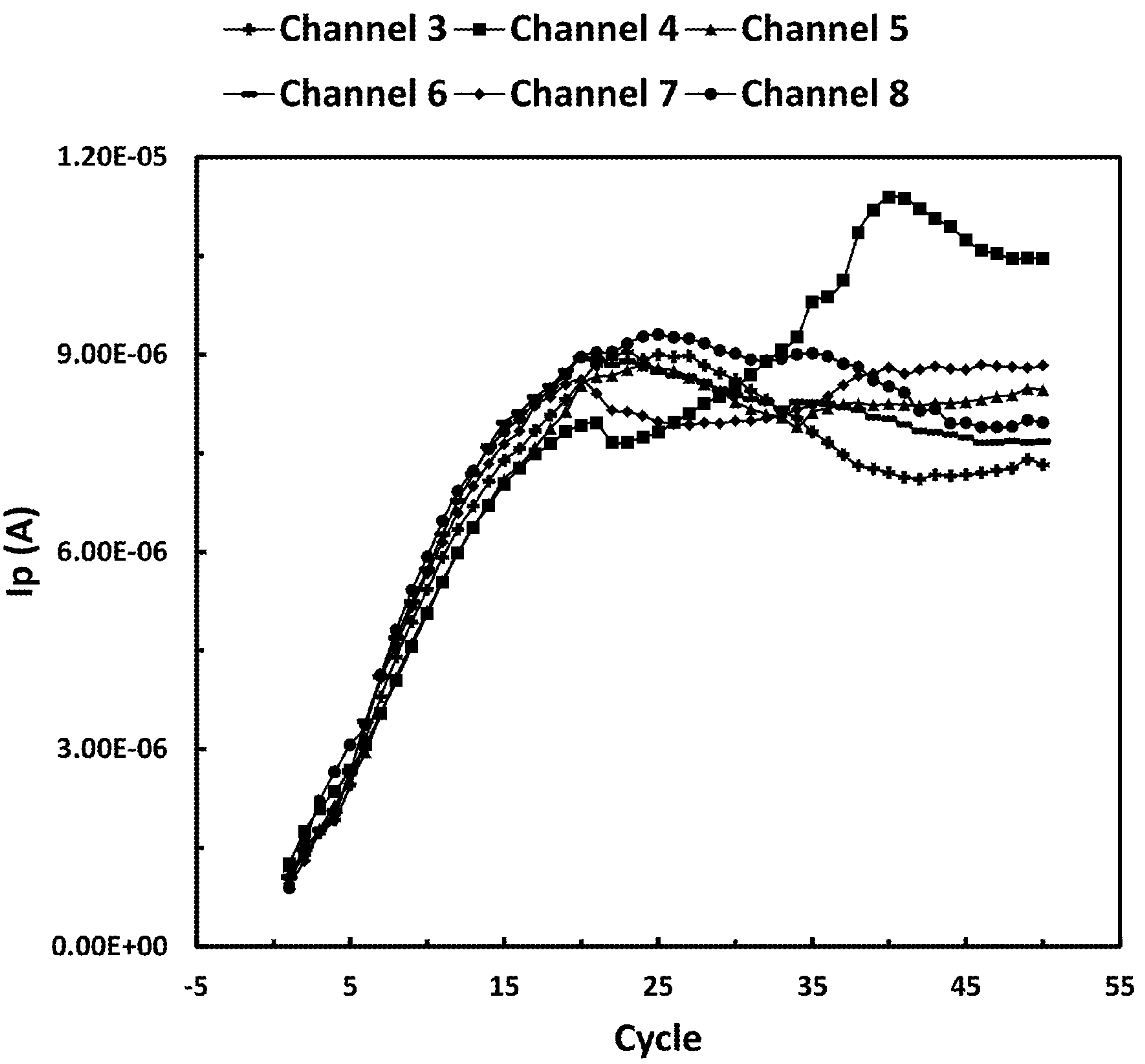
FIG. 39 is a voltammogram of square wave voltammetry scan cycles of cadmium, as described in Example 16.

Sensors as fabricated in Example 1B were calibrated for cadmium detection. A test was set up to observe trends in peak height (Ip), A, with time in solution. The solution used was the synthetic water formulation shown in Table 8. Square wave anodic stripping analysis was performed using a CHI660E electrochemical workstation coupled with CHI 684 multiplexer (CH Instruments Inc., USA). The potential window was from −1.3 V to −0.8 V with a frequency of 5 mV, increment of 5 mV, amplitude of 25 mV, sensitivity of $1e^{-5}$ A/V, and a quiet time of 300 s. The sensors were soaked in solution for 2 hours before the SWV cycle was started. There was an hour wait period between each cycle, and the test was run for 50 cycles. Two sensors were placed in a blank solution of synthetic water, and the other six sensors were placed in synthetic water dosed to 100 ppb cadmium (II) from a cadmium nitrate standard. The solution bottle had a volume of 125 mL. Two sensors were placed in each solution bottle. As shown in FIG. 39, the Ip starts to plateau after cycle 20, at roughly 22 hours in solution. This indicates that for a stable measurement of Ip, roughly a day of soaking and/or at least 20 cycles must be run. Alternatively, extrapolation from the linear range of the graph, cycles 1-20, could be used.

TABLE 8

Contents of synthetic water formulation

| Chemical | Concentration (mM) |
|---|---|
| KF | 0.0083474 |
| $KNO_3$ | 0.0582156 |
| $FeCl_3$ | 0.000407 |
| $MnCl_2$ | 0.0001554 |
| $ZnCl_2$ | 0.0143316 |
| $MgCl_2$ | 0.2551928 |
| $Mg(NO_3)_2$ * $6H_2O$ | 0.0869093 |
| $Ca(NO_3)_2$ * $4H_2O$ | 1.5632894 |
| $CaSO_4$ | 0.0773423 |

Example 17

Detection Limit of Sensors for Cadmium Detection

This test was set up to find the detection limit of the sensor fabricated in Example 1B for detecting cadmium. The detection limit was tested in three different solutions to observe changes in Ip at lower concentrations. These solutions were deionized water, the synthetic water formulation shown in Table 8, and the synthetic water formulation shown in Table 9. Square wave anodic stripping analysis was performed using a CHI660E electrochemical workstation coupled with CHI 684 multiplexer (CH Instruments Inc., USA). The potential window was from −1.25 V to −0.8 V with a frequency of 5 mV, increment of 5 mV, amplitude of 25 mV, sensitivity of $1e^{-5}$ A/V, and a quiet time of 300 s. The sensors were soaked in solution for 12 hours before the SWV cycle started. There was an hour wait period between each cycle, and the test was run for 20 cycles. For every solution made, two sensors were placed in each bottle. A blank solution, 3 ppb cadmium, 5 ppb cadmium, and 10 ppb cadmium solutions were all made using the three different blank solutions and the cadmium from a cadmium nitrate standard (12 solutions total). The solution volume was 125 mL. The results of this test are shown in Table 10.

TABLE 9

| Chemicals in synthetic water | |
|---|---|
| Chemical | Concentration (mM) |
| $KNO_3$ | 0.0665601 |
| $Mg(NO_3)_2$ * $6H_2O$ | 0.34203167 |
| $Ca(NO_3)_2$ * $4H_2O$ | 0.84840319 |
| $Fe(NO_3)$ * $9H_2O$ | 0.40698299 |
| $Mn(NO_3)_2$ * $XH_2O$ | 0.15534583 |
| $Zn(NO_3)_2$ * $6H_2O$ | 0.0143316 |

As seen in Table 10, the sensors were able to detect cadmium concentrations down to 3 ppb cadmium in all three solutions. For DI water, the cadmium peak was lost in the noise of the scan; this could be due to the low conductivity of DI water allowing for a higher Ohmic drop and migration interferences. For the synthetic water shown in Table 9, potential interreferences could come from the amount of nitrates in solution and/or the lower pH around 2.9.

TABLE 10

| Ip for each solution compared to the concentration of cadmium in the solution. | | | |
|---|---|---|---|
| Concentration | DI Water Cycle 20 Ip (μA) | Synthetic Water Table 8 Cycle 20 Ip (μA) | Synthetic Water Table 9 Cycle 20 Ip (μA) |
| 3 | 0.0026 | 0.0341 | — |
| 3 | 0.0165 | 0.0446 | 0.0617 |
| 5 | — | 0.0804 | 0.0726 |
| 5 | — | 0.1242 | 0.1317 |
| 10 | 0.0982 | 0.2537 | 0.1997 |
| 10 | — | 0.3075 | 0.5026 |

Example 18

Linear Range Testing for Cadium Detection

Figure 40:
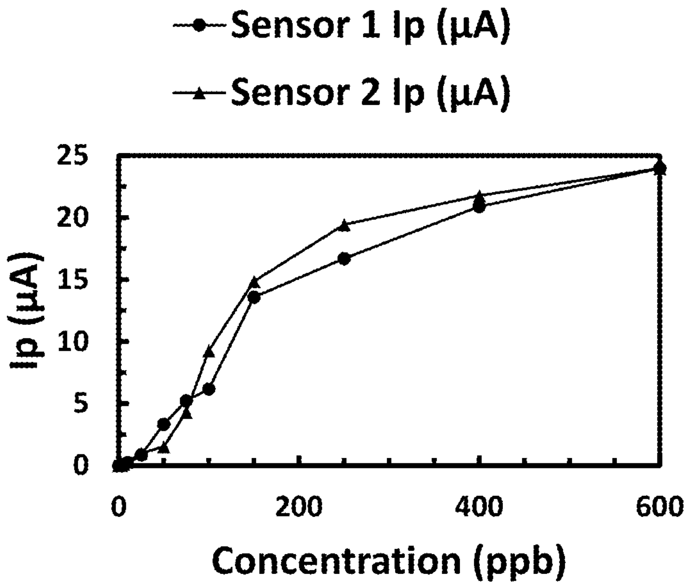
FIG. 40 is a calibration curve based on a voltammogram of square wave voltammetry scan cycles of cadmium, as described in Example 18.

A linear range for the sensors fabricated in Example 1B was established with this test. This linear range test was performed with the synthetic water formulation from Table 8. Square wave anodic stripping analysis was performed using a CHI660E electrochemical workstation coupled with CHI 684 multiplexer (CH Instruments Inc., USA). The potential window was from −1.3 V to −0.8 V with a frequency of 5 mV, increment of 5 mV, amplitude of 25 mV, sensitivity of 1e−5 A/V, and a quiet time of 300 s. The sensors were soaked in solution for 12 hours before the SWV cycle started. There was an hour wait period between each cycle and the test was run for 20 cycles. For every solution made (volume of 125 mL), two sensors were placed in each bottle, with one sensor being labeled sensor 1 and the second labeled sensor 2. The cadmium concentration started at 0 ppb cadmium and increased by varying increments up to 600 ppb cadmium in synthetic water. The results from this test are shown in FIG. 40. Sensor group 1 encompasses all the sensors labeled sensor 1, and the same holds for sensor group 2. The linear range was found to be 0-250 ppb cadmium in solution, well above the 5 ppb EPA limit for cadmium.

Example 19

Solution Effect Test for Cadmium Detection

A solution effect test was performed to observe the effects of different pHs, conductivities, solution matrices, etc., on cadmium detection with the sensors fabricated in Example 1B. Square wave anodic stripping analysis was performed using a CHI660E electrochemical workstation coupled with CHI 684 multiplexer (CH Instruments Inc., USA). The potential window was from −1.2 V to −0.6 V with a frequency of 5 mV, increment of 5 mV, amplitude of 25 mV, sensitivity of $1e^{-5}$ A/V, and a quiet time of 300 s. There was no soak time for this experiment. There was an hour wait period between each cycle and the test was run for 25 cycles. For every solution made (volume of 125 mL), two sensors were placed in each bottle. There were two sensors in each blank solution and 6 sensors in 100 ppb cadmium nitrate standard in the various synthetic waters used for this test. The synthetic waters tested in this experiment are shown in Table 11. The following table, Table 12, shows the ionic conductivity, pH, chloride concentration, nitrate concentration, and sulfate concentration, measured for each solution.

TABLE 11

| breakdown of all the chemicals and their amounts in each synthetic water (SW) formulation used for this experiment. | | | | | | | |
|---|---|---|---|---|---|---|---|
| Chemical | NSW (mM) | SW1 (mM) | SW2 (mM) | SW3 (mM) | SW4 (mM) | SW5 (mM) | SW6 (mM) |
| KF | — | 0.0083474 | 0.034632 | 0.0175474 | 0.0083474 | 0.0083474 | 0.0083474 |
| $KNO_3$ | 0.0665601 | — | — | 0.1026471 | — | — | 0.0582156 |
| $FeCl_3$ | — | 0.000407 | 0.0001194 | 0.00001196 | 0.001221058 | 0.000407 | 0.000407 |
| $MnCl_2$ | — | 0.0001554 | 0.00005553 | 0.0009061 | 0.000310703 | 0.0001554 | 0.0001554 |
| $ZnCl_2$ | — | 0.0143316 | — | 0.1470098 | 0.0286632 | 0.0143316 | 0.0143316 |
| $MgCl_2$ | — | 0.2551928 | 0.011368 | 0.7831424 | 0.452169898 | 0.2260849 | 0.2551928 |

TABLE 11-continued

| breakdown of all the chemicals and their amounts in each synthetic water (SW) formulation used for this experiment. | | | | | | | |
|---|---|---|---|---|---|---|---|
| Chemical | NSW (mM) | SW1 (mM) | SW2 (mM) | SW3 (mM) | SW4 (mM) | SW5 (mM) | SW6 (mM) |
| Mg $(NO_3)_2$ * $6H_2O$ | 0.34203167 | 0.0869093 | 1.7868376 | 0.2125781 | — | 0.1160171 | 0.0869093 |
| Ca $(NO_3)_2$ * $4H_2O$ | 0.84840319 | 0.6162865 | 0.2513667 | 0.9088404 | 2.05 | 0.2513216 | 1.5632894 |
| $CaSO_4$ | — | 0.2321591 | 0.0773423 | 1.0710196 | 1.231251559 | 0.0773423 | 0.0773423 |
| KCl | — | — | 0.0010632 | — | 0.058215628 | 0.0083474 | — |
| $MgSO_4$ | — | — | — | — | 0.232034175 | — | — |
| $Fe(NO_3)$ * $9H_2O$ | 0.40698299 | — | — | — | — | — | — |
| Mn $(NO_3)_2$ * $XH_2O$ | 0.15534583 | — | — | — | — | — | — |
| Zn $(NO_3)_2$ * $6H_2O$ | 0.0143316 | — | — | — | — | — | — |

TABLE 12

| The properties accompanying each synthetic water solution. | | | | | | | |
|---|---|---|---|---|---|---|---|
| Property | NSW | SW1 | SW2 | SW3 | SW4 | SW5 | SW6 |
| Ionic conductivity (μS/cm) | 800 | 219 | 382 | 709 | 615 | 195 | 430 |
| pH | 3.121 | 5.490 | 5.638 | 5.621 | 5.626 | 5.580 | 5.390 |
| [chlorides]/ mM | 0 | 0.540591 | 0.02426846 | 1.86215248 | 1.0241664 | 0.40907122 | 0.5405806 |
| [Nitrates]/ mM | 3.19376767 | 1.4063916 | 4.076486 | 2.3454841 | 4.1 | 0.7346774 | 3.358613 |
| [Sulfates]/ mM | 0 | 0.2321591 | 0.0773423 | 1.0710196 | 1.46328573 | 0.0773423 | 0.0773423 |

Figure 41:
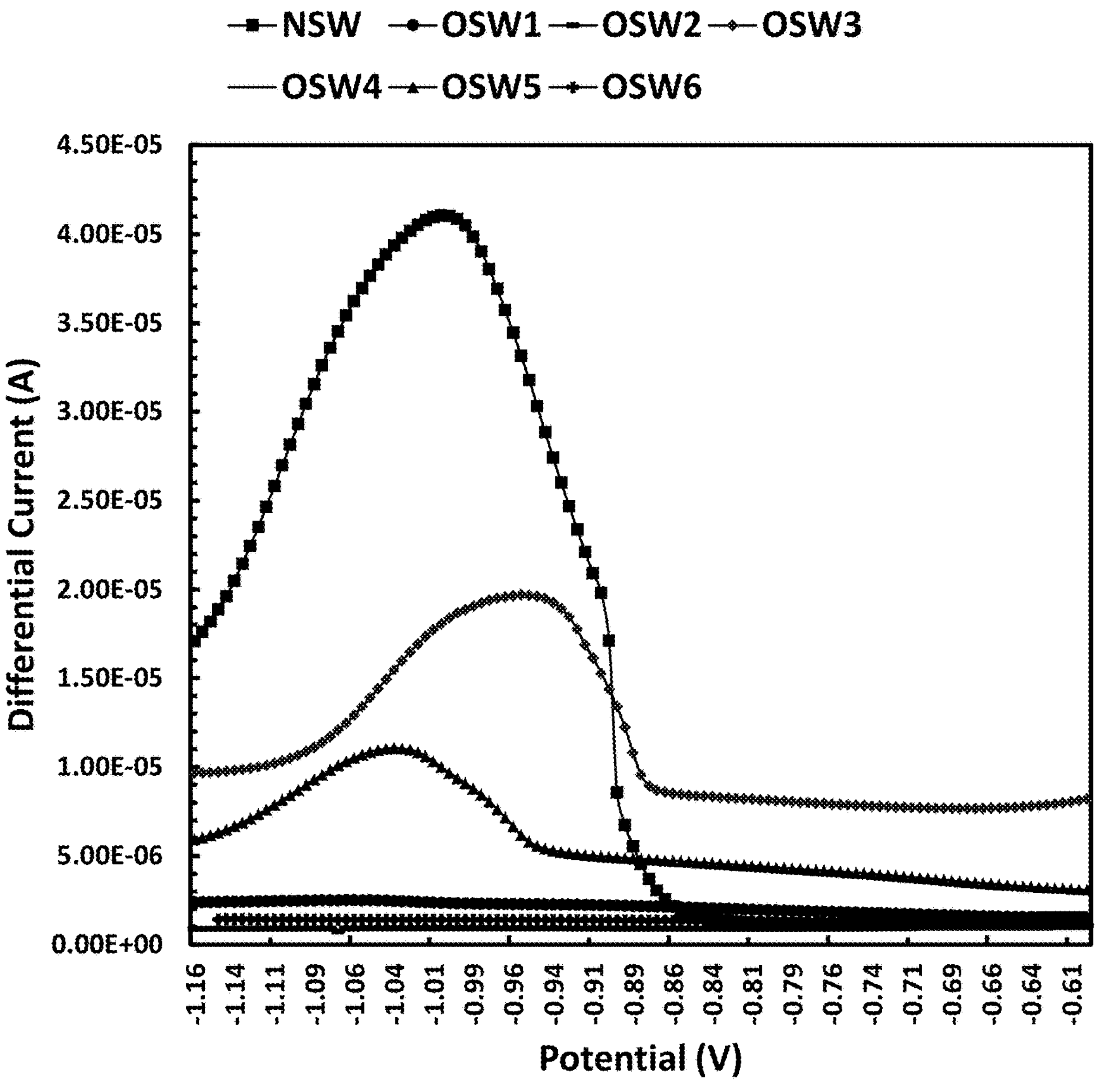
FIG. 41 is a voltammogram of the $25^{th}$ cycle of square wave voltammetry in a blank solution, as described in Example 19.
Figure 42:
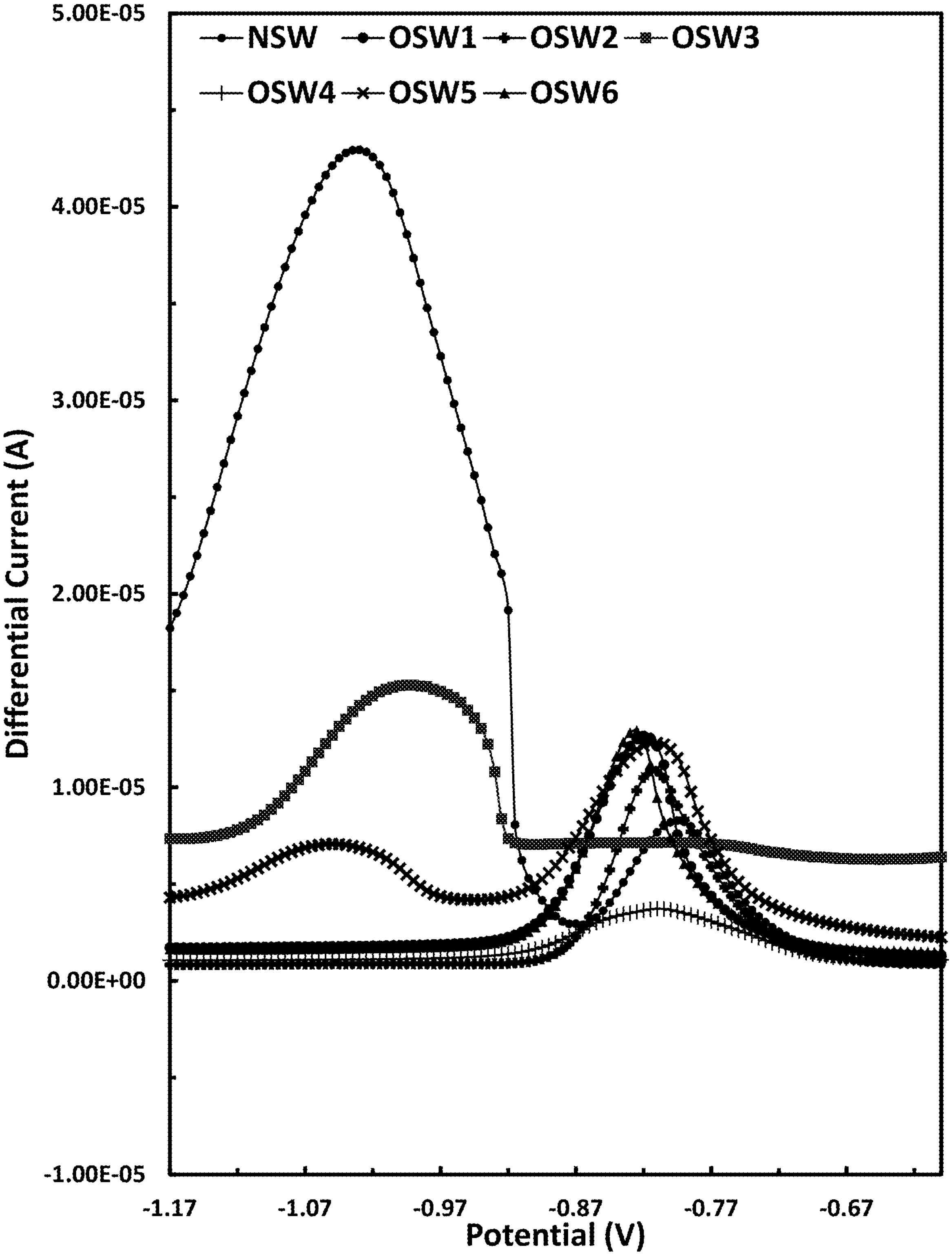
FIG. 42 is a voltammogram of the $25^{th}$ cycle of square wave voltammetry in a 100 ppb cadmium solution, as described in Example 19.
Figure 43:
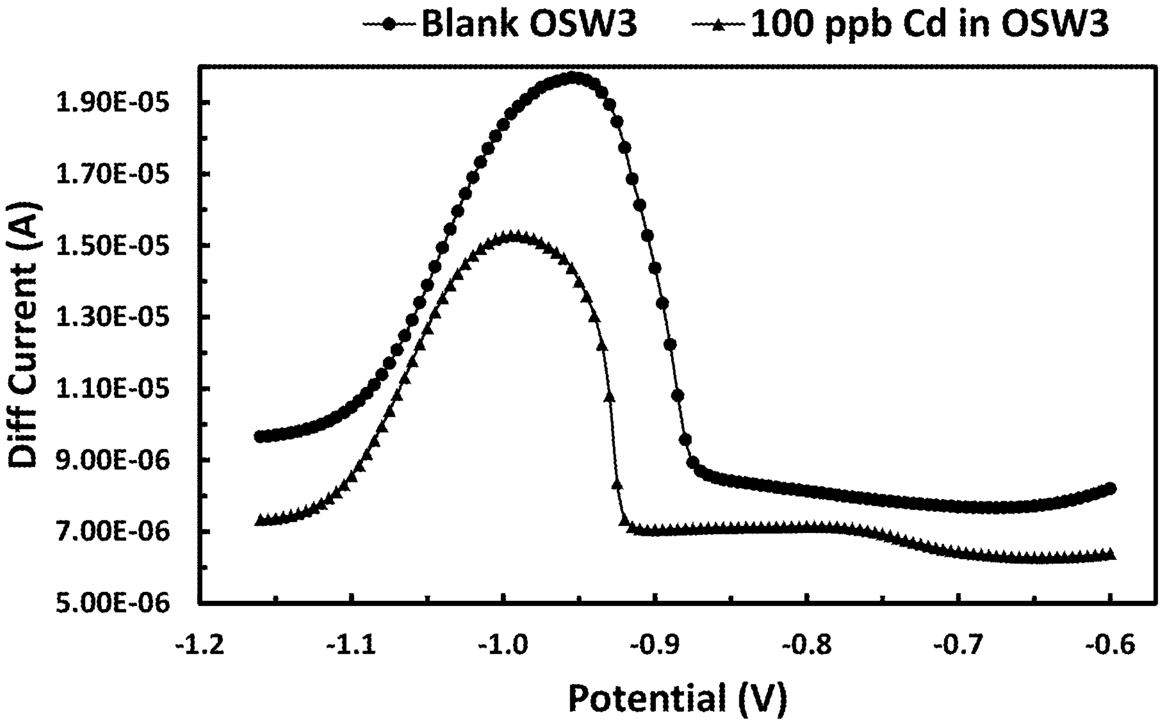
FIG. 43 is a voltammogram of the $25^{th}$ cycle of square wave voltammetry in a 100 ppb cadmium solution synthetic water #3, as described in Example 19.

The results are shown in FIGS. 41, 42, and 43. The figure overlays cycle 25 from one sensor of each solution in the blank (FIG. 41) and in the 100 ppb cadmium solution (FIG. 42). A cadmium peak can be observed in all solutions even with the differences between solutions highlighted in Tables 11 and 12. It should be noted that the peak is much smaller in SW3, which can be seen in FIG. 43. This experiment is a good example of how complementary sensors can be used to assist in the detection by measuring pH, conductivity, etc., and using these measurements to calibrate the sensor signal and optimize the cadmium oxidation peak around −0.8 V vs Ag/AgCl.

Example 20

Detection Limit Test for Copper

A detection limit test was performed using a sensor as fabricated in Example 7 for detecting copper. Square wave anodic stripping analysis was performed using a CHI660E electrochemical workstation coupled with CHI 684 multiplexer (CH Instruments Inc., USA). The potential window was from −0.5 V to −0.25 V with a frequency of 5 mV, increment of 5 mV, amplitude of 25 mV, sensitivity of $1e^{-5}$ A/V, and a quiet time of 60 s. Chronoamperometry was used as a cleaning cycle at 0.25 V for 30 s after each scan. There was no soak time for this experiment. There was an hour wait period between each cycle and the test was run for 50 cycles. For each solution made (volume of 250 mL), one sensor was placed in each bottle. The detection limit test was run in the synthetic water formulation described in Table 8 and DI water.

The concentration of copper for in each solution ranged from 0 ppb to 2 ppm at varying intervals. The resulting peak height (Ip), A, measured are shown in Table 13. For sensors in both solutions, copper was detectable down to concentrations of 0.8 ppb, well below the EPA limit of copper.

TABLE 13

| Results from the detection limit testing in DI water and synthetic water | | |
|---|---|---|
| [Copper]/ ppm | Ave Ip (μA) in SW#6 | Ave Ip (μA) in DI Water |
| 0.01 | — | — |
| 0.1 | — | — |
| 0.5 | — | — |
| 0.8 | 0.5672 | 1.0275 |
| 1 | 0.9881 | 1.633 |
| 1.3 (EPA limit) | 5.6695 | 2.195 |
| 2 | 9.1415 | 4.412 |

Example 21

Dosing Test for Copper Detection

Figure 44:
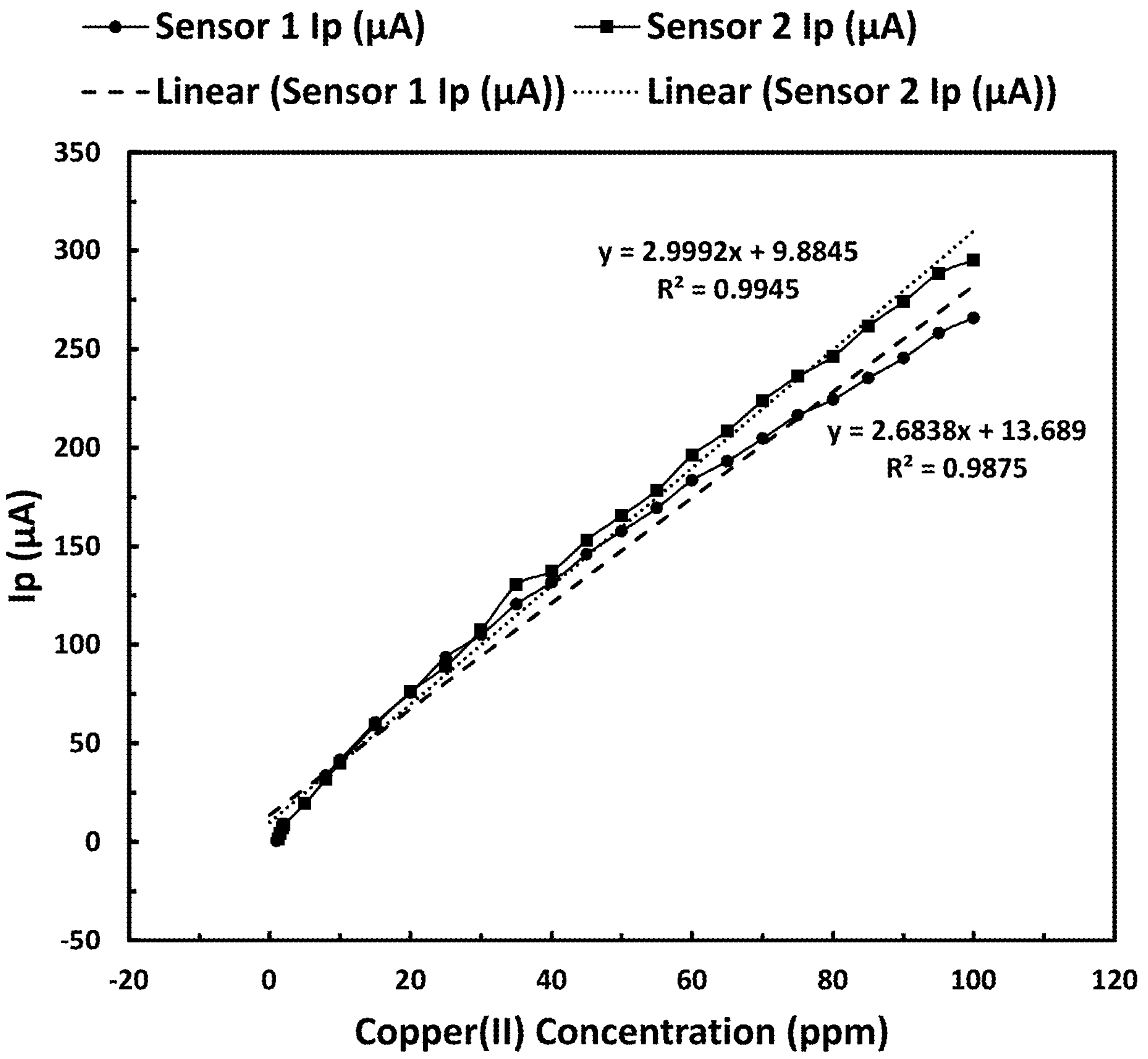
FIG. 44 shows the results of a dosing test using a series of copper solutions as described in Example 21.

A dosing test was performed using sensor as fabricated in Example 8 for detecting copper detection to establish a linear range, limit of detection and limit of linearity. Square wave anodic stripping analysis was performed using a CHI660E electrochemical workstation coupled with CHI 684 multiplexer (CH Instruments Inc., USA). The potential window was from −0.5 V to −0.25 V with a frequency of 5 mV, increment of 5 mV, amplitude of 25 mV, sensitivity of $1e^{-5}$ A/V for concentrations below 25 ppm, sensitivity of $1e^{-4}$ A/V for concentrations at or above 25 ppm, and a quiet time of 60 s. As the concentration increased, the sensitivity had to increase to obtain the full copper oxidation peak. Chronoamperometry was used as a cleaning cycle at 0.25 V for 30 s after each scan. There was no soak time for this experiment. Dosing occurred immediately after the cleaning cycle and the solution was stirred with a stir bar at 500 rpm for a minute between scans, and then was given another minute to allow the solution to slow before testing. The initial solution volume was 30 mL, at an initial copper concentration of 0 ppb in synthetic water. Concentrations of copper increased from 0.2 ppb to 100 ppm. Two sensors were used in this solution to compare the consistency of the dosing test between sensors. The results of this test are shown in FIG. 44. The results show that the linear range exceeds 100 ppm, as including these measurements in the linear range still yields an $R^2$ value of greater than 0.98 for both sensors. The results also verify the detection limit of 0.8 ppm, since the first Ip measurement that could be recorded was at this concentration.

We claim:

1. A voltammetric sensor system comprising:

a sensor comprising a working electrode, a counter electrode, and a reference electrode; and an electronic system connected to the working electrode, the counter electrode, and the reference electrode and being configured to:

apply a voltage difference between the working electrode and the reference electrode; and conduct a square wave voltammetric scan over at least a portion of an electrochemical window extending from a start scan value to an end scan value using the working electrode, the counter electrode, and the reference electrode, wherein the electronic system further comprises a dynamic electrochemical window calculator configured to change the end scan value of the electrochemical window to account for drift in the reference electrode, wherein:

the dynamic electrochemical window calculator is configured to store the start scan value, the end scan value, a baseline current value for current between the working electrode and the counter electrode, a threshold current value for current between the working electrode and the counter electrode that is offset above the baseline current value, and a voltage of significance value that is between the start scan value and the end scan value;

the electronic system is configured to conduct the square wave voltammetric scan starting at the start scan value and progressing in square wave steps to the voltage of significance value and then from the voltage of significance value toward the end scan value; and the dynamic electrochemical window calculator:

is configured to monitor current between the working electrode and the counter electrode as the square wave voltammetric scan progresses from the voltage of significance value toward the end scan value to determine if said current between the working electrode and the counter electrode exceeds the threshold current value; and comprises a current limiter that interrupts the square wave voltammetric scan before the square wave voltammetric scan reaches the end scan value to limit oxidation of the working electrode if said current between the working electrode and the counter electrode exceeds the threshold current value after the square wave voltammetric scan has progressed to the voltage of significance value.

2. The voltammetric sensor system as set forth in claim 1, wherein the sensor is configured to conduct the square wave voltammetric scan.

3. The voltammetric sensor system as set forth in claim 1, wherein the reference electrode comprises a pseudo-reference electrode.

4. The voltammetric sensor system as set forth in claim 1, wherein the electronic system is configured to allow the current between the working electrode and the counter electrode to exceed the threshold current value without interrupting the square wave voltammetric scan as the square wave voltammetric scan is progressing from the start scan value to the voltage of significance value.

5. The voltammetric sensor system as set forth in claim 1, wherein the dynamic electrochemical window calculator is configured so that, in an event the square wave voltammetric scan is interrupted because the current between the working electrode and the counter electrode exceeds the threshold current value, the end scan value is changed to coincide with a point at which the current between the working electrode and the counter electrode exceeded the threshold current value and caused an interruption.

6. The voltammetric sensor system as set forth in claim 1, wherein the dynamic electrochemical window calculator is configured to change the end scan value by moving the end scan value closer to a peak in the current between the counter electrode and the working electrode associated with oxidation of the working electrode in an event the square wave voltammetric scan progresses to the end scan value without causing the current between the working electrode and the counter electrode to exceed the threshold current value.

7. The voltammetric sensor system as set forth in claim 5, wherein the dynamic electrochemical window calculator is configured to change the start scan value whenever the dynamic electrochemical window calculator changes the end scan value to shift the electrochemical window without changing a range of the electrochemical window.

8. The voltammetric sensor system as set forth in claim 1, wherein the electronic system is configured to conduct a reference scan to determine initial values for at least the baseline current value, the voltage of significance value, and the end scan value.

9. The voltammetric sensor system as set forth in claim 8, wherein the reference scan results in a peak in the current between the working electrode and the counter electrode caused by oxidation of the working electrode, and wherein the electronic system is configured to set the initial value of the voltage of significance value to a value that is before the peak caused by oxidation of the working electrode.

10. The voltammetric sensor system as set forth in claim 1, wherein initial values for the baseline current value, the voltage of significance value, and the end scan value are stored in the electronic system and based on empirical knowledge of the sensor.

11. The voltammetric sensor system as set forth in claim 1, wherein the electronic system is configured to allow a user to input a user-defined offset, the threshold current value being offset above the baseline current value by the user-defined offset.

12. A method of using the voltammetric sensor system of claim 1, the method comprising:

applying, via the electronic system, the square wave voltammetric scan over at least a portion of the electrochemical window extending from the start scan value to the end scan value using the working electrode, the counter electrode, and the reference electrode;

determining, via the electronic system, the drift in the reference electrode; and changing, via the electronic system, the end scan value to account for the drift in the reference electrode.

13. The method as set forth in claim 12, wherein changing the end scan value comprises moving the end scan value away from a peak associated with oxidation of the working electrode.

14. The method as set forth in claim 12, further comprising changing the start scan value whenever the end scan value is changed to shift an entirety of the electrochemical window.

* * * * *